United States Patent
Koga et al.

(10) Patent No.: US 6,207,076 B1
(45) Date of Patent: *Mar. 27, 2001

(54) FLUOROVINYL DERIVATIVE COMPOUND, LIQUID CRYSTAL COMPOSITION, AND LIQUID CRYSTAL DISPLAY DEVICE

(75) Inventors: Kouji Koga; Kazutoshi Miyazawa; Hiroyuki Takeuchi; Shuichi Matsui, all of Chiba; Norihisa Hachiya, Saitama; Fusayuki Takeshita; Etsuo Nakagawa, both of Chiba, all of (JP)

(73) Assignee: Chisso Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/242,105

(22) PCT Filed: Aug. 25, 1997

(86) PCT No.: PCT/JP97/02942

§ 371 Date: May 26, 1999

§ 102(e) Date: May 26, 1999

(87) PCT Pub. No.: WO98/08791

PCT Pub. Date: Mar. 5, 1998

(30) Foreign Application Priority Data

Aug. 26, 1996 (JP) .................................... 8-242698

(51) Int. Cl.$^7$ .......................... C09K 19/30; C09K 19/34; C09K 19/12
(52) U.S. Cl. ................ 252/299.63; 252/299.61; 252/299.66
(58) Field of Search ............. 252/299.63, 299.61, 252/299.66; 568/626

(56) References Cited

U.S. PATENT DOCUMENTS

| | | | |
|---|---|---|---|
| 4,877,548 | * 10/1989 | Kitano et al. | 252/299.63 |
| 4,880,562 | * 11/1989 | Kitano et al. | 252/299.63 |
| 5,183,587 | * 2/1993 | Kitano et al. | 252/299.63 |
| 5,328,642 | * 7/1994 | Rieger et al. | 252/299.63 |
| 5,364,556 | * 11/1994 | Schadt et al. | 252/299.01 |
| 5,403,512 | * 4/1995 | Bartmann et al. | 252/299.01 |
| 5,653,911 | 8/1997 | Kondo et al. | 252/299.01 |
| 5,663,463 | * 9/1997 | Shinya et al. | 570/128 |
| 5,720,899 | * 2/1998 | Kondo et al. | 252/299.01 |
| 5,723,682 | * 3/1998 | Poetsch et al. | 568/655 |
| 5,911,912 | * 6/1999 | Kirsch et al. | 252/299.01 |
| 5,914,071 | * 6/1999 | Shinya et al. | 252/299.63 |
| 5,919,396 | * 7/1999 | Tarumi et al. | 252/299.01 |
| 5,989,452 | * 11/1999 | Kato et al. | 252/299.63 |

FOREIGN PATENT DOCUMENTS

| | | |
|---|---|---|
| 43 14 085 | 11/1994 | (DE) . |
| 195 20 246 | 6/1995 | (DE) . |
| 0 325 796 | 8/1989 | (EP) . |
| 0 377 469 | 7/1990 | (EP) . |
| 0 593 997 | 4/1994 | (EP) . |
| 61-83136 | 4/1986 | (JP) . |
| 4-502627 | 5/1992 | (JP) . |
| 6-500343 | 1/1994 | (JP) . |
| 07 082 181 | 3/1995 | (JP) . |
| 8-12605 | 1/1996 | (JP) . |
| 91 19772 | 12/1991 | (WO) . |

OTHER PUBLICATIONS

"Polar Alkenyls: Physical Properties and Correlations with Molecular Structure of New Nematic Liquid Crystals", by Schadt et al., Mol. Cryst. Liq. Cryst., 1985, vol. 122, pp. 241–260.

* cited by examiner

*Primary Examiner*—C. H. Kelly
(74) *Attorney, Agent, or Firm*—McDermott, Will & Emery

(57) ABSTRACT

There are herein disclosed a fluorovinyl derivative compound represented by the general formula (1) and having characteristics of a liquid crystal, a liquid crystal composition, and a liquid crystal display device formed by using this composition:

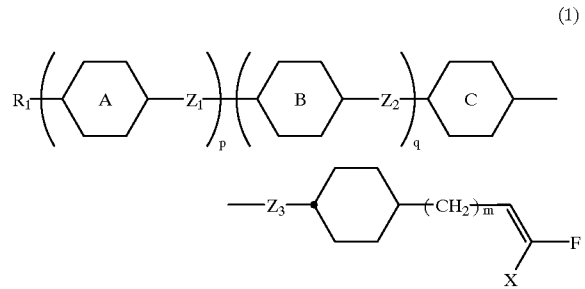

(1)

wherein $R_1$ is an alkyl group having 1 to 18 carbon atoms, and a methylene group in the alkyl group may be substituted by an oxygen atom, a sulfur atom, —CH=CH— or —C≡C— and a hydrogen atom in the alkyl group may be substituted a halogen atom or a cyano group; rings A, B and C are each 1,4-cyclohexylene, 1,4-phenylene or the like in which a hydrogen atom in the ring may be substituted by a halogen atom; $Z_1$, $Z_2$ and $Z_3$ are each a single bond, —CH$_2$CH$_2$—, —CH=CH—, —C≡C—, —CH$_2$O—, —OCH$_2$—, —(CH$_2$)$_4$—, —(CH$_2$)$_3$—O—, —O—(CH$_2$)$_3$—, —(CH$_2$)$_2$—CH=CH—, —CH=CH—(CH$_2$)$_2$—, —CF$_2$O—, —OCF$_2$—, —CR$_2$=CH—, —CH=CR$_2$— or —CF=CF—, and $R_2$ is an alkyl group having 1 to 5 carbon atoms; X is a hydrogen atom or a fluorine atom; p and q are each 0 or 1; and m is an integer of 0 to 5.

30 Claims, No Drawings

FLUOROVINYL DERIVATIVE COMPOUND, LIQUID CRYSTAL COMPOSITION, AND LIQUID CRYSTAL DISPLAY DEVICE

TECHNICAL FIELD

The present invention relates to a novel liquid crystal compound useful as a liquid crystal display material. More specifically, it relates to a novel liquid crystal compound having suitable characteristics such as steep threshold properties, a low viscosity, a good compatibility with another liquid crystal compound and a proper optical anisotropy value, a novel liquid crystal composition and a liquid crystal display device formed by using this compound.

BACKGROUND ART

Heretofore, liquid crystal compounds are important as compounds for use in the manufacture of displays of various electrooptic devices. Among the various liquid crystal compounds, compounds having an alkenyl group as a side chain are suitable as the liquid crystal compounds for STN, and the various compounds having the alkenyl group have been synthesized and evaluated, and some of these compounds have been put to practical use. For example, the following compounds (s-1) to (s-3) have been disclosed in Mol. Cryst. Liq. Cryst., 122, p. 241 (1985) and Japanese Patent Application Laid-open No. 83136/1986, the following compounds (s-4) and (s-5) have been revealed in Japanese Patent Application No. 92740/1994, and the following compounds (s-6) and (s-7) have been disclosed in DE19520246Al.

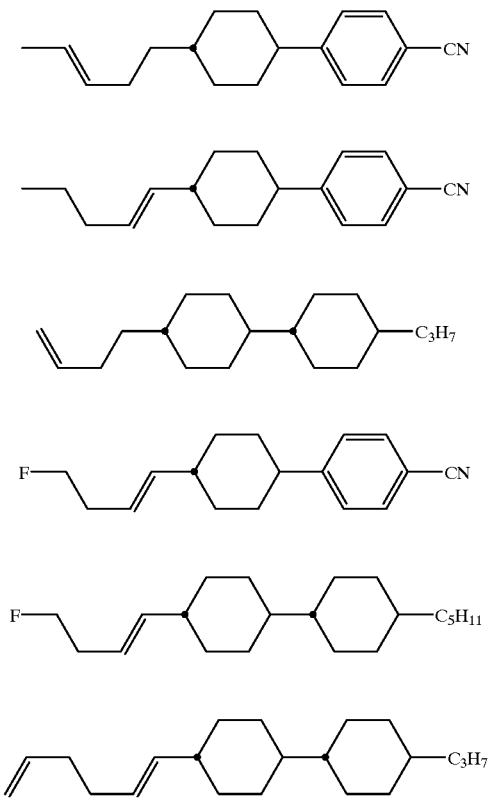

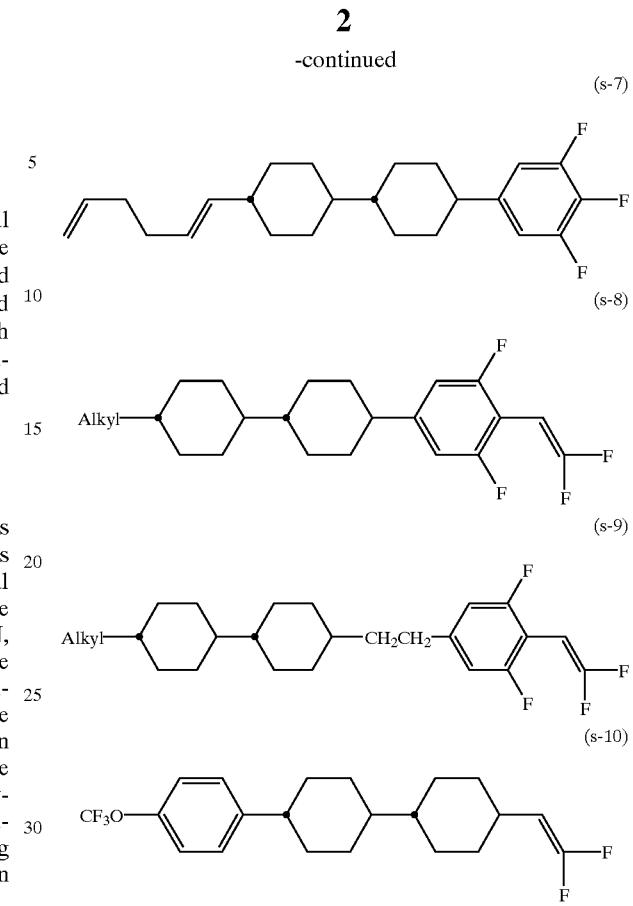

However, the above liquid crystal compounds are poor in steep threshold properties which are required for the liquid crystal compounds for STN, and all of them have strong smectogenic properties, so that if a liquid crystal composition containing a large amount of such a compound is prepared, there is a problem that the compatibility of such a liquid crystal compound with another liquid crystal compound in the liquid crystal composition at a low temperature is low. In particular, the compounds (s-4) to (s-7) have each a high viscosity, and so there is a large problem that a response speed of the liquid crystal composition using such a compound is low.

Compounds (s-8) and (s-9) in which a fluorine atom is directly bonded to a double bond have been disclosed in Japanese Patent National Publication (Kohyo) No. 500343/1994, and a compound (s-10) has been revealed in Japanese Patent National Publication (Kohyo) No. 502627/1992. However, the compounds (s-8) and (s-9) are extremely poor in chemical stability (particularly, heat stability), and therefore the use of these compounds is practically impossible. Moreover, in Japanese Patent National Publication (Kohyo) No. 502627/1992, there have been disclosed compounds alone in which a terminal group is limited to a polar group such as a halogen atom.

DISCLOSURE OF THE INVENTION

The present inventors have intensively investigated to solve the above problems, and as a result, it has been found that a fluorovinyl derivative compound represented by the general formula (1) has (1) an extremely high elastic constant ratio ($K_{33}/K_{11}$), (2) a very low viscosity, (3) a wide nematic phase temperature range,
(4) a high chemical stability, and
(5) a proper optical anisotropy value and dielectric anisotropy value.

Furthermore, it has also been found that a liquid crystal composition in which the compound of the general formula (1) is used has
(1) steep threshold voltage properties,
(2) a feature that a response time is short,
(3) a wide operation temperature range (a good compatibility with another liquid crystal compound),
(4) a chemical stability, and
(5) a feature that a drive power is low.

In addition, it has also been confirmed that the compound of the general formula (1) is suitable for the preparation of the liquid crystal composition for STN (super-twisted nematic) which is most extensively used at present. In consequence, the present invention has now been completed.

Therefore, an object of the present invention is to provide a novel fluorovinyl derivative compound suitable for a display material, and a liquid crystal composition in which this compound is used. In particular, the object of the present invention is to provide a novel liquid crystal compound having steep threshold properties, a low viscosity, a good compatibility with another liquid crystal compound and a proper optical anisotropy value and dielectric anisotropy value, a novel liquid crystal composition and a liquid crystal display device formed by using this compound.

The present invention which can achieve the above object is constituted as follows.

The 1st aspect of the present invention is directed to a fluorovinyl derivative compound represented by the general formula (1)

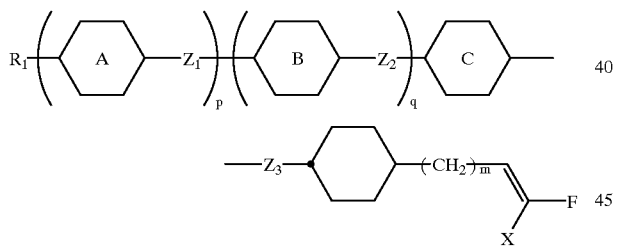

(1)

wherein $R_1$ is an alkyl group having 1 to 18 carbon atoms, and a methylene group in the alkyl group may be substituted by an oxygen atom, a sulfur atom, —CH=CH— or —C≡C— and a hydrogen atom in the alkyl group may be substituted by a halogen atom or a cyano group;

rings A, B and C are each independently 1,4-cyclohexylene, 1,4-cyclohexenylene, 1,4-phenylene, 1,3-dioxane-2,5-diyl, pyridine-2,5-diyl or pyrimidine-2,5-diyl in which a hydrogen atom in the ring may be substituted by a halogen atom;

$Z_1$, $Z_2$ and $Z_3$ are each independently a single bond, —CH$_2$CH$_2$—, —CH=CH—, —CH$_2$O—, —OCH$_2$—, —(CH$_2$)$_4$—, —(CH$_2$)$_3$—O—, —O—(CH$_2$)$_3$—, —(CH$_2$)$_2$—CH=CH—, —CH=CH—(CH$_2$)$_2$—, —CF$_2$O—, —OCF$_2$—, —CR$_2$=CH—, —CH=CR$_2$— or —CF=CF—, and $R_2$ is an alkyl group having 1 to 5 carbon atoms;

X is a hydrogen atom or a fluorine atom; p and q are each independently 0 or 1; and m is an integer of 0 to 5;

each element in the formula may be substituted by its isotope; but except (1) a compound in which p is 0, q is 0, $Z_3$ is the single bond, —CH$_2$CH$_2$—, —CH$_2$O— or —OCH$_2$—, and the ring C is 1,4-cyclohexylene or 1,4-phenylene, and (2) a compound in which p is 0, q is 1, $Z_2$ and $Z_3$ are each the single bond, the ring B is 1,4-phenylene, and the ring C is 1,4-cyclohexylene or 1,4-phenylene.

The 2nd aspect of the present invention is directed to the fluorovinyl derivative compound according to the 1st aspect of the present invention wherein at least one of $Z_1$, $Z_2$ and $Z_3$ is —CH=CH—, —(CH$_2$)$_3$—O—, —O—(CH$_2$)$_3$—, —(CH$_2$)$_2$—CH=CH—, —CH=CH—(CH$_2$)$_2$—, —CF$_2$O—, —OCF$_2$—, —CR$_2$=CH—, —CH=CR$_2$— or —CF=CF—; and $R_2$ is an alkyl group having 1 to 5 carbon atoms.

The 3rd aspect of the present invention is directed to the fluorovinyl derivative compound according to the 1st aspect of the present invention wherein at least one of $Z_1$, $Z_2$ and $Z_3$ is —CH=CH—, —(CH$_2$)$_2$—CH=CH—, —CH=CH—(CH$_2$)$_2$— or —CF=CF—.

The 4th aspect of the present invention is directed to the fluorovinyl derivative compound according to the 1st aspect of the present invention wherein at least one of $Z_1$, $Z_2$ and $Z_3$ is —(CH$_2$)$_3$—O—, —O—(CH$_2$)$_3$—, —CF$_2$O— or —OCF$_2$—.

The 5th aspect of the present invention is directed to the fluorovinyl derivative compound according to the 1st aspect of the present invention wherein at least one of $Z_1$, $Z_2$ and $Z_3$ is —CR$_2$=CH— or —CH=CR$_2$—; and $R_2$ is an alkyl group having 1 to 5 carbon atoms.

The 6th aspect of the present invention is directed to a fluorovinyl derivative compound represented by the general formula (1-1)

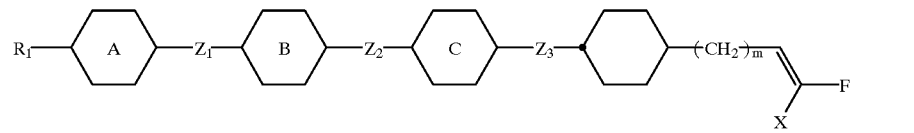

(1-1)

wherein $R_1$, X and m are as defined in the 1st aspect of the present invention; $Z_1$, $Z_2$ and $Z_3$ are each independently a single bond, —CH$_2$CH$_2$—, —CH$_2$O—, —OCH$_2$— or —(CH$_2$)$_4$—; and rings A, B and C are each independently 1,4-cyclohexylene or 1,4-phenylene in which a hydrogen atom in the ring may be substituted by a halogen atom.

The 7th aspect of the present invention is directed to a fluorovinyl derivative compound represented by the general formula (1-2)

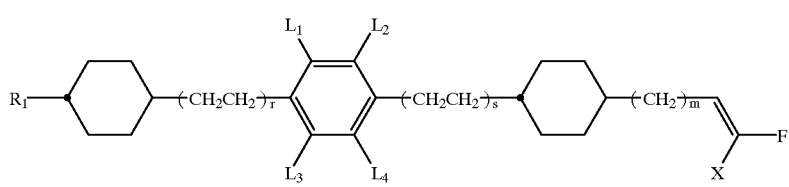

(1-2)

wherein $R_1$, X and m are as defined in the 1st aspect of the present invention; r and s are each independently 0 or 1; and $L_1$, $L_2$, $L_3$ and $L_4$ are each independently a hydrogen atom or a fluorine atom.

Typical examples of the compound represented by the general formula (1-2) include compounds of the following formulae:

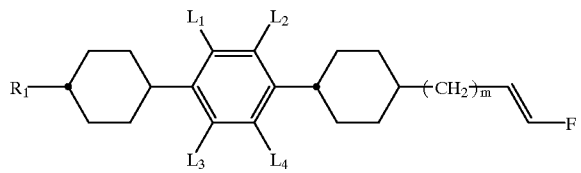

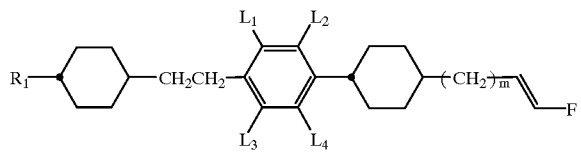

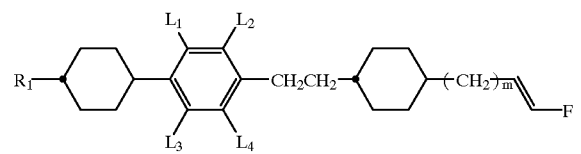

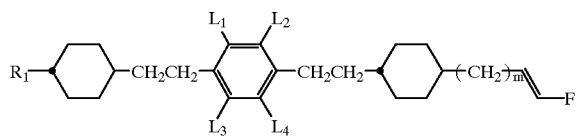

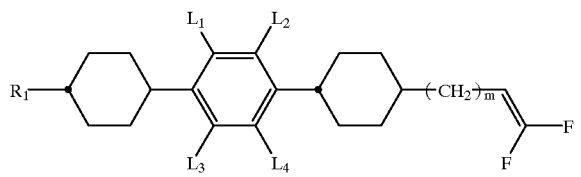

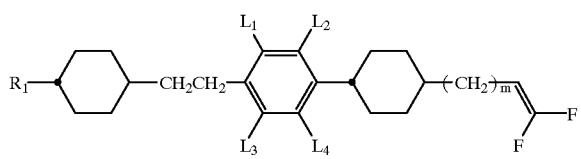

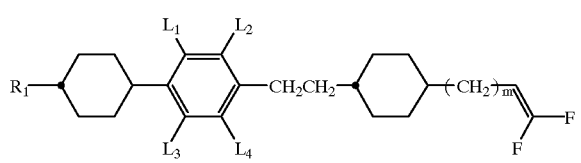

-continued

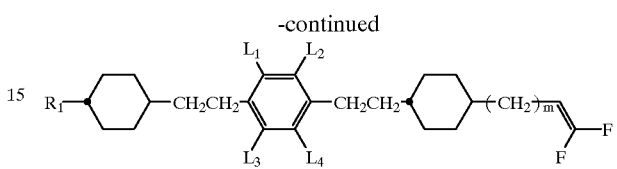

wherein $R_1$, m and $L_1$ to $L_4$ are as defined above.

The 8th aspect of the present invention is directed to the fluorovinyl derivative compound according to the 7th aspect of the present invention wherein r+s is 1 or 0.

The 9th aspect of the present invention is directed to the fluorovinyl derivative compound according to the 7th aspect of the present invention wherein r+s is 2.

The 10th aspect of the present invention is directed to a fluorovinyl derivative compound represented by the general formula (1-3)

(1-3)

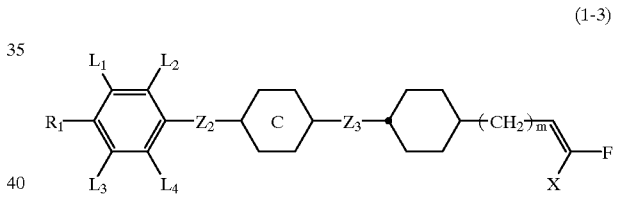

wherein $R_1$, X, m, $L_1$, $L_2$, $L_3$ and $L_4$ are as defined in the 7th aspect of the present invention; $Z_2$ and $Z_3$ are each independently a single bond, —CH$_2$CH$_2$—, —CH$_2$O—, —OCH$_2$— or —(CH$_2$)$_4$—, and $Z_2$ and $Z_3$ are not simultaneously the single bonds; and a ring C is 1,4-cyclohexylene or 1,4-phenylene in which a hydrogen atom in the ring may be substituted by a halogen atom.

Typical examples of the compound represented by the general formula (1-3) include compounds of the following formulae:

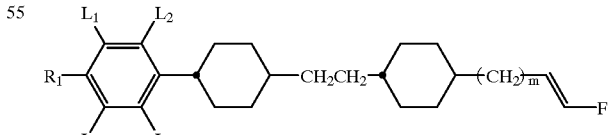

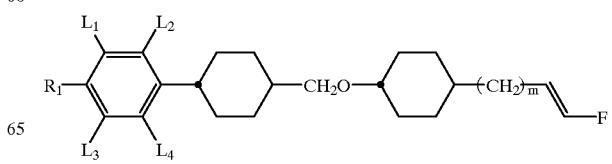

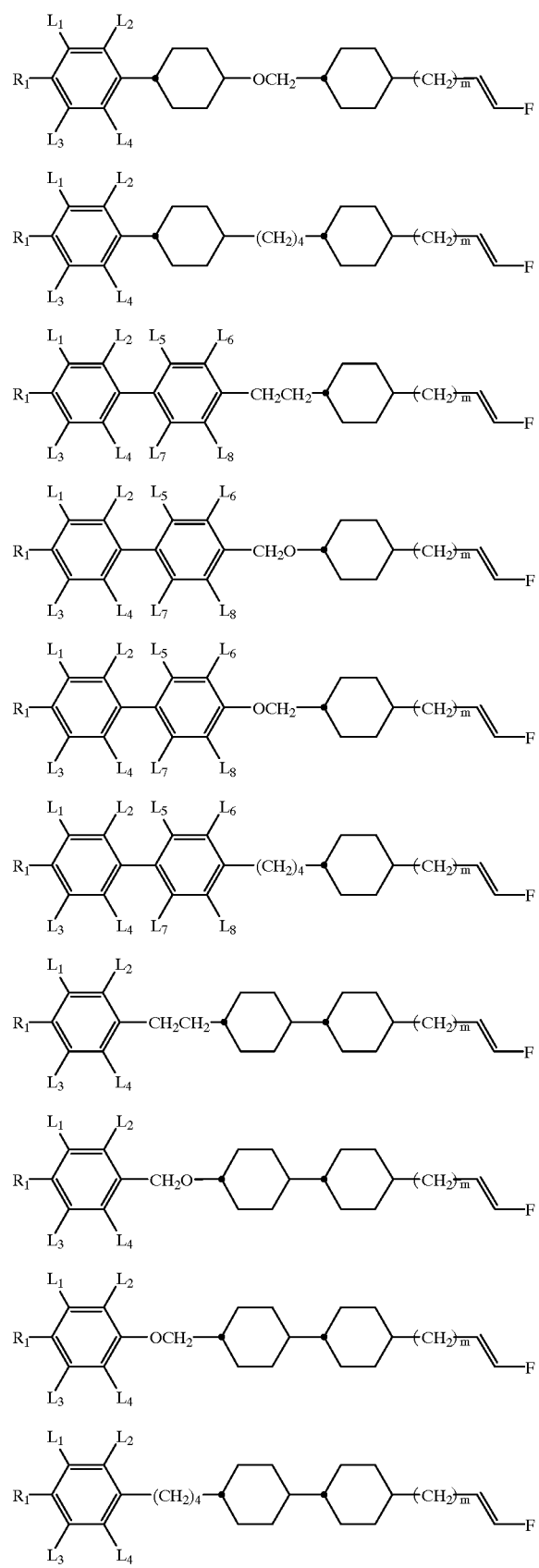
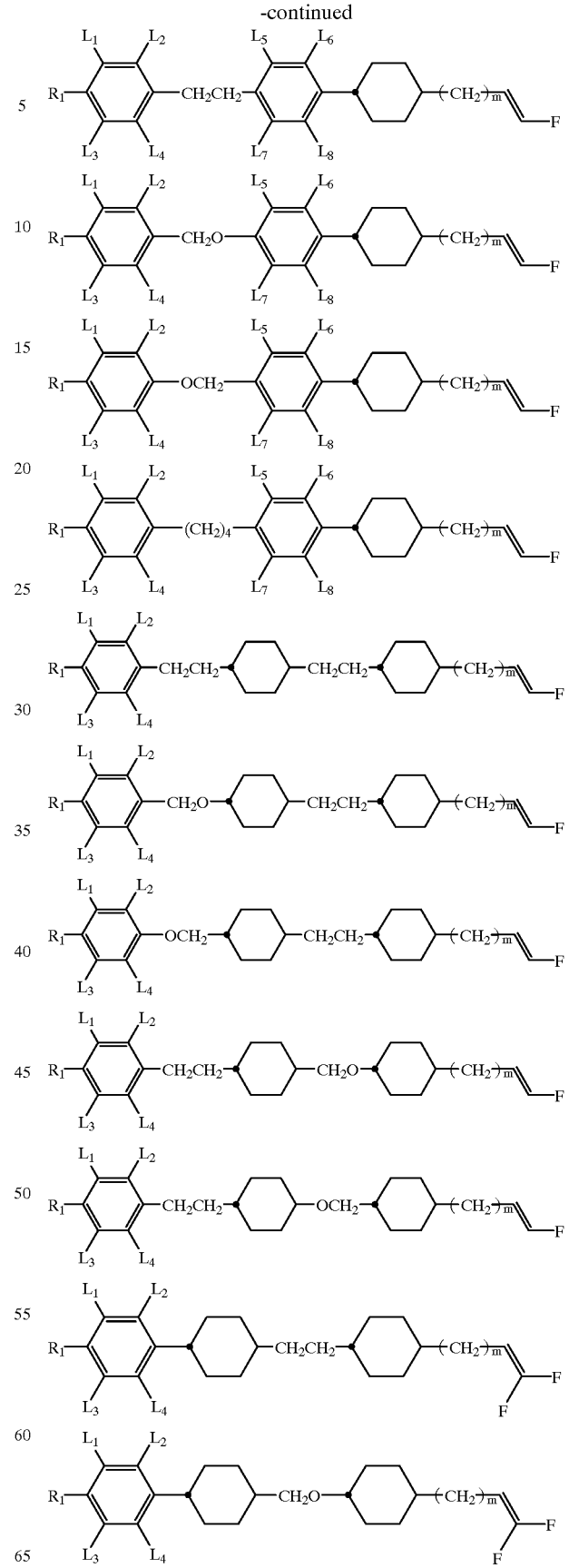

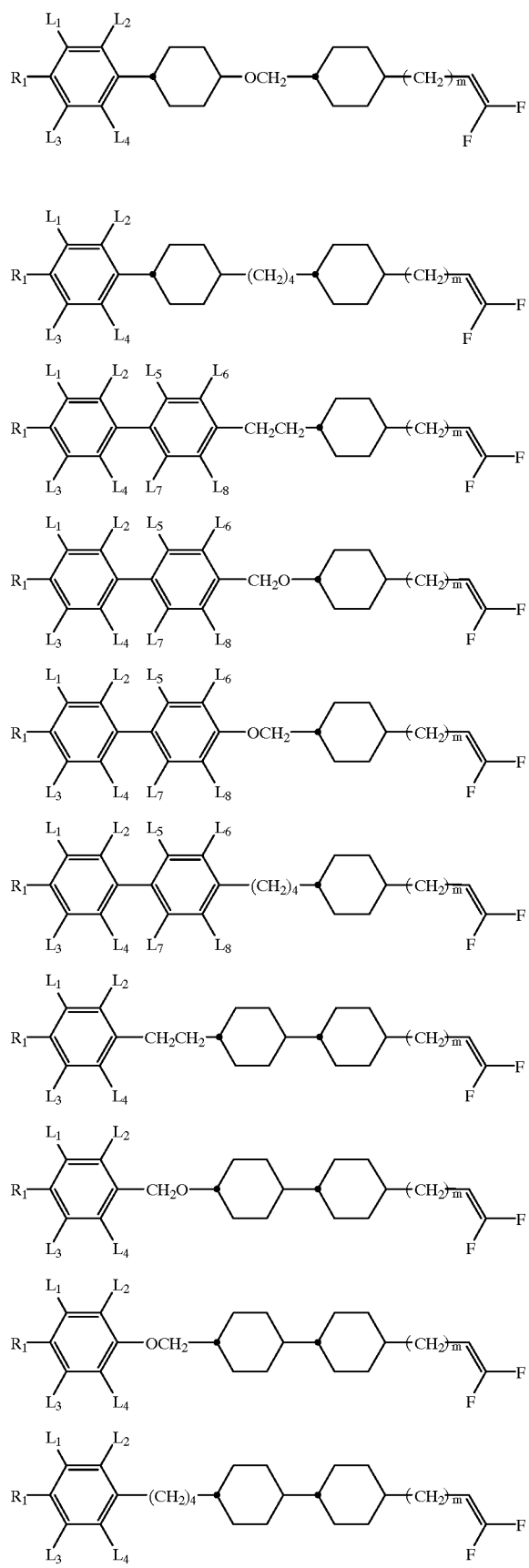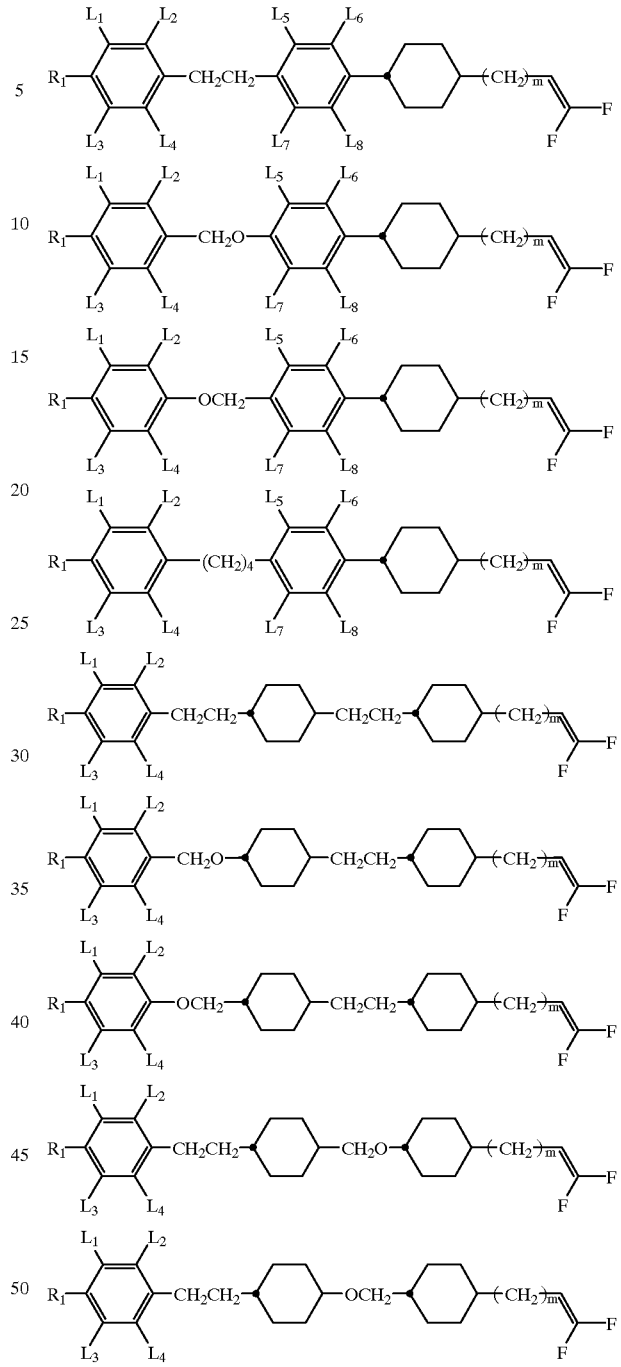

wherein $R_1$, m and $L_1$ to $L_8$ are as defined above.

The 11th aspect of the present invention is directed to the fluorovinyl derivative compound according to the 10th aspect of the present invention wherein the ring C is 1,4-cyclohexylene.

The 12th aspect of the present invention is directed to the fluorovinyl derivative compound according to the 10th aspect of the present invention wherein the ring C is 1,4-phenylene in which a hydrogen atom in the ring may be substituted by a halogen atom.

The 13th aspect of the present invention is directed to a fluorovinyl derivative compound represented by the general formula (1-1-1)

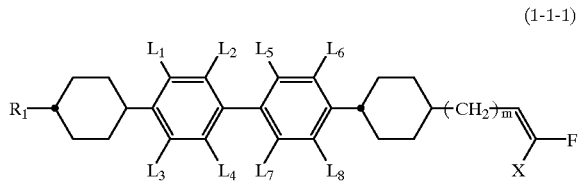

(1-1-1)

wherein $R_1$, X and m are as defined in the 1st aspect of the present invention; and $L_1$ to $L_8$ are each independently a hydrogen atom or a fluorine atom.

Typical examples of the compound represented by the general formula (1-1-1) include compounds of the following formulae:

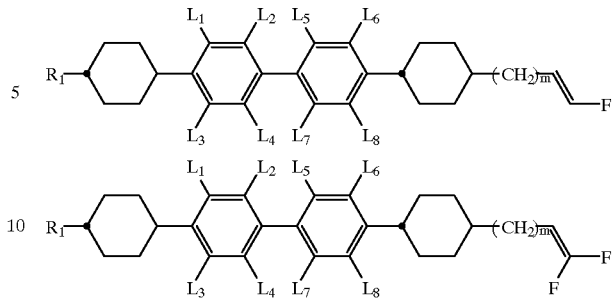

wherein $R_1$, m and $L_1$ to $L_8$ are as defined above.

The 14th aspect of the present invention is directed to a fluorovinyl derivative compound represented by the general formula (1-1-2)

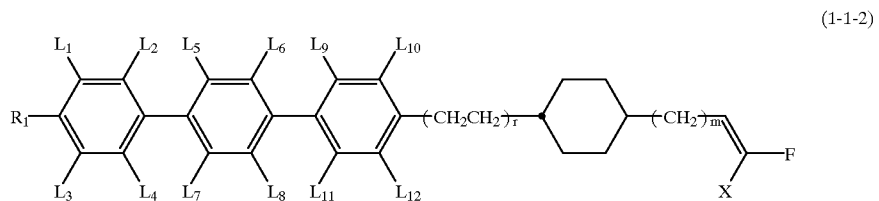

(1-1-2)

wherein $R_1$, X and m are as defined in the 1st aspect of the present invention; $L_1$ to $L_{12}$ are each independently a hydrogen atom or a fluorine atom; and r is 0 or 1.

Typical examples of the compound represented by the general formula (1-1-2) include compounds of the following formulae:

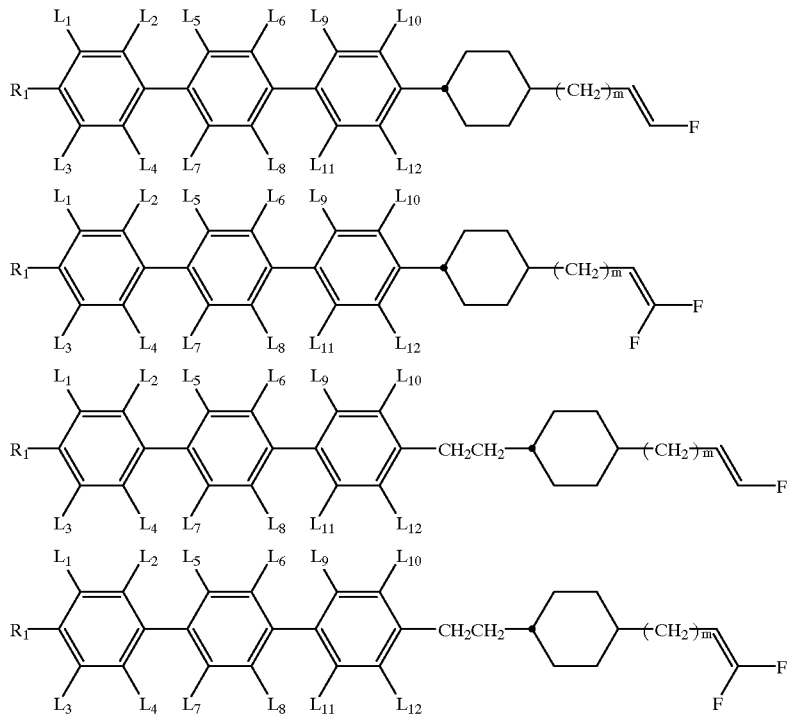

wherein $R_1$, m and $L_1$ to $L_{12}$ are as defined above.

The 15th aspect of the present invention is directed to a fluorovinyl derivative compound represented by the general formula (1-1-3)

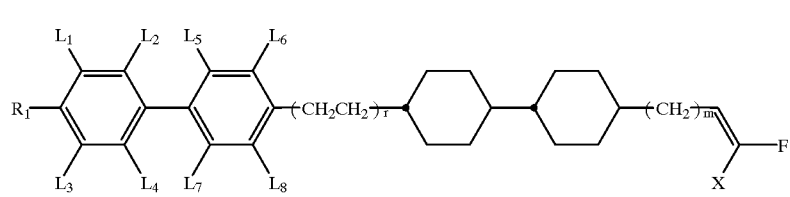

(1-1-3)

wherein $R_1$, X and m are as defined in the 1st aspect of the present invention; $L_1$ to $L_8$ are each independently a hydrogen atom or a fluorine atom; and r is 0 or 1.

Typical examples of the compound represented by the general formula (1-1-3) include compounds of the following formulae:

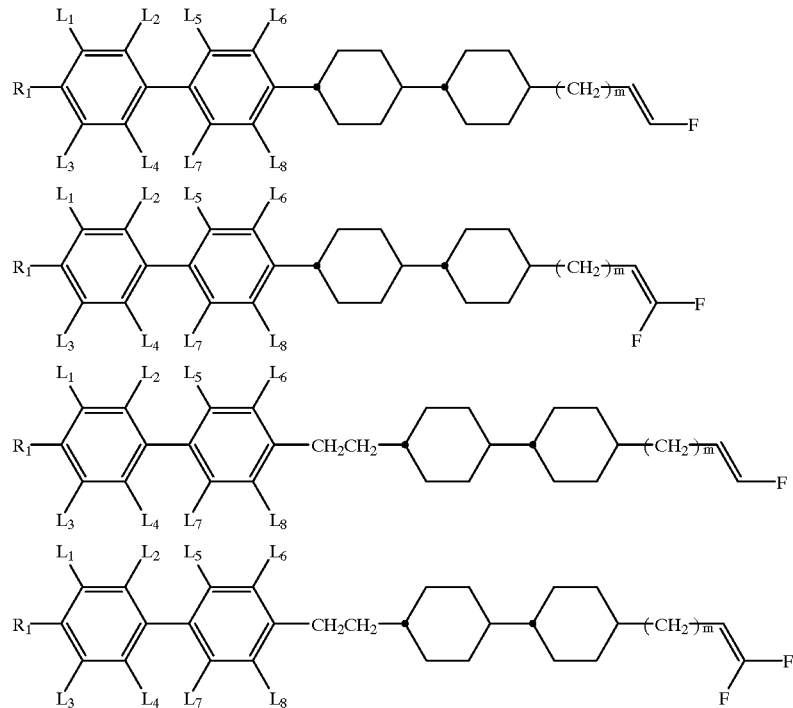

wherein $R_1$, m and $L_1$ to $L_8$ are as defined above.

The 16th aspect of the present invention is directed to a fluorovinyl derivative compound represented by the general formula (1-4-1)

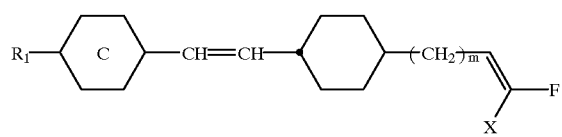

(1-4-1)

wherein $R_1$, X and m are as defined in the 1st aspect of the present invention; and the ring C is 1,4-cyclohexylene or 1,4-phenylene in which a hydrogen atom in the ring may be substituted by a halogen atom.

Typical examples of the compound represented by the general formula (1-4-1) include compounds of the following formulae:

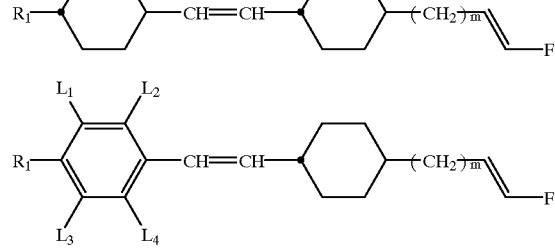

-continued

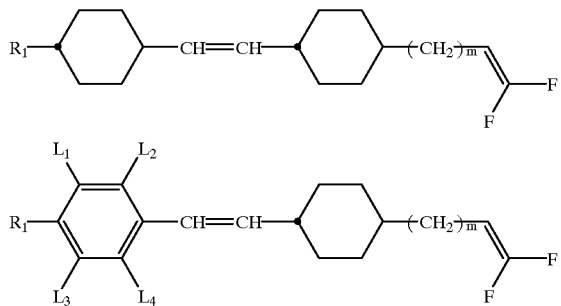

wherein $R_1$, m and $L_1$ to $L_4$ are as defined above.

The 17th aspect of the present invention is directed to a fluorovinyl derivative compound represented by the general formula (1-4-2)

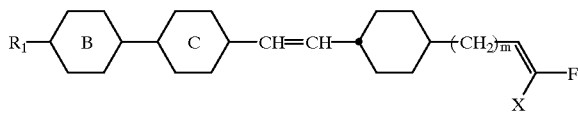

(1-4-2)

wherein $R_1$, X and m are as defined in the 1st aspect of the present invention; and the rings B and C are each 1,4-cyclohexylene or 1,4-phenylene in which a hydrogen atom in the ring may be substituted by a halogen atom.

Typical examples of the compound represented by the general formula (1-4-2) include compounds of the following formulae:

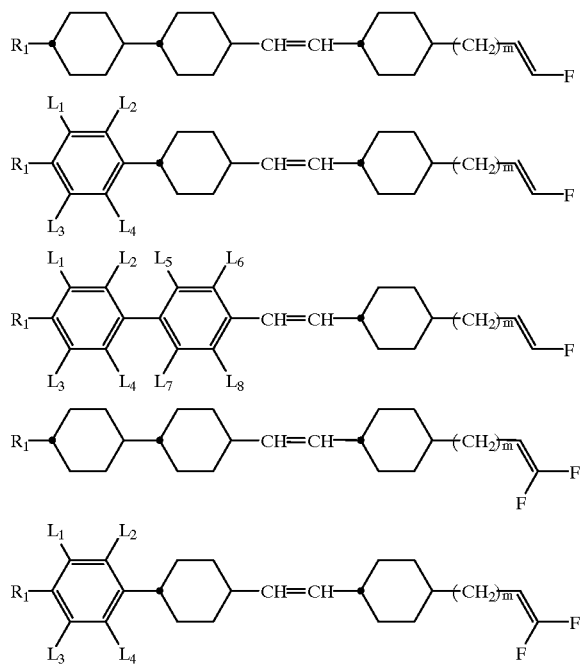

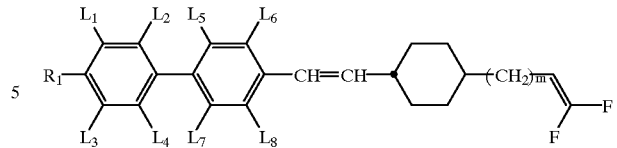

wherein $R_{11}$ m and $L_1$ to $L_5$ are as defined above.

The 18th aspect of the present invention is directed to a fluorovinyl derivative compound represented by the general formula (1-4-3)

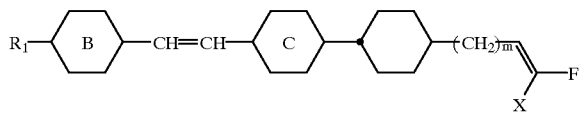

(1-4-3)

wherein $R_1$, X and m are as defined in the 1st aspect of the present invention; and the rings B and C are each 4-cyclohexylene or 1,4-phenylene in which a hydrogen atom in the ring may be substituted by a halogen atom.

Typical examples of the compound represented by the general formula (1-4-3) include compounds of the following formulae:

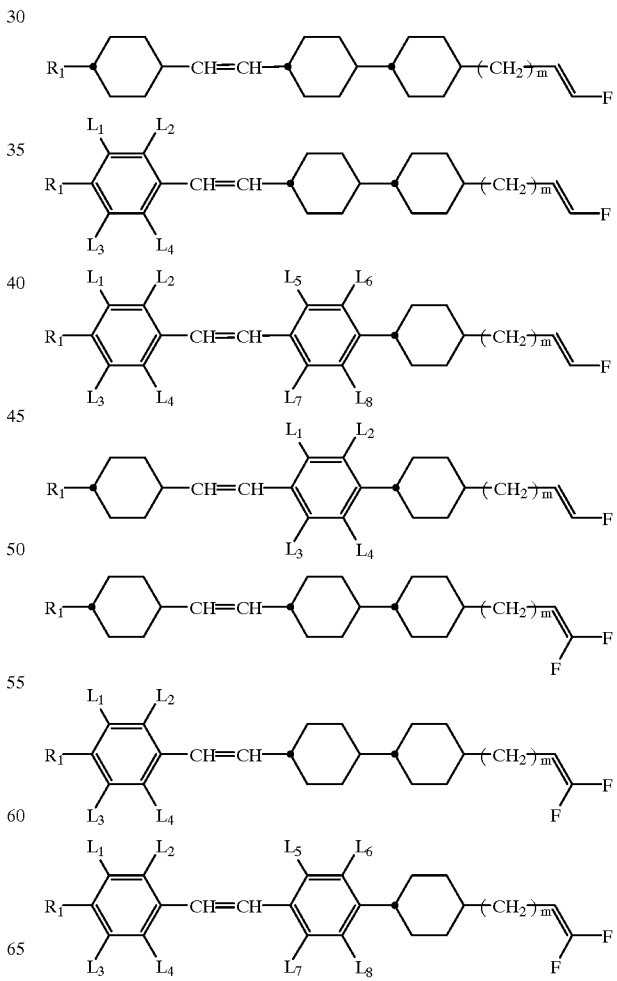

-continued

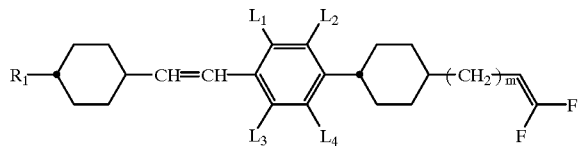

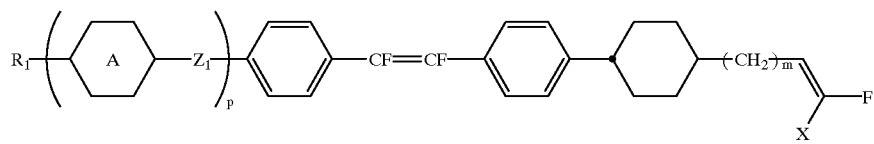

(1-4-4)

wherein $R_1$, m and $L_1$ to $L_8$ are as defined above.

The 19th aspect of the present invention is directed to a fluorovinyl derivative compound represented by the general formula (1-4-4)

wherein $R_1$, X, m, $Z_1$ and p are as defined in the 1st aspect of the present invention; and the ring A is 1,4-cyclohexylene or 1,4-phenylene in which a hydrogen atom in the ring may be substituted by a halogen atom.

Typical examples of the compound represented by the general formula (1-4-4) include compounds of the following formulae:

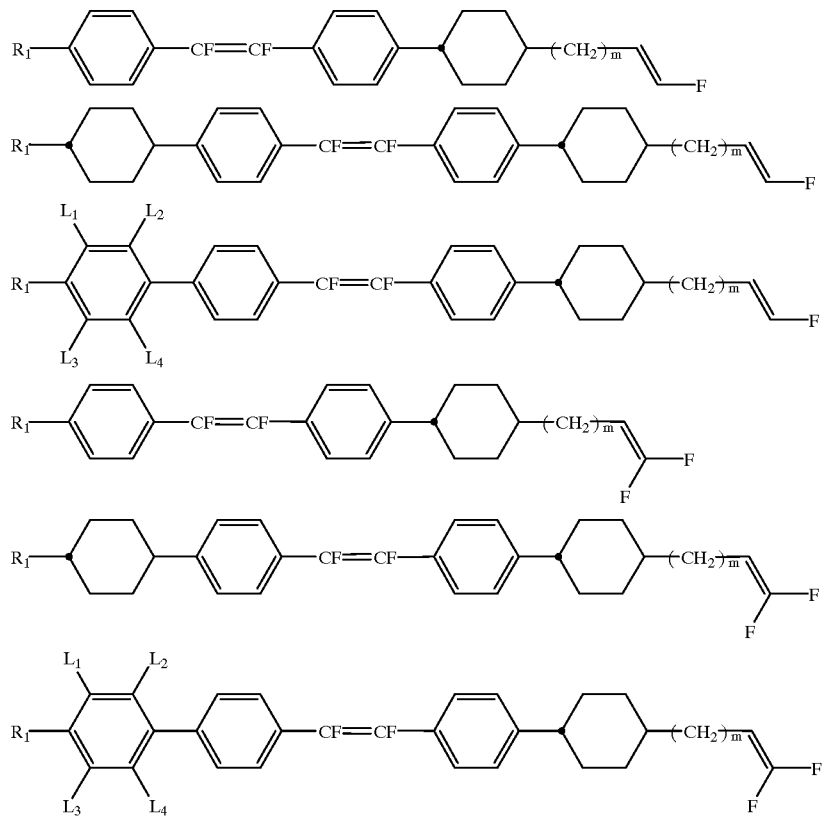

wherein $R_1$, m and $L_1$ to $L_4$ are as defined above.

The 20th aspect of the present invention is directed to a fluorovinyl derivative compound represented by the general formula (1-4-5)

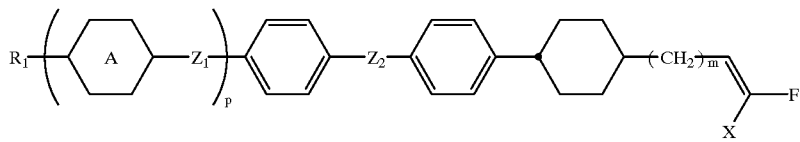
(1-4-5)
wherein $R_1$, X, m, $Z_1$ and p are as defined in the 1st aspect of the present invention; the ring A is 1,4-cyclohexylene or 1,4-phenylene in which a hydrogen atom in the ring may be substituted by a halogen atom; and $Z_2$ is —$CF_2O$— or —$OCF_2$—.
Typical examples of the compound represented by the general formula (1-4-5) include compounds of the following formulae:
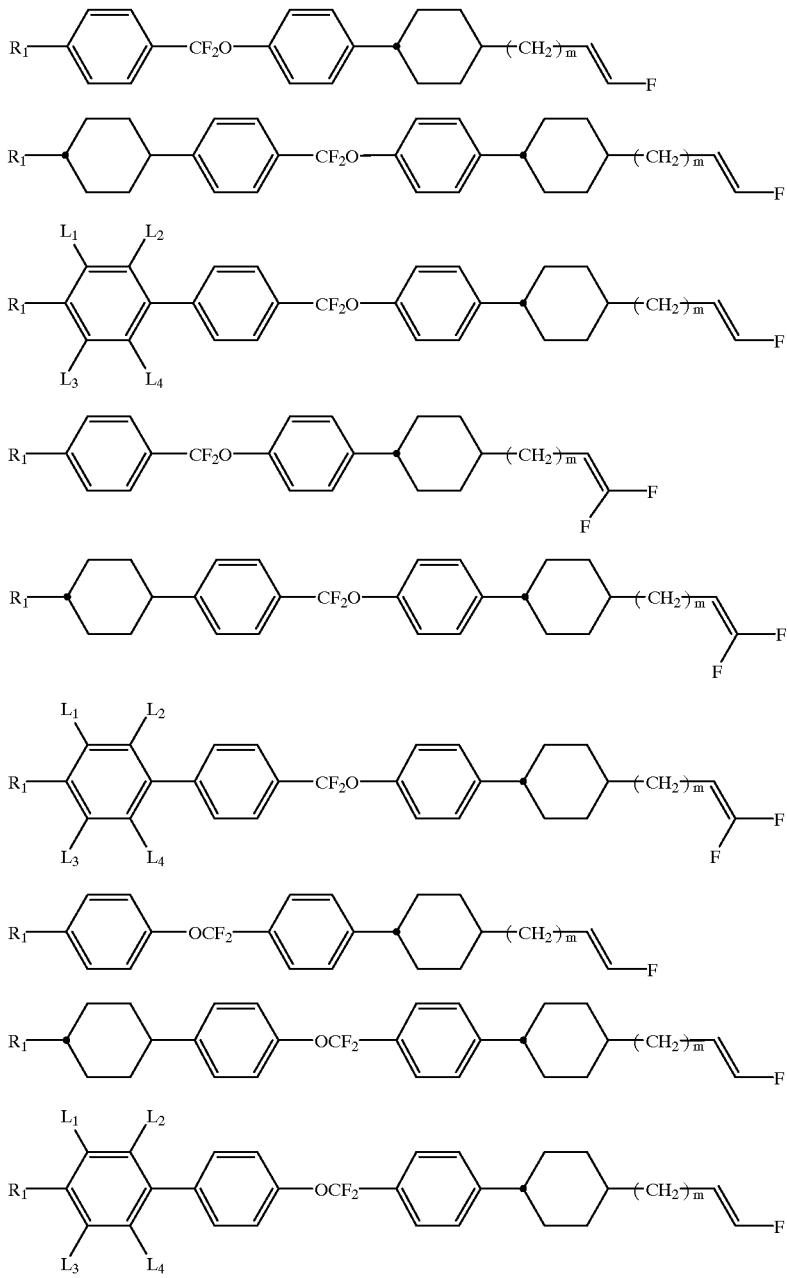

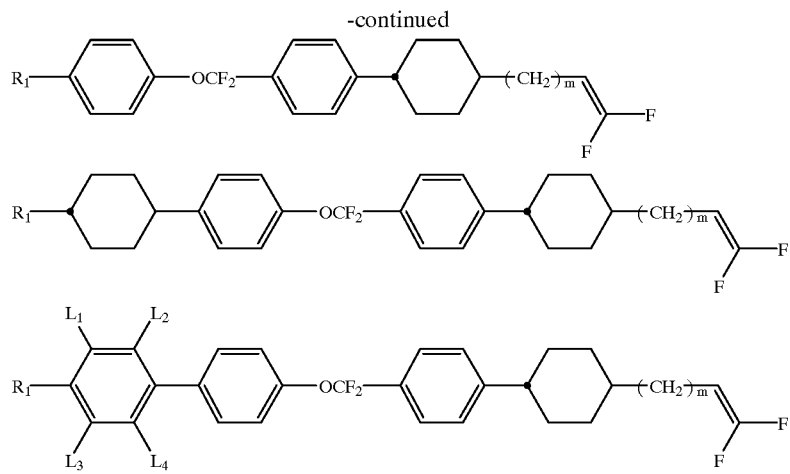

wherein $R_1$, m and $L_1$ to $L_4$ are as defined above.

The 21st aspect of the present invention is directed to a fluorovinyl derivative compound represented by the general formula (1-4-6)

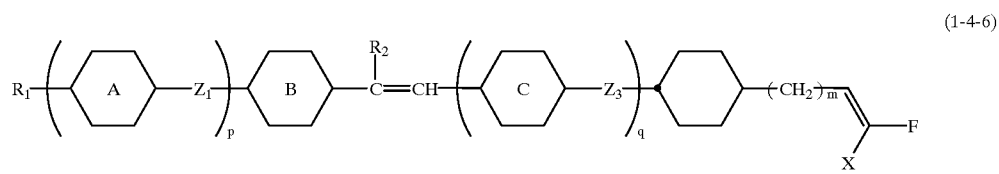

(1-4-6)

wherein $R_1$, X, m, $Z_1$ $Z_3$, p and q are as defined in the 1st aspect of the present invention; the rings A, B and C are each 1,4-cyclohexylene or 1,4-phenylene in which a hydrogen atom in the ring may be substituted by a halogen atom; and $R_2$ is an alkyl group having 1 to 5 carbon atoms.

Typical examples of the compound represented by the general formula (1-4-6) include compounds of the following formulae:

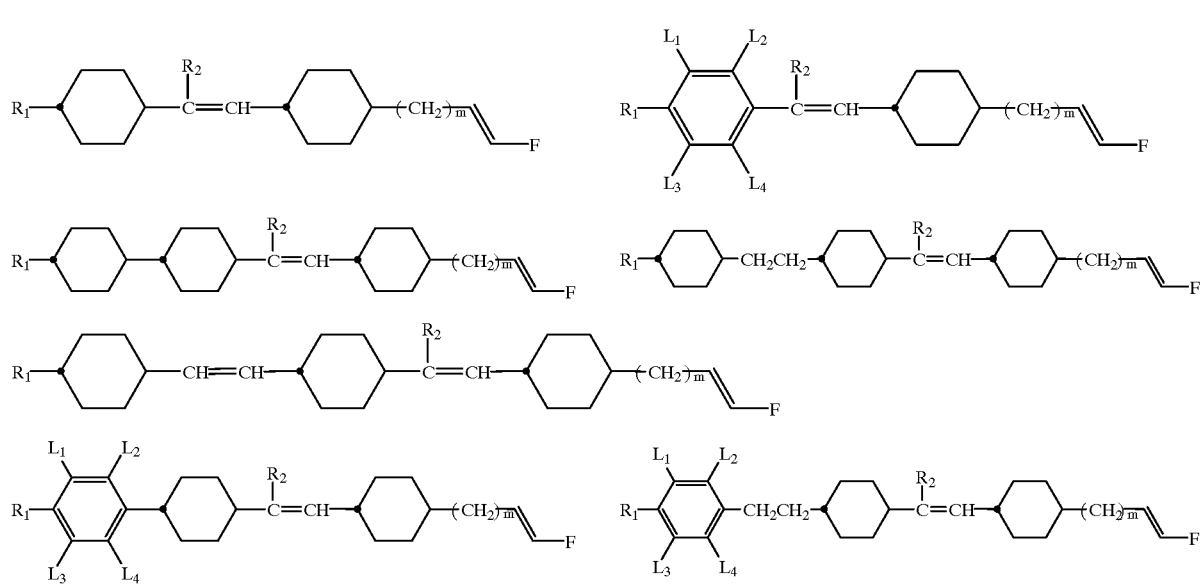

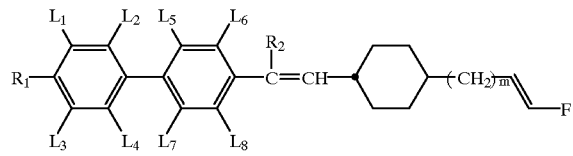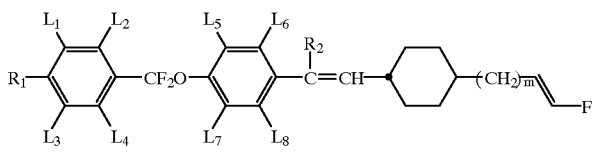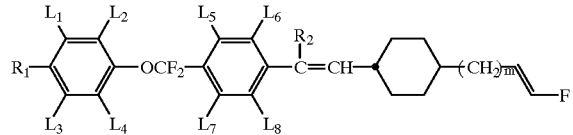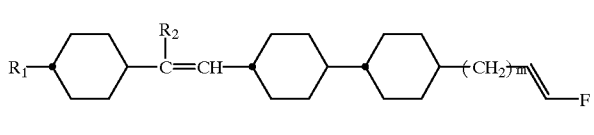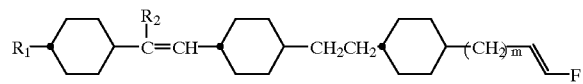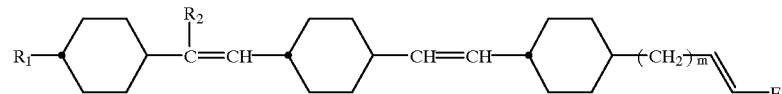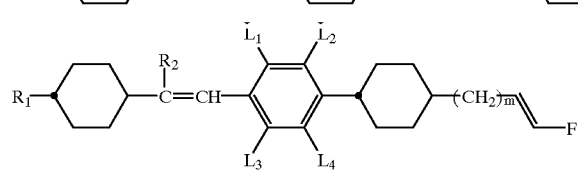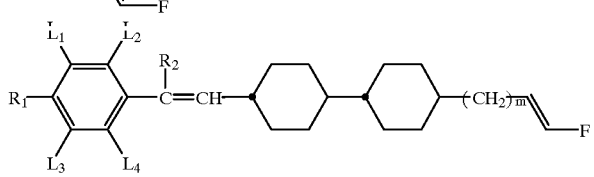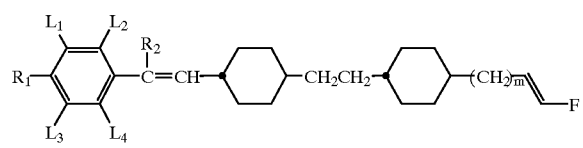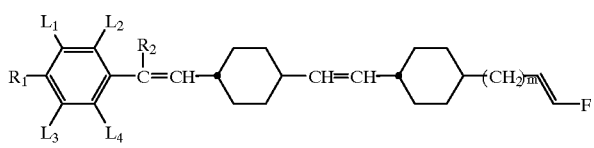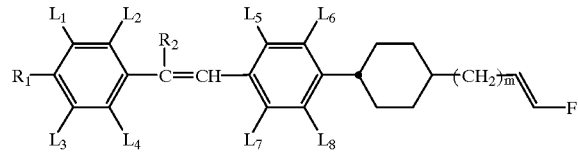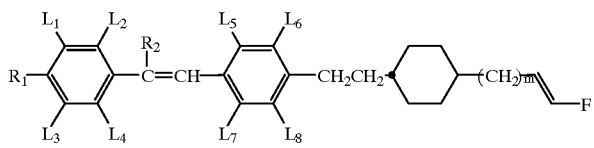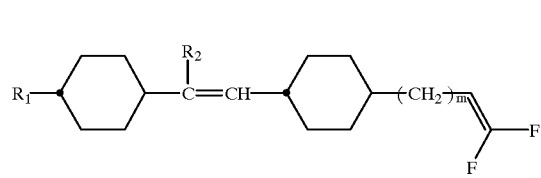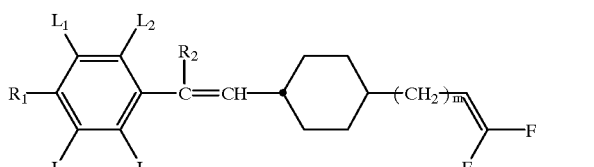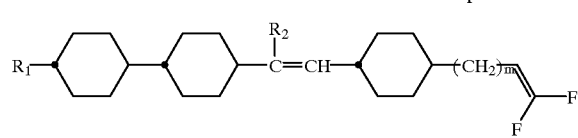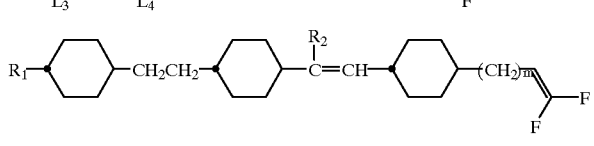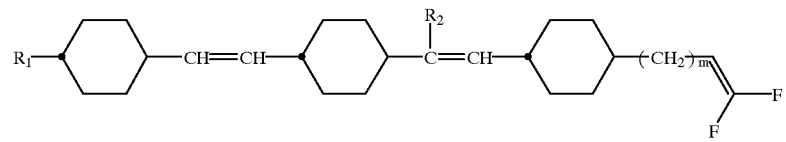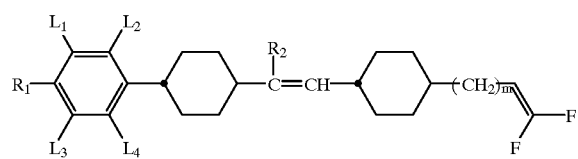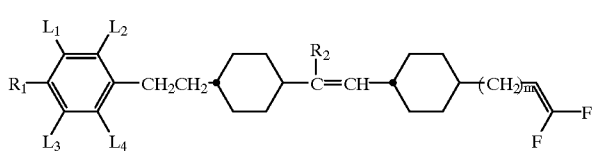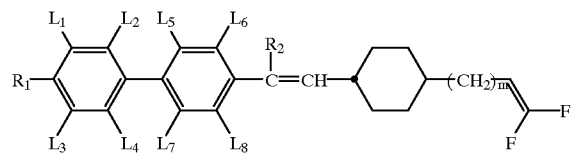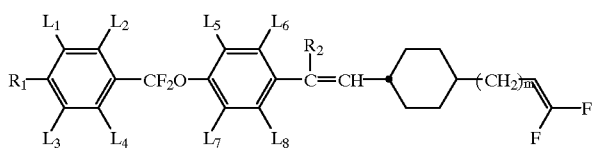

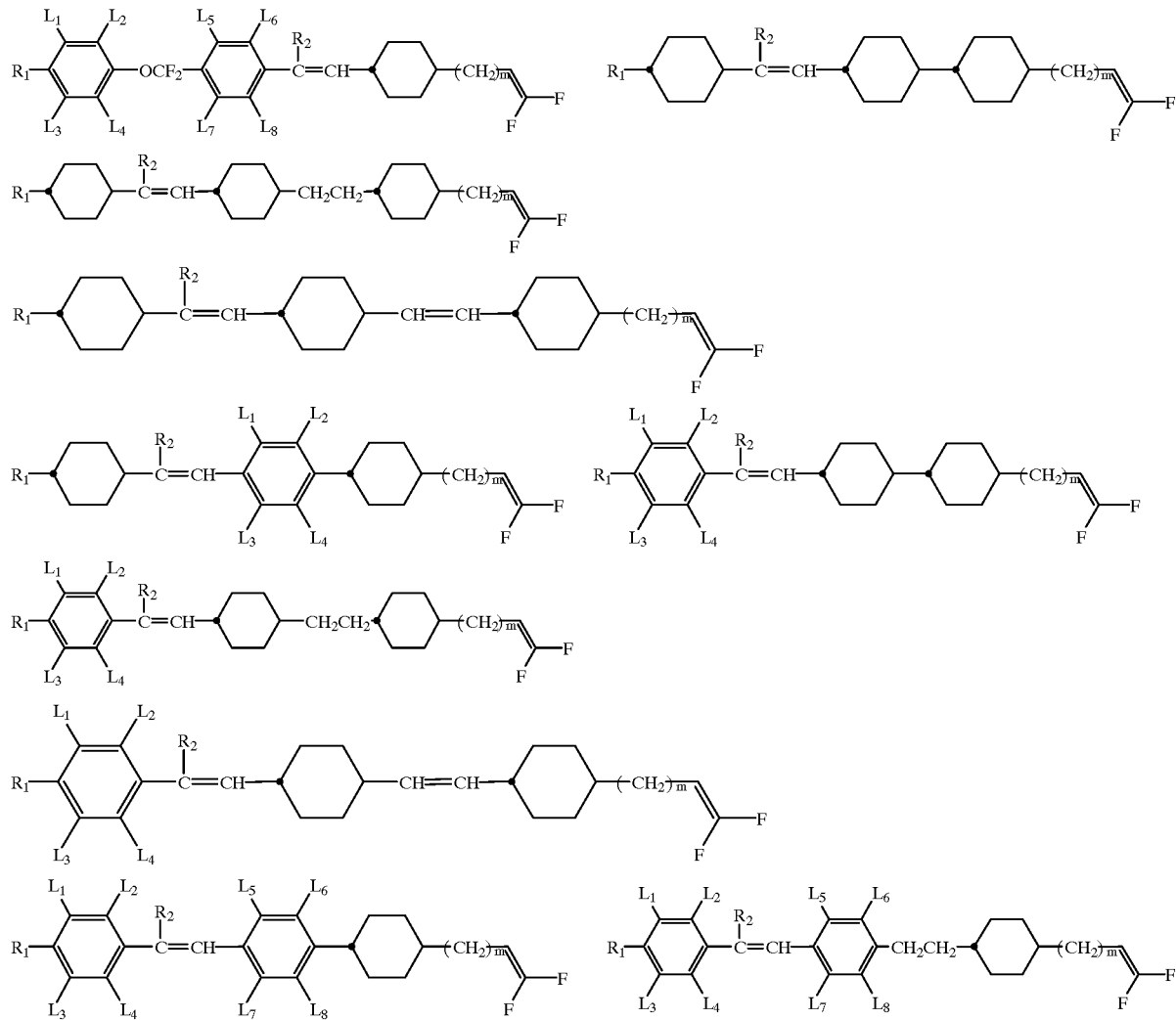

wherein $R_{11}$ $R_{21}$ m and $L_1$ to $L_{12}$ are as defined above.

The 22nd aspect of the present invention is directed to a fluorovinyl derivative compound represented by the general formula (1-4-7)

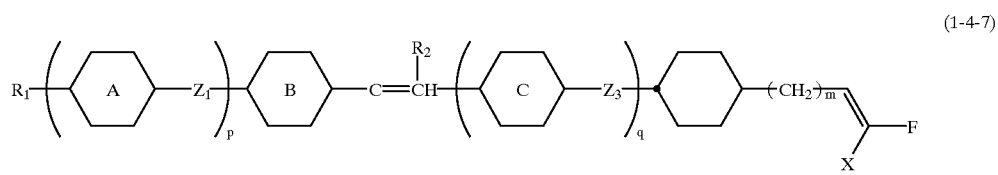

(1-4-7)

wherein $R_1$, X, m, $Z_1$, $Z_3$, p and q are as defined in the 1st aspect of the present invention; the rings A, B and C are each 1,4-cyclohexylene or 1,4-phenylene in which a hydrogen atom in the ring may be substituted by a halogen atom; and $R_2$ is an alkyl group having 1 to 5 carbon atoms.

Typical examples of the compound represented by the general formula (1-4-7) include compounds of the following formulae:

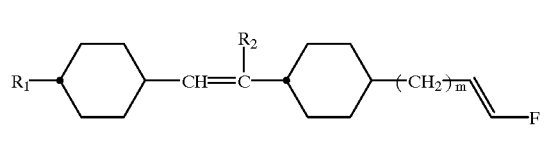
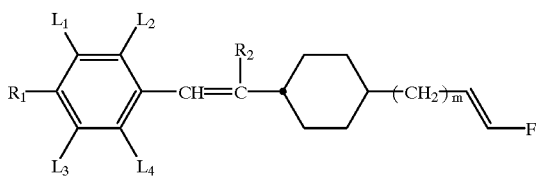
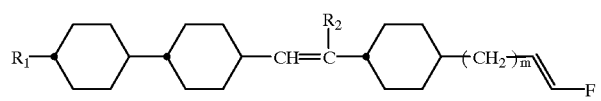
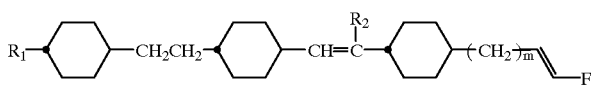
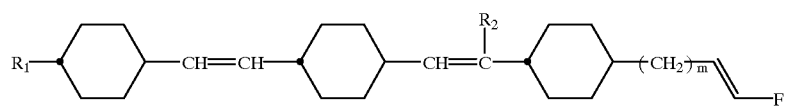
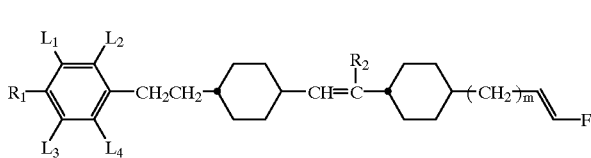
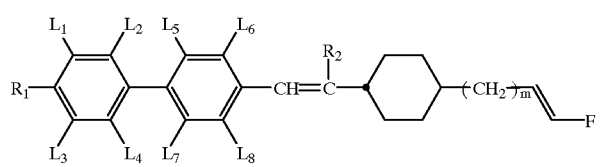
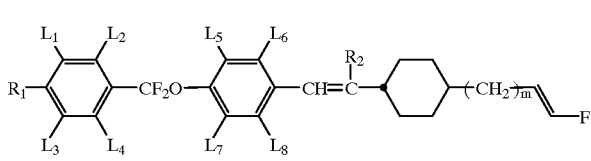
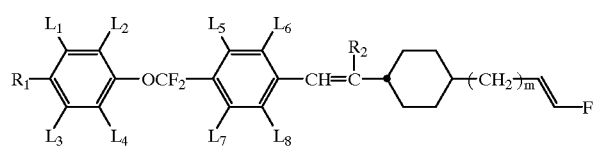
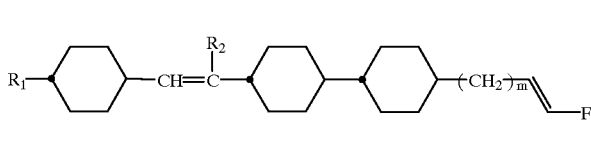
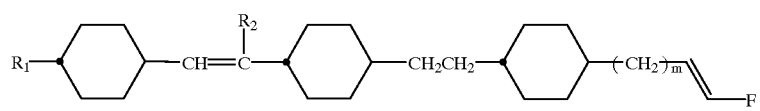
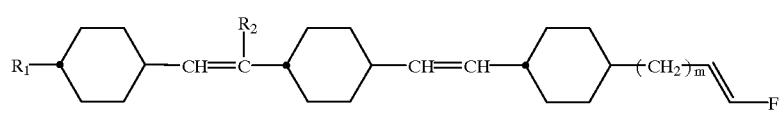
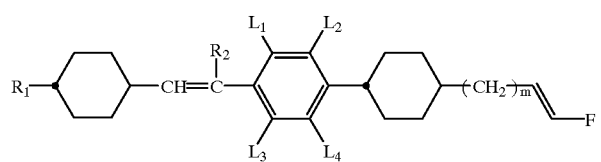
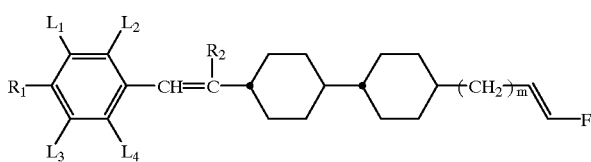
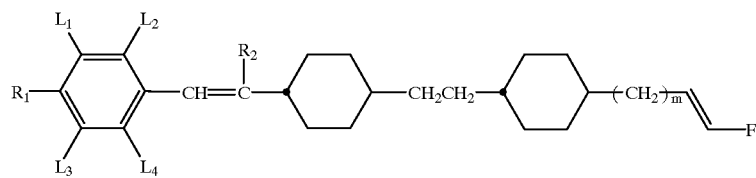
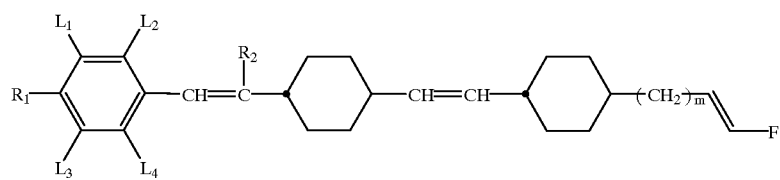

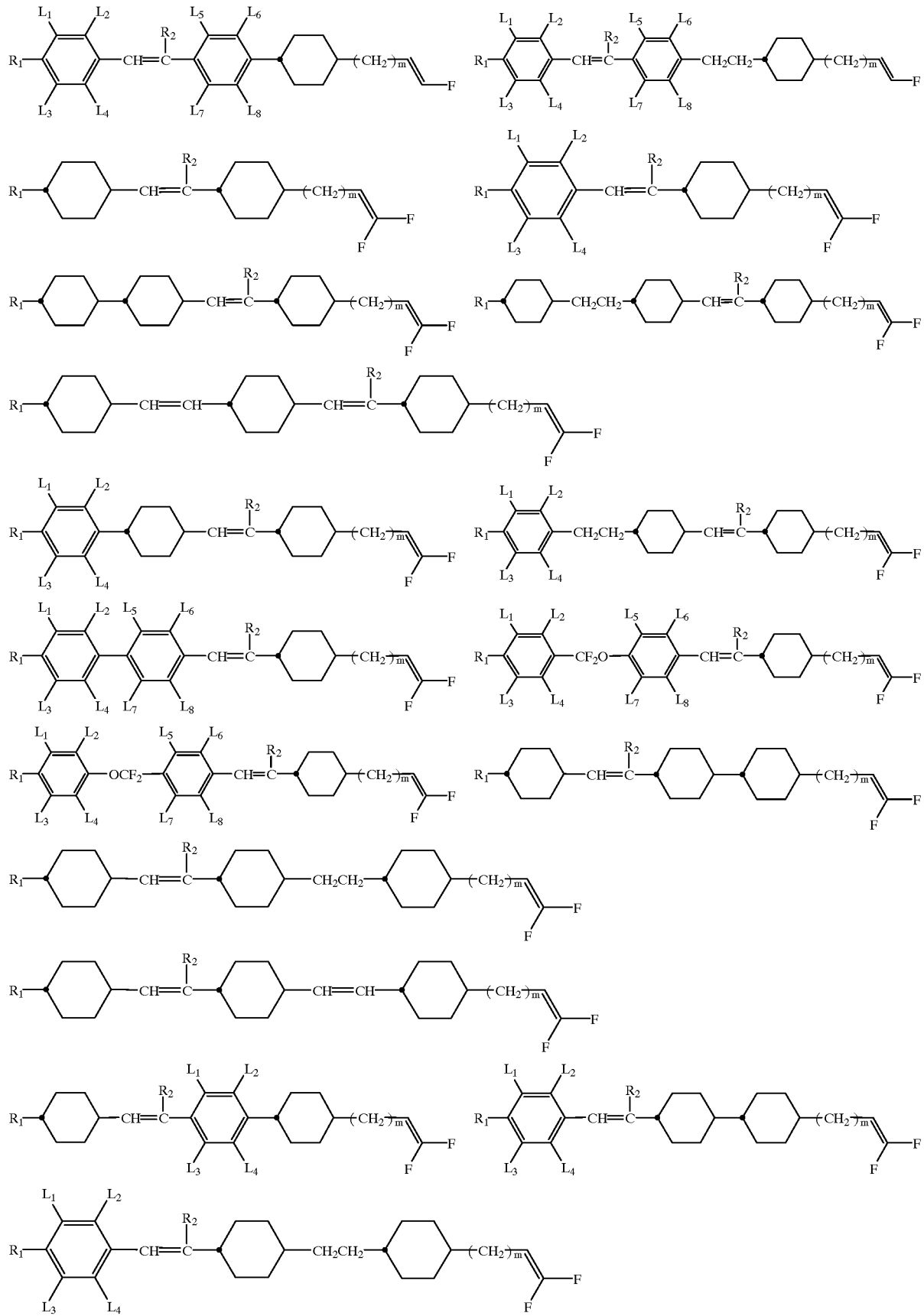

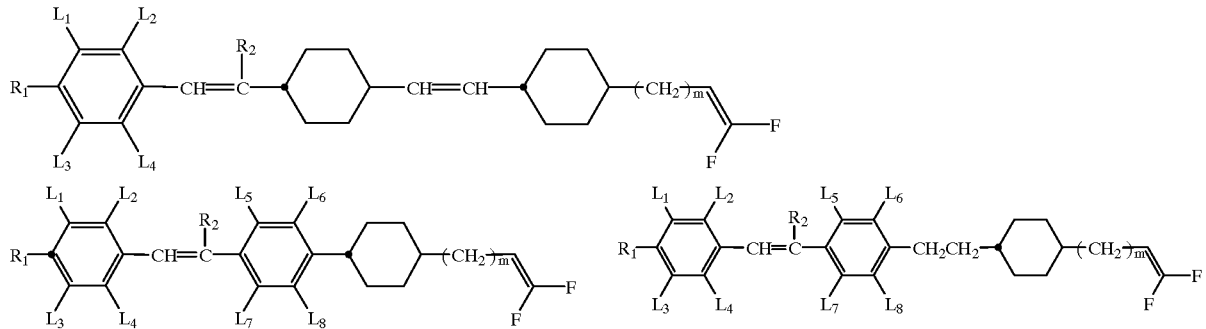

wherein $R_1$, $R_2$, m and $L_1$ to $L_{12}$ are as defined above.

The 23rd aspect of the present invention is directed to a liquid crystal composition which contains at least one of the liquid crystal compounds described in the 1st aspect to the 22nd aspect of the present invention.

The 24th aspect of the present invention is directed to a liquid crystal composition which contains, as a first component, at least one of the liquid crystal compounds described in the 1st aspect to the 22nd aspect of the present invention, and as a second component, at least one compound selected from the group consisting compounds of the general formulae (2), (3) and (4)

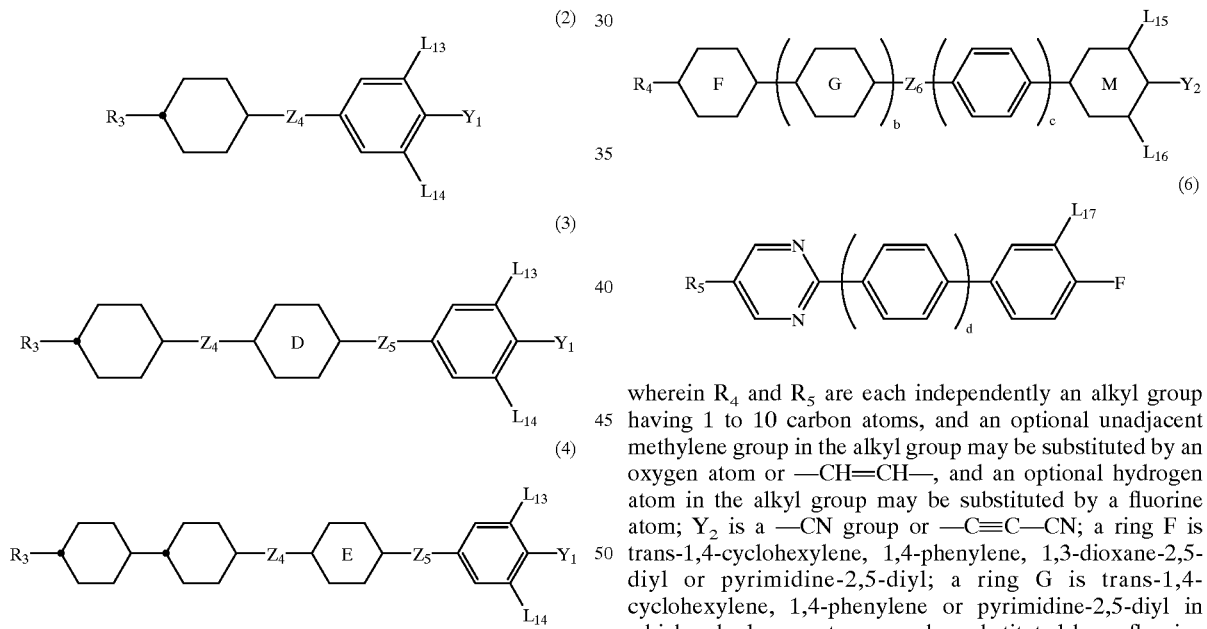

wherein $R_3$ is an alkyl group having 1 to 10 carbon atoms, and an optional unadjacent methylene group in the alkyl group may be substituted by an oxygen atom or —CH=CH—, and an optional hydrogen atom in the alkyl group may be substituted by a fluorine atom; $Y_1$ is a fluorine atom, a chlorine atom, $OCF_3$, $OCF_2H$, $CF_3$, $CF_2H$, $CFH_2$, $OCF_2CF_2H$ or $OCF_2CFHCF_3$; $L_{13}$ and $L_{14}$ are each independently a hydrogen atom or a fluorine atom; $Z_4$ and $Z_5$ are each independently a 1,2-ethylene group, a 1,4-butylene group, —COO—, —$CF_2O$—, —$OCF_2$—, —CH=CH— or a single bond; a ring D is trans-1,4-cyclohexylene, 1,3-dioxane-2,5-diyl or 1,4-phenylene in which a hydrogen atom may be substituted by a halogen atom; a ring E is trans-1,4-cyclohexylene or 1,4-phenylene in which a hydrogen atom may be substituted by a fluorine atom; and an atom in each formula may be substituted by its isotope.

The 25th aspect of the present invention is directed to a liquid crystal composition which contains, as a first component, at least one of the liquid crystal compounds described in the 1st aspect to the 22nd aspect of the present invention, and as a second component, at least one compound selected from the group consisting compounds of the general formulae (5) and (6)

wherein $R_4$ and $R_5$ are each independently an alkyl group having 1 to 10 carbon atoms, and an optional unadjacent methylene group in the alkyl group may be substituted by an oxygen atom or —CH=CH—, and an optional hydrogen atom in the alkyl group may be substituted by a fluorine atom; $Y_2$ is a —CN group or —C≡C—CN; a ring F is trans-1,4-cyclohexylene, 1,4-phenylene, 1,3-dioxane-2,5-diyl or pyrimidine-2,5-diyl; a ring G is trans-1,4-cyclohexylene, 1,4-phenylene or pyrimidine-2,5-diyl in which a hydrogen atom may be substituted by a fluorine atom; a ring M is trans-1,4-cyclohexylene or 1,4-phenylene; $Z_6$ is a 1,2-ethylene group, —COO— or a covalent bond; $L_{15}$, $L_{16}$ and $L_{17}$ are each independently a hydrogen atom or a fluorine atom; b, c and d are each independently 0 or 1; and an atom in each formula may be substituted by its isotope.

The 26th aspect of the present invention is directed to a liquid crystal composition which contains at least one of the liquid crystal compounds described in the 1st aspect to the 22nd aspect of the present invention as a first component, at least one compound selected from the group consisting compounds of the general formulae (2), (3) and (4) as a second component, and at least one compound selected from the group consisting compounds of the general formulae (7), (8) and (9) as a third component

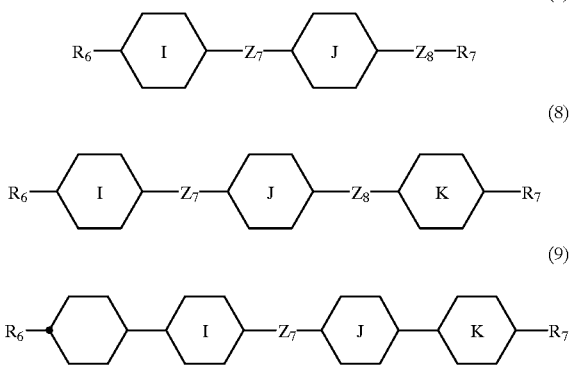

wherein $R_6$ and $R_7$ is each independently an alkyl group having 1 to 10 carbon atoms, and an optional unadjacent methylene group in the alkyl group may be substituted by an oxygen atom or —CH=CH—, and an optional hydrogen atom in the alkyl group may be substituted by a fluorine atom; rings I, J and K are each independently trans-1,4-cyclohexylene, pyrimidine-2,5-diyl or 1,4-phenylene in which a hydrogen atom may be substituted by a fluorine atom; $Z_7$ and $Z_8$ are each independently —C≡C—, —COO—, —CH$_2$CH$_2$—, —CH=CH— or a single bond; and an atom in each formula may be substituted by its isotope.

The 27th aspect of the present invention is directed to a liquid crystal composition which contains at least one of the liquid crystal compounds described in the 1st aspect to the 22nd aspect of the present invention as a first component, at least one compound selected from the group consisting compounds of the general formulae (5) and (6) as a second component, and at least one compound selected from the group consisting compounds of the general formulae (7), (8) and (9) as a third component.

The 28th aspect of the present invention is directed to a liquid crystal composition which contains at least one of the liquid crystal compounds described in the 1st aspect to the 22nd aspect of the present invention as a first component, at least one compound selected from the group consisting compounds of the general formulae (2), (3) and (4) as a second component, at least one compound selected from the group consisting compounds of the general formulae (5) and (6) as a third component, and at least one compound selected from the group consisting compounds of the general formulae (7), (8) and (9) as a fourth component.

The 29th aspect of the present invention is directed to a liquid crystal composition which contains a liquid crystal composition described in any one of the 23rd aspect to the 28th aspect of the present invention and at least one optically active compound.

The 30th aspect of the present invention is directed to a liquid crystal display device constituted by the use of a liquid crystal composition described in any one of the 23rd aspect to the 29th aspect of the present invention.

A novel liquid crystal fluorovinyl derivative compound of the present invention has particularly steep threshold properties, a low viscosity, a good compatibility with another liquid crystal compound and a proper optical anisotropy value. Furthermore, a novel liquid crystal composition and a liquid crystal display device constituted by using this compound have the above excellent characteristics.

BEST MODE FOR CARRYING OUT THE INVENTION

Next, the present invention will be described in detail.

In the present invention, $R_1$ in the general formula (1) is an alkyl group having 1 to 18 carbon atoms in which a methylene group may be substituted by an oxygen atom, a sulfur atom, —CH=CH— or —C≡C— and a hydrogen atom may be substituted by a halogen atom or a cyano group. Typical examples of the alkyl group include an alkyl group, alkenyl group, alkynyl group, alkadienyl group, alkoxy group, alkoxyalkyl group, alkenyloxy group, alkynyloxy group, haloalkyl group and cyano group-substituted alkyl group.

More typical examples of the alkyl group include a methyl group, ethyl group, propyl group, butyl group, pentyl group, vinyl group, 1-propenyl group, 1-butenyl group, 1-pentenyl group, 3-butenyl group, 3-pentenyl group, 1-propynyl group, 1-butynyl group, 3-pentynyl group, 1,3-butadienyl group, 1,4-pentadienyl group, 1,5-hexadienyl group, 1,5-heptadienyl group, methoxy group, ethoxy group, propoxy group, butoxy group, pentoxy group, methoxymethyl group, ethoxymethyl group, propoxymethyl group, butoxymethyl group, methoxyethyl group, propoxymethyl group, methoxypropyl group, ethoxypropyl group, allyloxy group, 3-butenyloxy group, 2-butynyloxy group, 3-pentynyloxy group, fluoromethyl group, 2-fluoroethyl group, 3-fluoropropyl group, 4-fluorobutyl group, 5-fluoropentyl group, 2-fluorobutyl group, 2-fluoropentyl group, 2,2-difluorobutyl group, 2,2-difluoropentyl group, 3-fluorobutyl group, 3-fluoropentyl group, 3,3-difluorobutyl group, 3,3-difluoropentyl group, 4-fluoropentyl group, 4,4-difluoropentyl group, cyanomethyl group, 2-cyanoethyl group, 3-cyanopropyl group, 4-cyanobutyl group and 5-cyanopentyl group.

In the general formula (1) of the present invention, rings A, B and C are each 1,4-cyclohexylene, 1,4-cyclohexenylene, 1,4-phenylene, 1,3-dioxane-2,5-diyl, pyridine-2,5-diyl or pyrimidine-2,5-diyl in which a hydrogen atom in the ring may be substituted by a halogen atom. In the case that the low-viscosity liquid crystal is required, the rings A, B and C are each 1,4-cyclohexylene, or 1,4-phenylene or 1,3-dioxane-2,5-diyl in which a hydrogen atom in the ring may be substituted by a halogen atom.

$Z_1$, $Z_2$ and $Z_3$ are each independently a single bond, —CH$_2$CH$_2$—, —CH=CH—, —CH$_2$O—, —OCH$_2$—, —(CH$_2$)$_4$—, —(CH$_2$)$_3$—O—, —O—(CH$_2$)$_3$—, —(CH$_2$)$_2$—CH=CH—, —CH=CH—(CH$_2$)$_2$—, —CF$_2$O—, —OCF$_2$—, —CR$_2$=CH—, —CH=CR$_2$— or —CF=CF—, and $R_2$ is an alkyl group having 1 to 5 carbon atoms.

In the case that the low-viscosity liquid crystal is required, $Z_1$, $Z_2$ and $Z_3$ are each preferably a single bond, —CH$_2$CH$_2$—, —CH=CH—, —(CH$_2$)$_2$—CH=CH—, —CH=CH—(CH$_2$)$_2$—, —CF$_2$O—, —OCF$_2$— or —CF=CF—, more preferably a single bond, —CH=CH—, —CF$_2$O—, —OCF$_2$— or —CF=CF—.

In the case that the liquid crystal having a large optical anisotropy is required, $Z_1$, $Z_2$ and $Z_3$ are each preferably —CH=CH—, —(CH$_2$)$_2$—CH=CH—, —CH=CH—(CH$_2$)$_2$—, —CR$_2$=CH—, —CH=CR$_2$— or —CF=CF—.

In the formula (1), m is an integer of 0 to 5. In the case that the low-viscosity liquid crystal is required, m is preferably a small value. Alternatively, in the case that a good liquid crystalline property (a wide nematic phase temperature range) and a high elastic constant ratio ($K_{33}/K_{11}$) are required, m is preferably in the range of 0 to 2.

The compound of the general formula (1) [hereinafter referred to as "the compound (1)"] has a much higher elastic constant ratio ($K_{33}/_{11}$) as compared with conventional compounds, and the liquid crystal composition using the compound (1) shows steep threshold properties. Furthermore, in the compound of the general formula (1), a dependency of the constant ratio on a temperature, particularly in a low temperature range, the dependency of the constant ratio on the temperature is far lower than in the conventional liquid crystal compounds.

The compound (1) has a high compatibility with another liquid crystal compound or another liquid crystal composition. The liquid crystal composition using the compound (1) can keep the nematic phase even at a low temperature (e.g., −20° C. which is practically required).

The compound (1) exhibits a low viscosity, and so when the liquid crystal composition is prepared by the use of this compound (1), the viscosity of the whole composition does not increase, even if the content of the compound (1) is high. Furthermore, the dependency of the viscosity on the temperature, particularly at the low temperature, the dependency of the viscosity on the temperature is extremely low. When this low-viscosity liquid crystal compound is used for the display device, the liquid crystal composition having a high-speed response can be prepared.

The compound (1) has a suitable optical anisotropy value and a suitable dielectric anisotropy value.

The compound (1) is very chemically stable, and the liquid crystal composition in which this compound (1) is used has a very high specific resistance and voltage holding ratio. This compound (1) is also remarkably stable to external factors such as ultraviolet light and heat, and hence it shows a chemical stability which is satisfactory as a constitutional element of the practical liquid crystal composition.

An optional constitutional element of the compound (1) may be substituted by a corresponding isotope, because even when such a substitution is made, the characteristics of the compound (1) does not change.

The compound of the present invention is particularly suitable for the preparation of the liquid crystal composition for STN, but it can also be suitably applied to other uses. For example, this compound can be utilized as a liquid crystal compound for TN, a liquid crystal compound for a guest-host mode, a liquid crystal compound for a polymer dispersion type liquid crystal device, a liquid crystal compound for a dynamic scattering mode, a liquid crystal compound for an active matrix, a compound for a ferroelectric liquid crystal, a compound for an anti-ferroelectric liquid crystal and the like.

A liquid crystal composition of the present invention contains 0.1 to 99.9% by weight, preferably 1 to 50% by weight, more preferably 3 to 20% by weight of one or more of the compounds (1), and this composition expresses excellent characteristics.

Another liquid crystal composition which can be provided by the present invention contains at least one of the compounds (1) at a first component and another compound optionally selected from the group consisting of compounds represented by the general formulae (2) to (9) in compliance with a purpose of the liquid crystal composition.

Preferable examples of the compounds represented by the general formulae (2) to (4) include the following compounds:

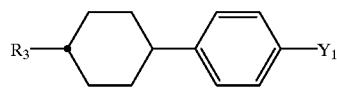

(2-1)

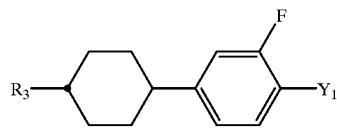

(2-2)

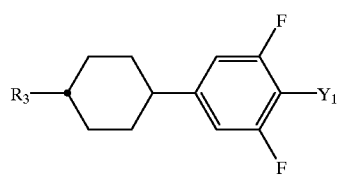

(2-3)

(2-4)

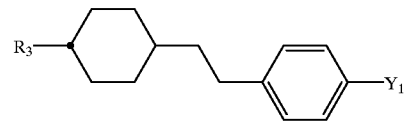

(2-5)

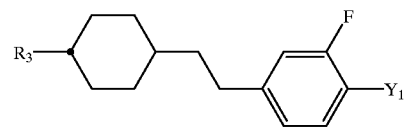

(2-6)

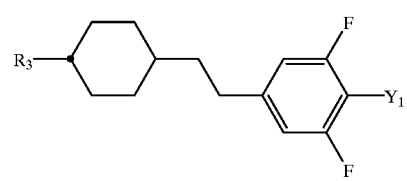

(2-7)

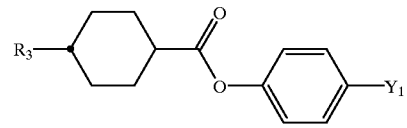

(2-8)

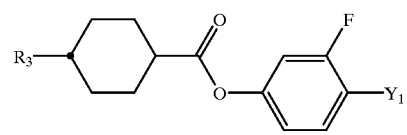

(2-9)

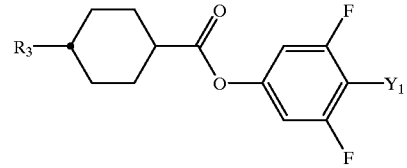

(3-1)
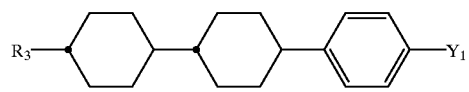
(3-2)
(3-3)
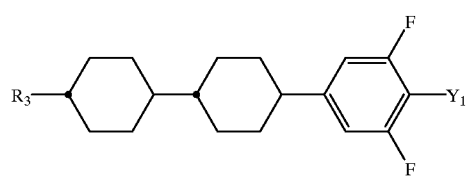
(3-4)
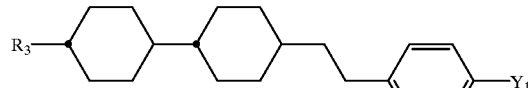
(3-5)
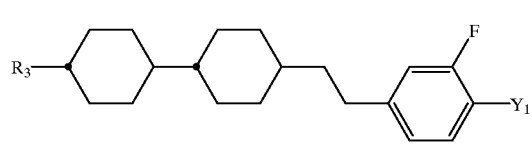
(3-6)
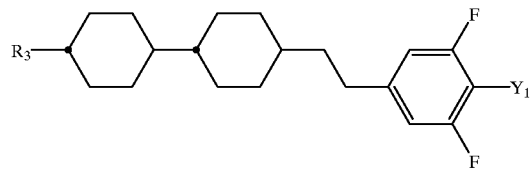
(3-7)
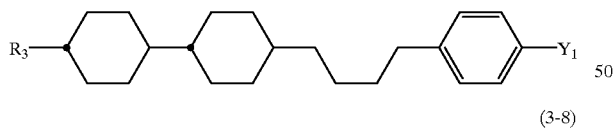
(3-8)
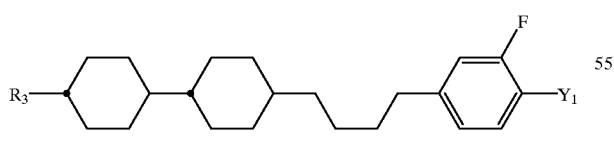
(3-9)
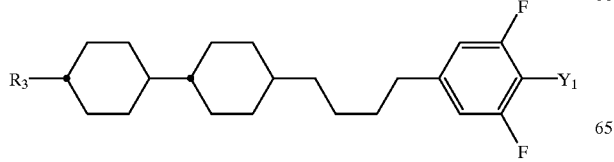
(3-10)
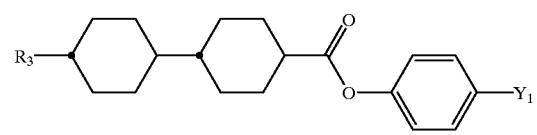
(3-11)
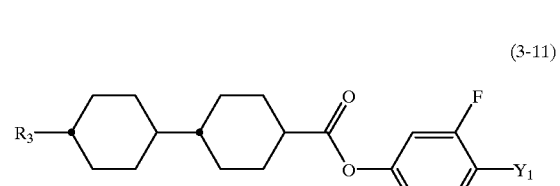
(3-12)
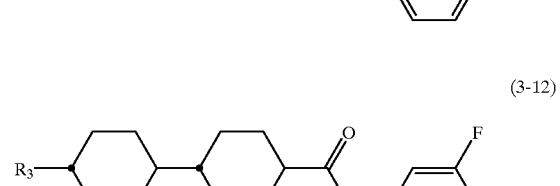
(3-13)
(3-14)
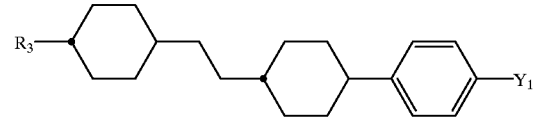
(3-15)
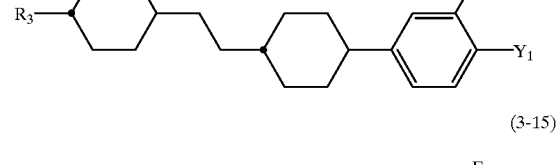
(3-16)
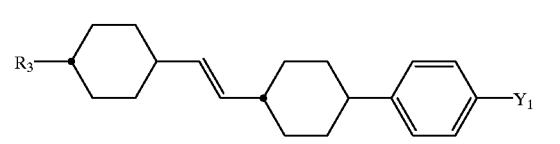
(3-17)
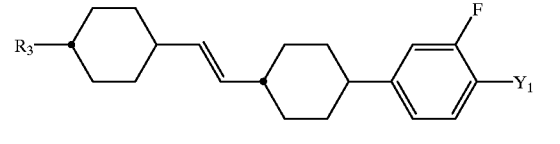

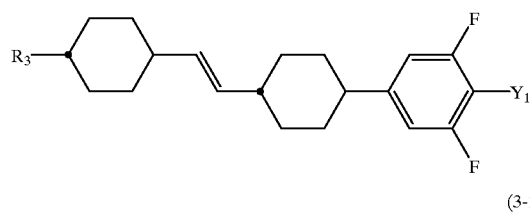 (3-18)
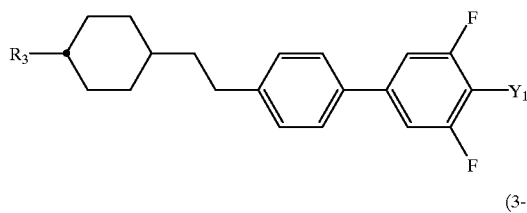 (3-27)
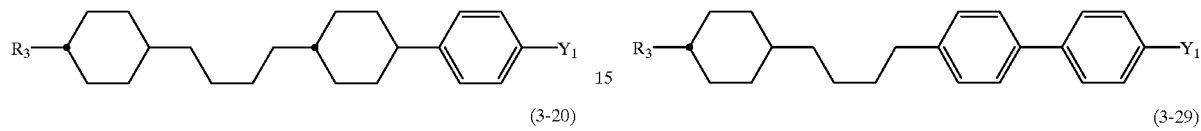
(3-19)
(3-28)
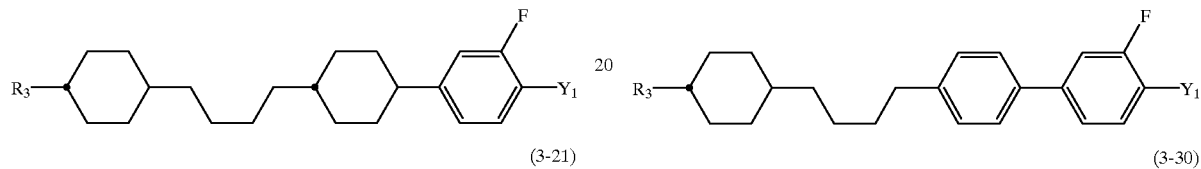
(3-20)
(3-29)
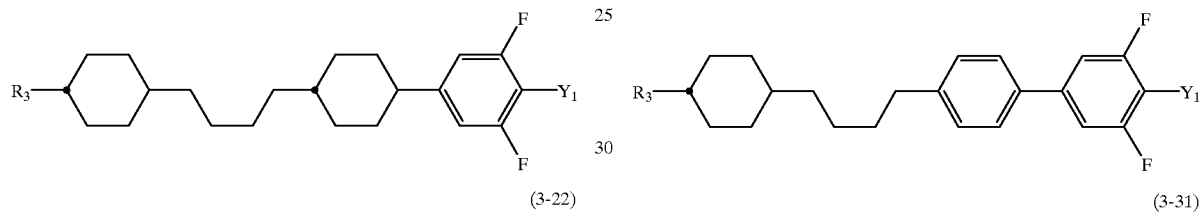
(3-21)
(3-30)
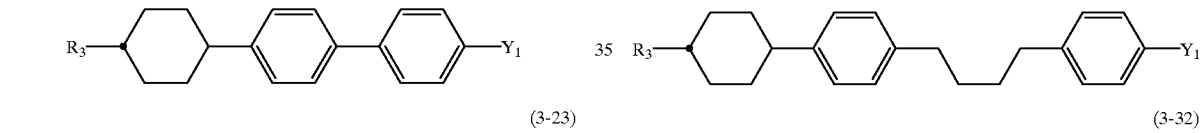
(3-22)
(3-31)
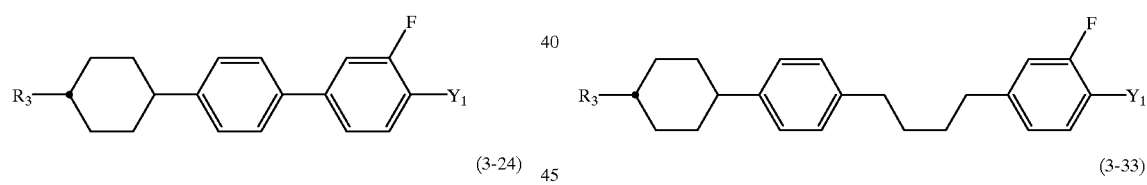
(3-23)
(3-32)
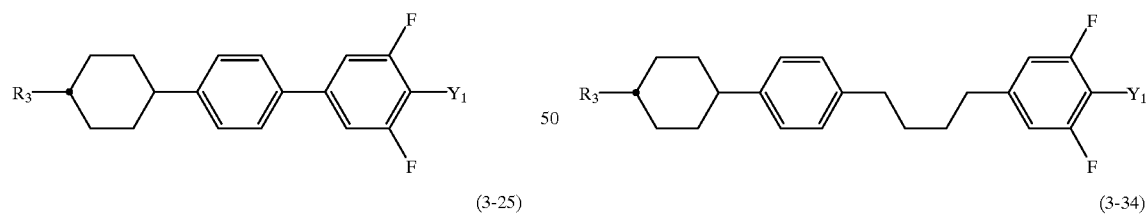
(3-24)
(3-33)
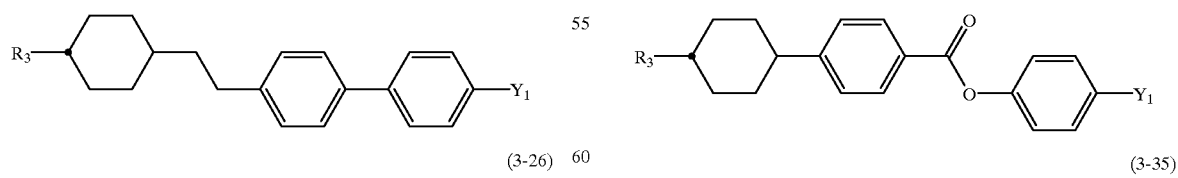
(3-25)
(3-34)
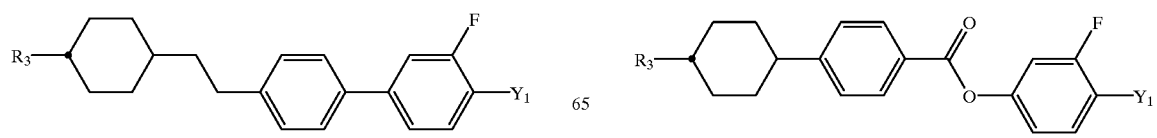
(3-26)
(3-35)

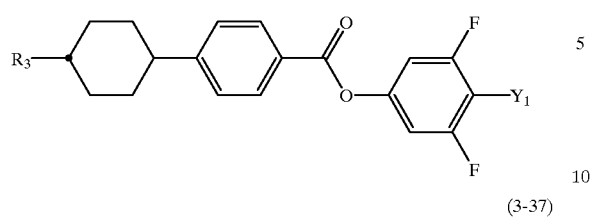
(3-36)
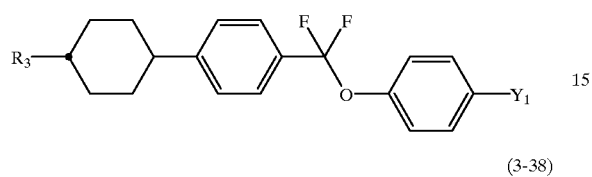
(3-37)
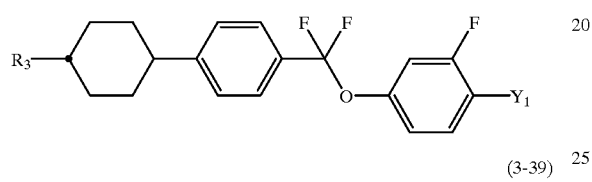
(3-38)
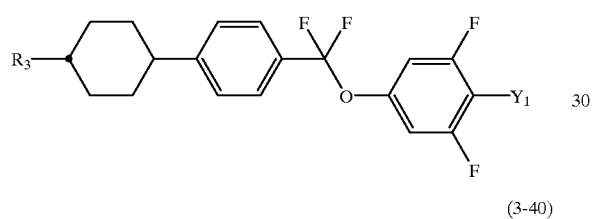
(3-39)
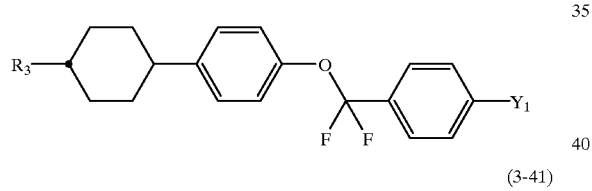
(3-40)
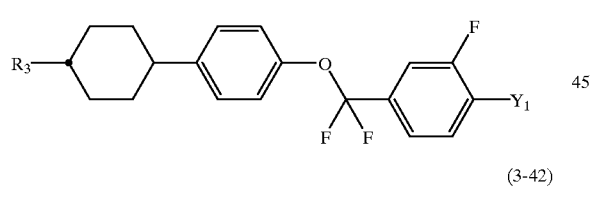
(3-41)
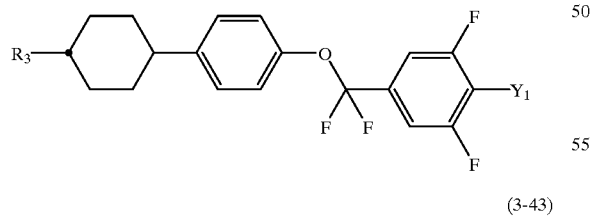
(3-42)
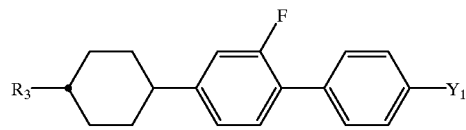
(3-43)
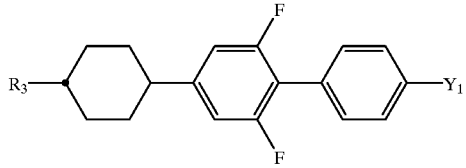
(3-44)
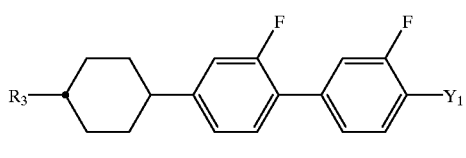
(3-45)
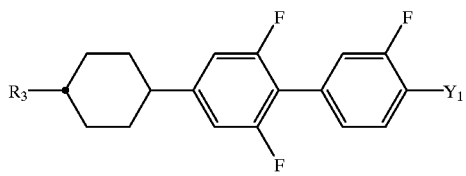
(3-46)
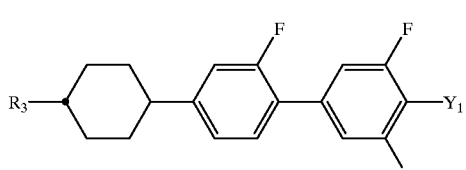
(3-47)
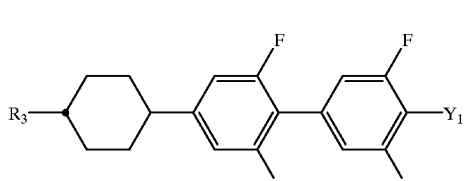
(3-48)
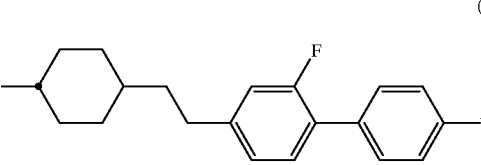
(3-49)
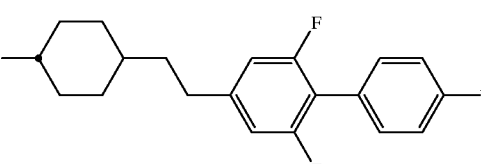
(3-50)
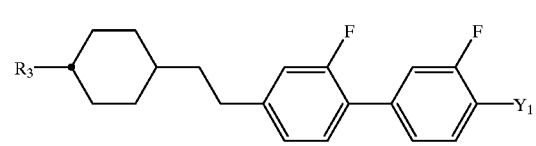
(3-51)

(3-52)
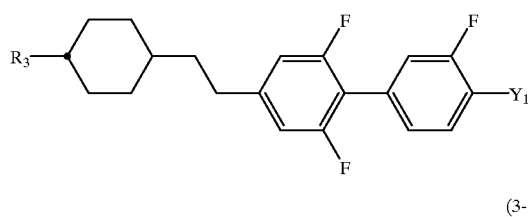
(3-53)
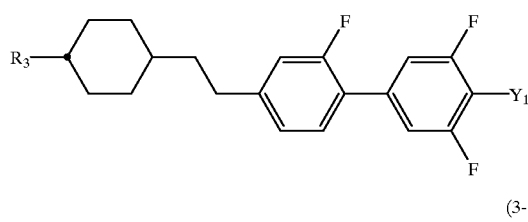
(3-54)
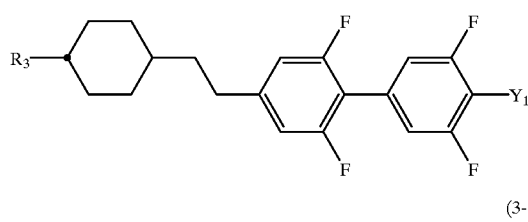
(3-55)
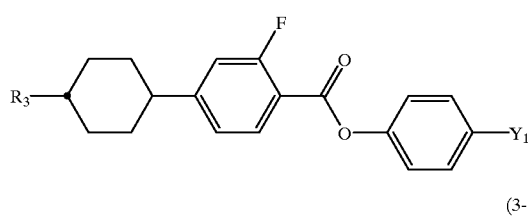
(3-56)
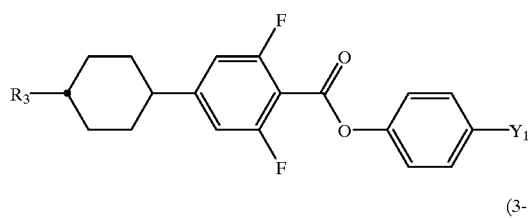
(3-57)
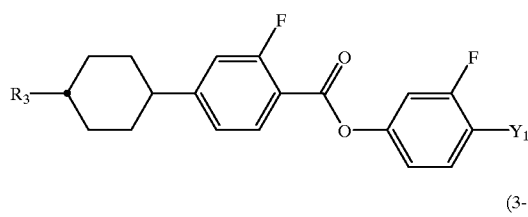
(3-58)
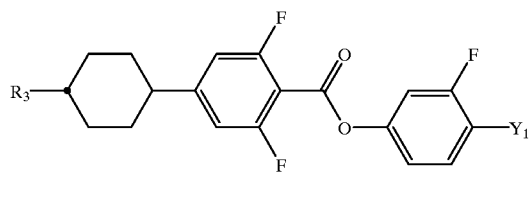
(3-59)
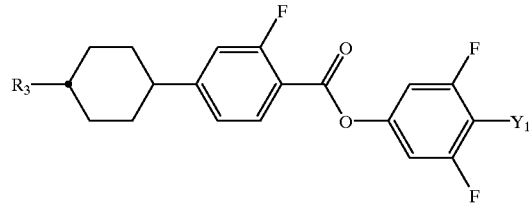
(3-60)
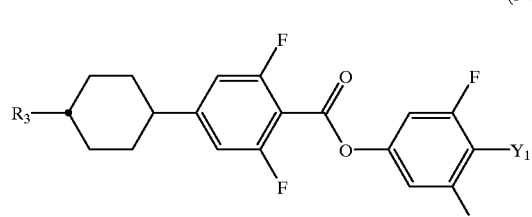
(3-61)
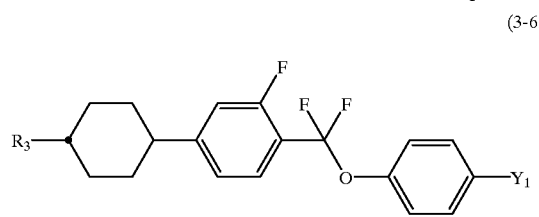
(3-62)
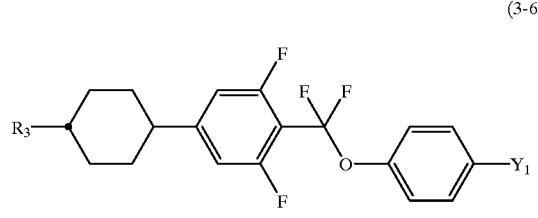
(3-63)
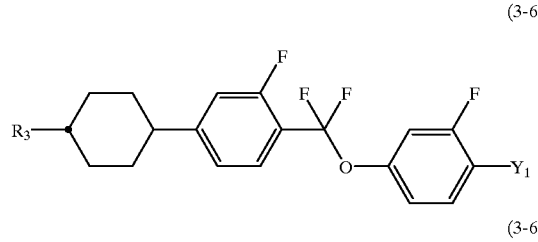
(3-64)
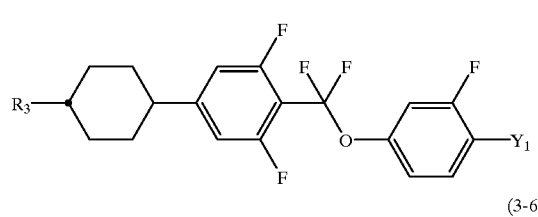
(3-65)
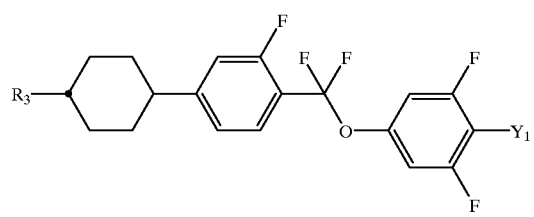

(3-66)
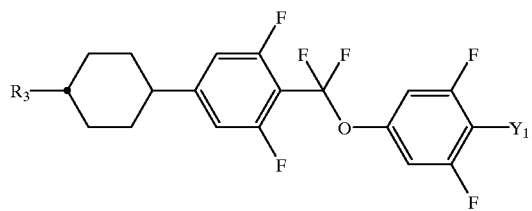
(3-67)
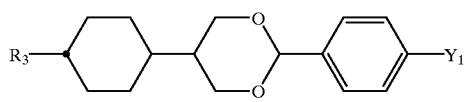
(3-68)
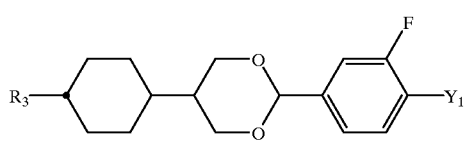
(3-69)
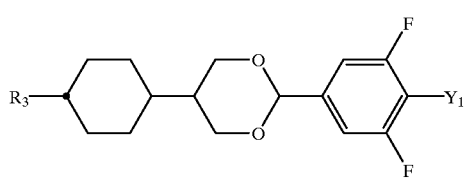
(4-1)
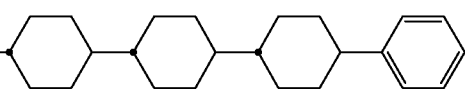
(4-2)
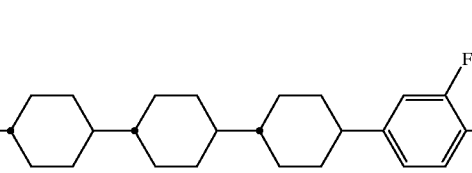
(4-3)
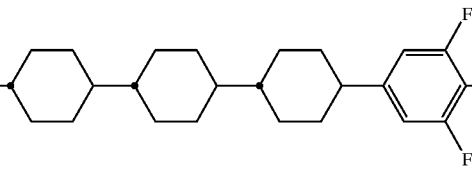
(4-4)
(4-5)
(4-6)
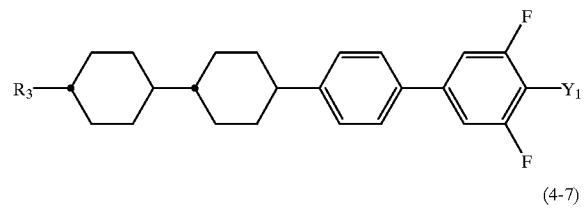
(4-7)
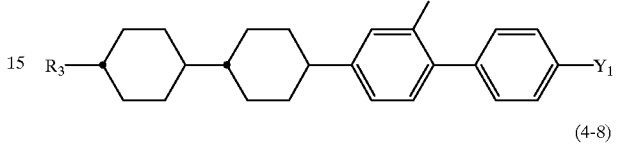
(4-8)
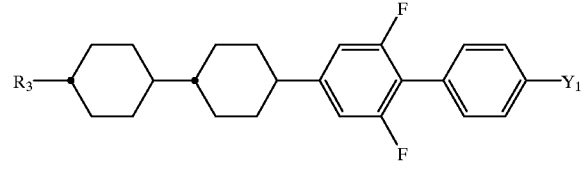
(4-9)
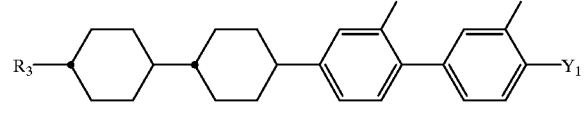
(4-10)
(4-11)
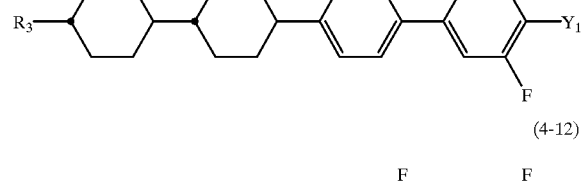
(4-12)
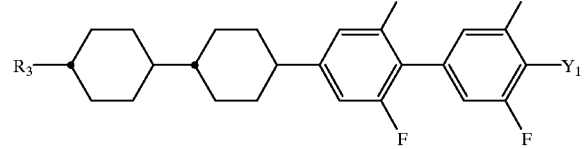
(4-13)
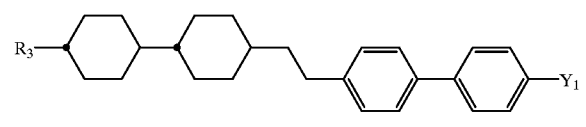

(4-14)
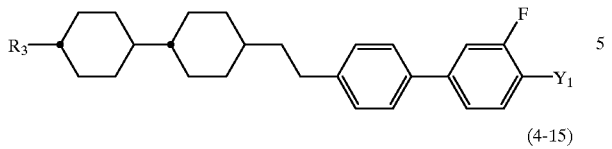

(4-15)
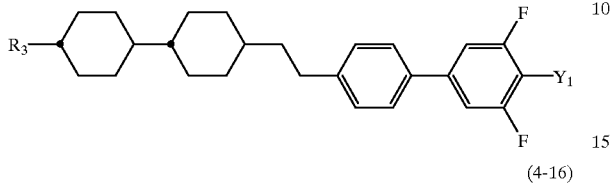

(4-16)
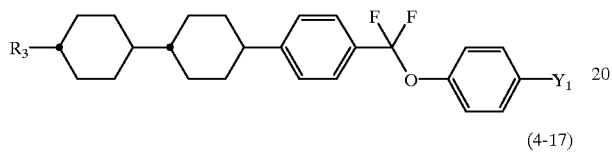

(4-17)
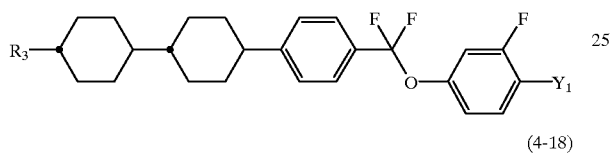

(4-18)
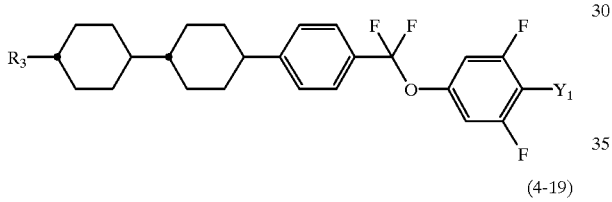

(4-19)
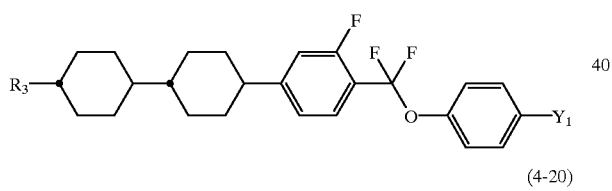

(4-20)
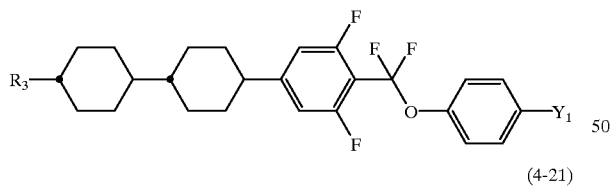

(4-21)
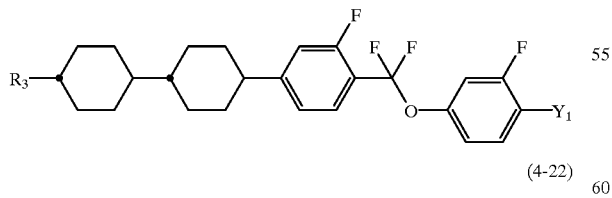

(4-22)
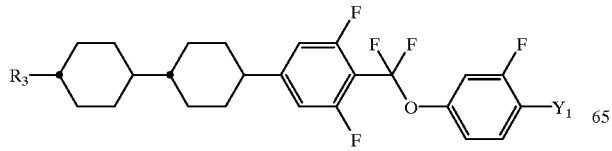

(4-23)
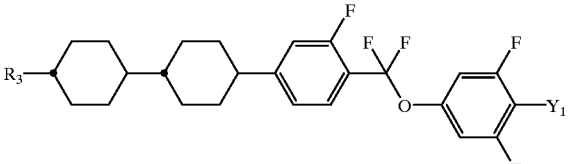

(4-24)
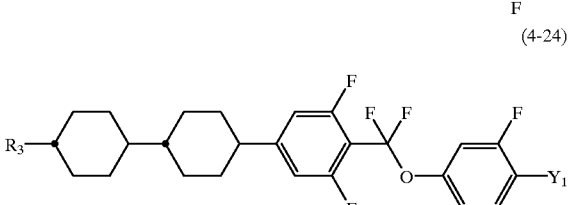

wherein $R_3$ and $Y_1$ are as defined above.

The compounds represented by the general formulae (2) to (4) have posidielectric anisotropy values, and they are essential to prepare the liquid crystal composition for TFT (AM-LCD) in which highly reliable characteristics such as an excellent thermal stability and chemical stability as well as a high voltage holding ratio (or a high specific resistance) are required.

In the case that the liquid crystal composition for TFT is prepared, the amount of any compound of the general formulae (2) to (4) to be used is in the range of 1 to 99% by weight, preferably 10 to 97% by weight, more preferably 40 to 95% by weight with respect to the total weight of the liquid crystal composition. In preparing the liquid crystal composition for TFT, any of the compounds of the general formulae (7) to (9) may be used. Also in preparing the liquid crystal composition for an STN display system or a TN display system, any of the compounds of the general formulae (2) to (4) may be used. In this case, the amount of any compound of the general formulae (2) to (4) is preferably 50% by weight or less, because the compound has a less effect of decreasing the threshold voltage of the liquid crystal composition, as compared with the compounds of the general formulae (5) and (6).

Preferable examples of the compounds represented by the general formulae (5) to (7) include the following compounds:

(5-1)
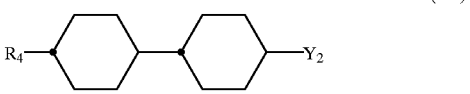

(5-2)
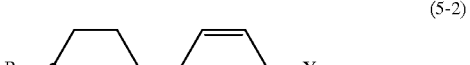

(5-3)

(5-4) 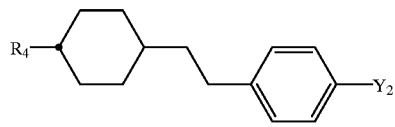
(5-5) 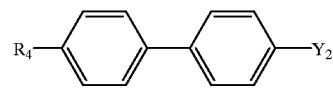
(5-6) 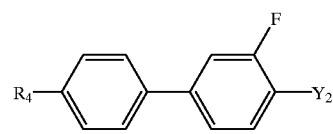
(5-7) 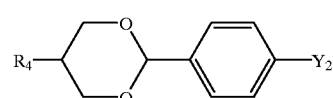
(5-8) 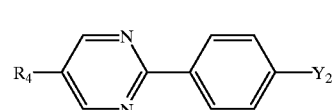
(5-9) 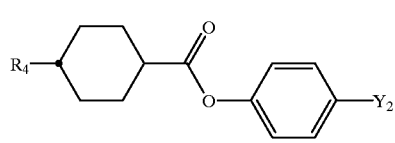
(5-10) 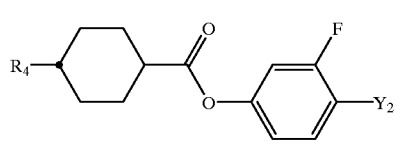
(5-11) 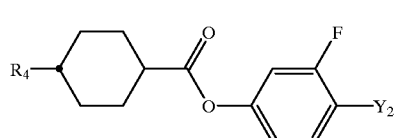
(5-12) 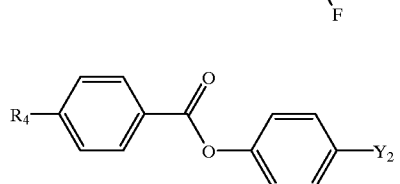
(5-13) 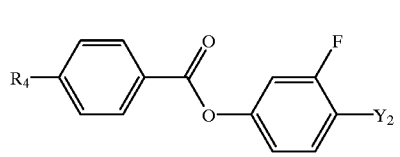
(5-14) 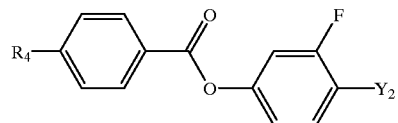
(5-15) 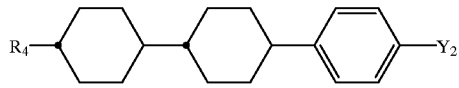
(5-16) 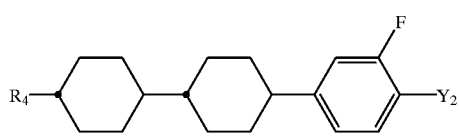
(5-17) 
(5-18) 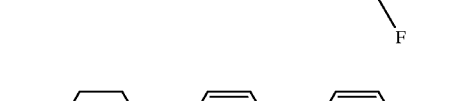
(5-19) 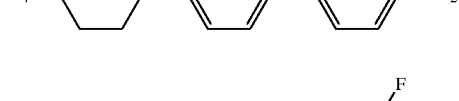
(5-20) 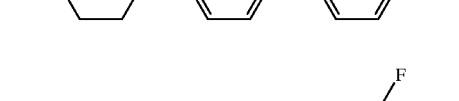
(5-21) 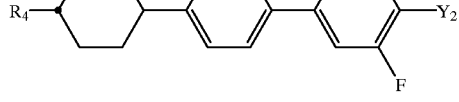
(5-22) 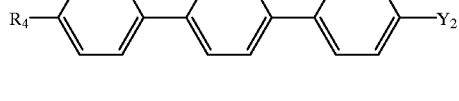
(5-23) 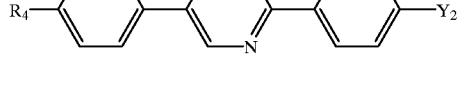

(5-24) 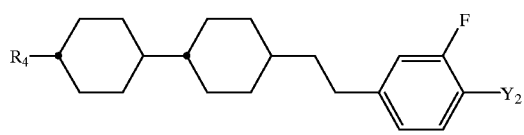
(5-25) 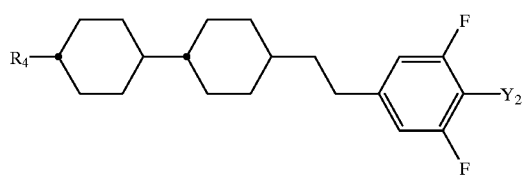
(5-26) 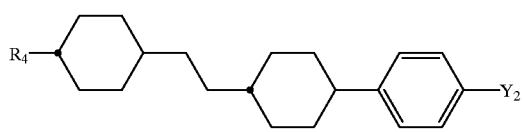
(5-27) 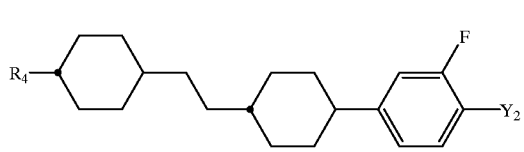
(5-28) 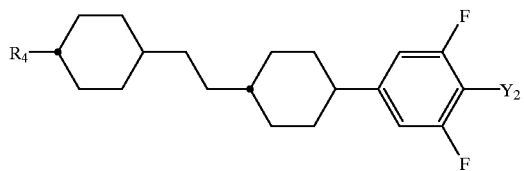
(5-29) 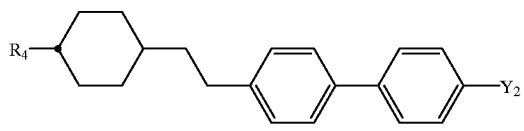
(5-30) 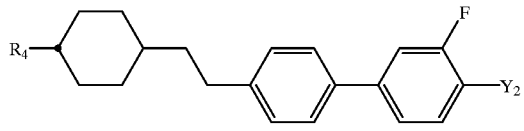
(5-31) 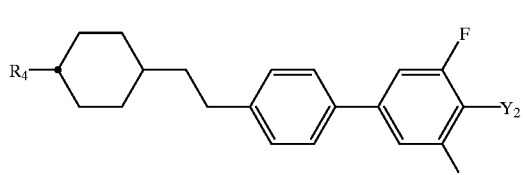
(5-32) 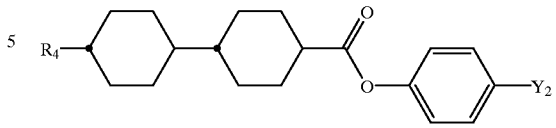
(5-33) 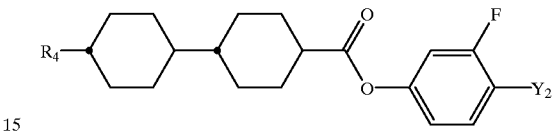
(5-34) 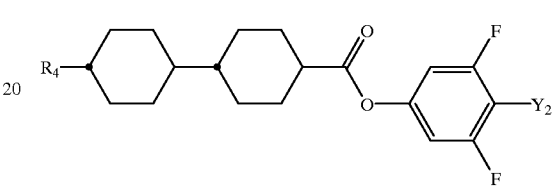
(5-35) 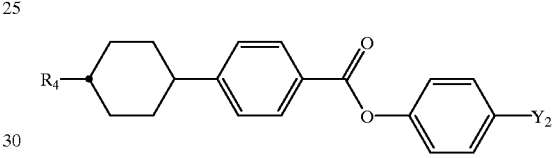
(5-36) 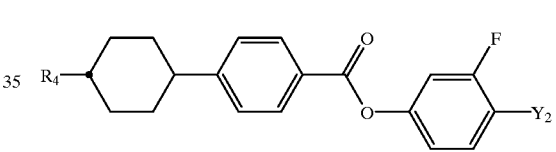
(5-37) 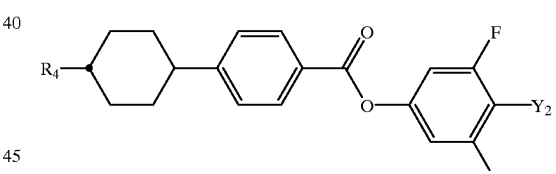
(5-38) 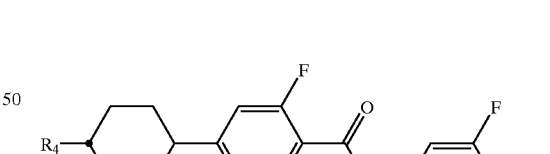
(5-39) 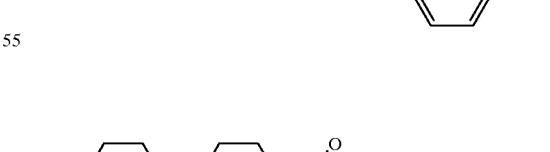

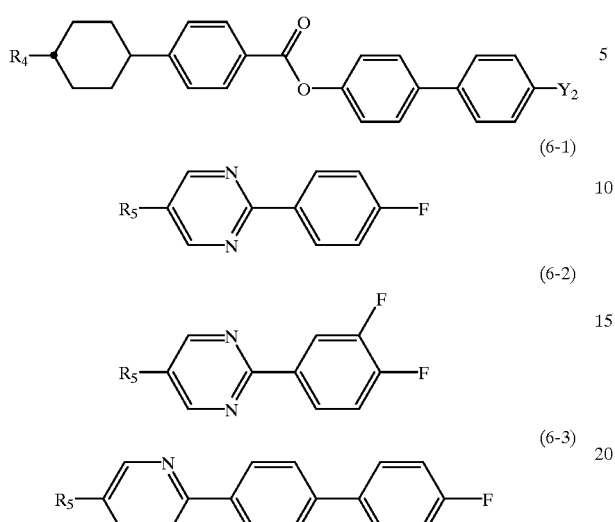

wherein $R_4$, $R_5$ and $Y_2$ are as defined above.

The compounds represented by the general formulae (5) and (6) have positive and large dielectric anisotropy values, and they can be used for the purpose of decreasing the threshold voltage. Furthermore, they can also be used for the purpose of the enlargement of a nematic range such as the adjustment of the optical anisotropy value, the rise of a clearing point or the like. Alternatively, they can also be used in order to improve the steepness of the threshold voltage of the liquid crystal composition for the STN display system or the TN display system.

The compounds of the general formulae (5) and (6) are essential to prepare the liquid crystal composition for the STN display system or the TN display system.

If the amount of the compound of the general formula (5) or (6) is increased, the threshold voltage of the liquid crystal composition decreases and the viscosity increases. Therefore, it is advantageous that the largest possible amount of the compound having the formula (5) or (6) is used in the range in which the required viscosity of the liquid crystal composition is met, because such a constitution permits the drive of the display device at a low voltage.

In the case that the liquid crystal composition for the STN display system or the TN display system is prepared, the amount of the compound of the general formula (5) or (6) to be used is in the range of 0.1 to 99.0% by weight, preferably 10 to 97% by weight, more preferably 40 to 95% by weight with respect to the total weight of the liquid crystal composition.

Preferable examples of the compounds represented by the general formulae (7) to (9) include the following compounds:

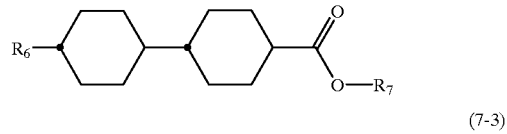

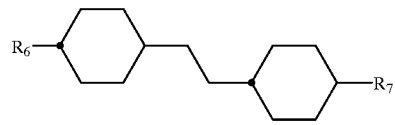

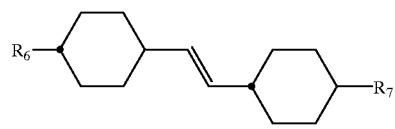

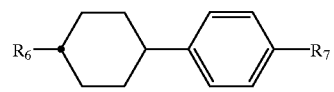

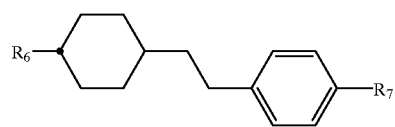

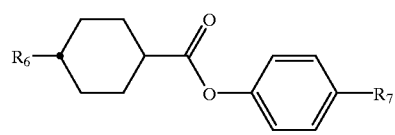

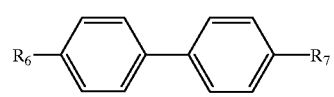

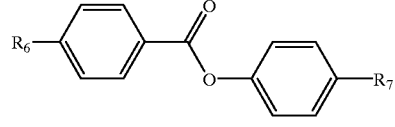

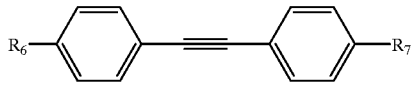

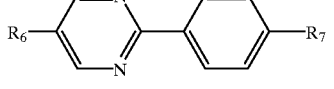

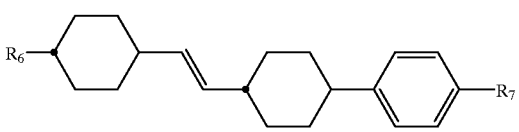

(8-3) 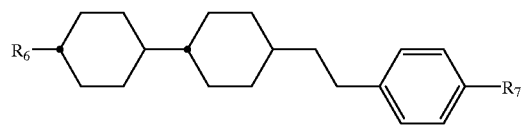
(8-4) 
(8-5) 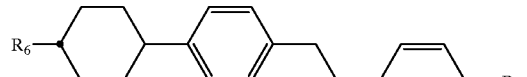
(8-6) 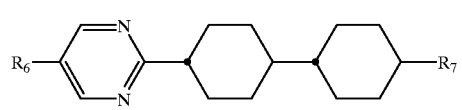
(8-7) 
(8-8) 
(8-9) 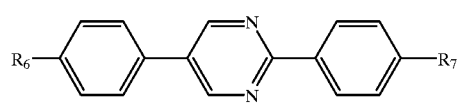
(8-10) 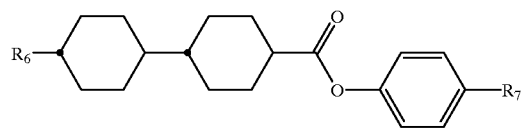
(8-11) 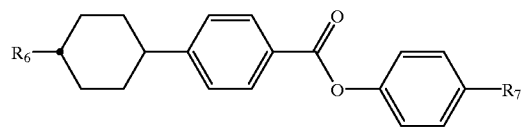
(8-12) 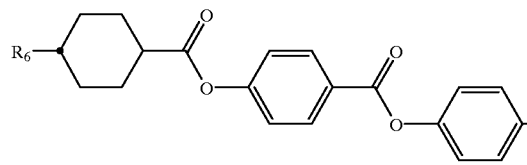
(8-13) 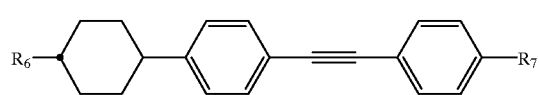
(8-14) 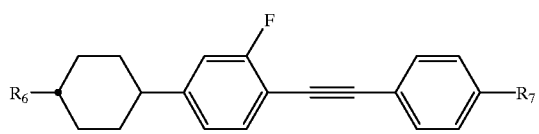
(8-15) 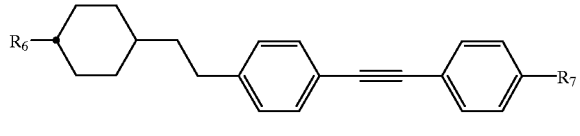
(8-16) 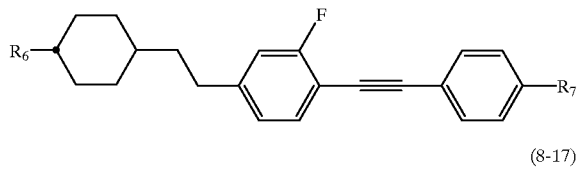
(8-17) 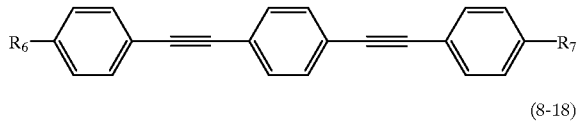
(8-18) 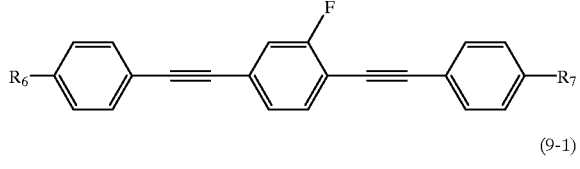
(9-1) 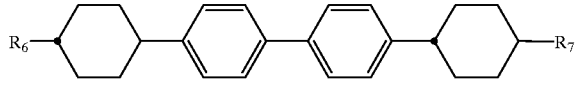
(9-2) 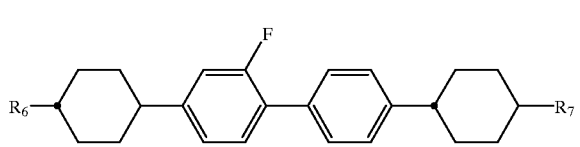
(9-3) 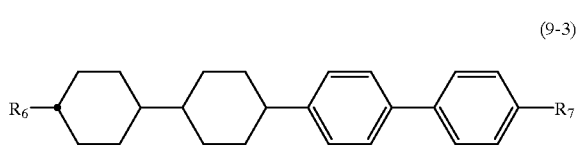
(9-4) 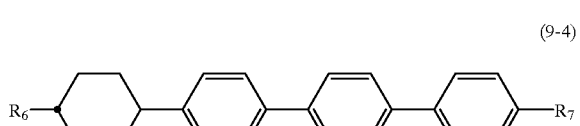
(9-5) 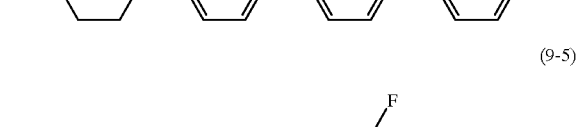
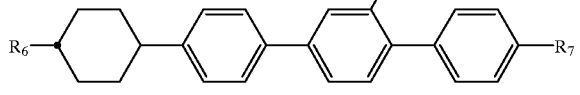

(9-6)

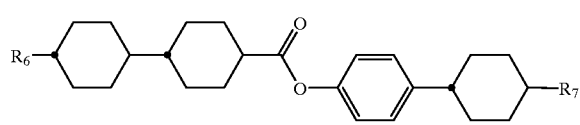

wherein $R_6$ and $R_7$ are as defined above.

The compounds represented by the general formulae (7) to (9) have small absolute values of the dielectric anisotropy, and so they are nearly neutral. The compound of the general formula (7) is mainly used for the purpose of adjusting the viscosity or the optical anisotropy value. Furthermore, the compounds of the general formulae (8) and (9) are used for the purpose of the enlargement of the nematic range such as the rise of the clearing point or the like, or for the purpose of the adjustment of the optical anisotropy value.

When the amount of any compound of the general formulae (7) to (9) is increased, the threshold voltage of the liquid crystal composition increases and the viscosity decreases. Therefore, it is desirable that a largest amount of the compound is used in the range in which the required threshold voltage of the liquid crystal composition is met. In the case that the liquid crystal composition for TFT is prepared, the amount of the compound of the general formulae (7) to (9) to be used is in the range of 40% by weight or less, preferably 35% by weight or less with respect to the total weight of the liquid crystal composition. In the case that the liquid crystal composition for the STN display system or the TN display system is prepared, the amount of the compound to be used is 70% by weight or less, preferably 60% by weight or less.

Furthermore, except an especial case of the liquid crystal composition for an OCB (optically compensated birefringence) mode or the like, an optically active compound may be added to the liquid crystal composition usually for the purposes of forming a helical structure of the liquid crystal composition, adjusting a necessary twist angle, and preventing reverse twist. For such purposes, any of the known optically active compounds may be used, but the following optically active compounds are preferable:

[Symbol: C15]

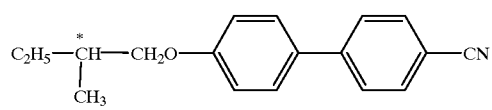

[Symbol: CB15]

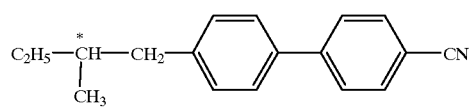

[Symbol: CM21]

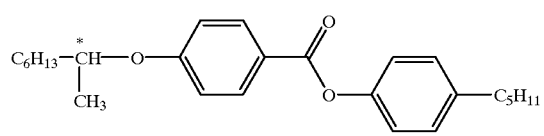

[Symbol: CM33]

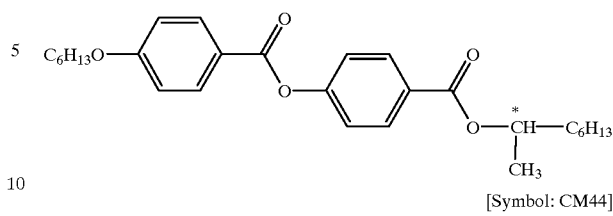

[Symbol: CM44]

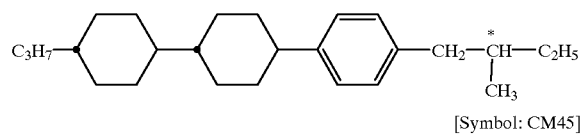

[Symbol: CM45]

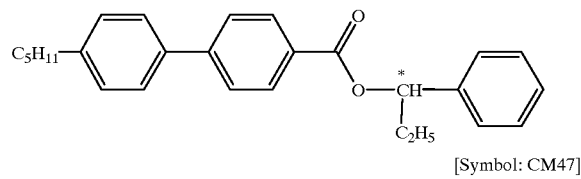

[Symbol: CM47]

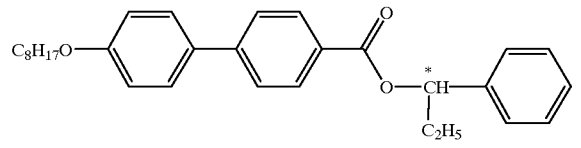

[Symbol: CN]

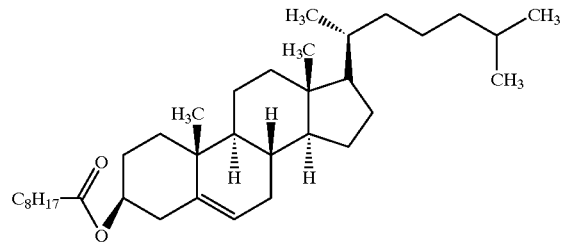

Usually, any of these optically active compounds is added to the liquid crystal composition of the present invention to regulate a pitch length of the twist. In the cases of the liquid crystal compositions for TFT and TN, the pitch length of the twist is preferably regulated so as to be in the range of 40 to 200 μm. In the case of the liquid crystal composition for STN, the pitch length of the twist is preferably regulated so as to be in the range of 6 to 20 μm. Moreover, in the case of a bistable TN mode, the pitch length of the twist is preferably regulated so as to be in the range of 1.5 to 4 μm. In addition, for the purpose of regulating the dependency of the pitch length on a temperature, two or more kinds of optically active compounds may be added.

The liquid crystal composition of the present invention can be prepared in a conventional manner. In general, there can be employed a method which comprises mutually dissolving the above various components at a high temperature.

Furthermore, the liquid crystal composition of the present invention can be used as the liquid crystal composition for a guest-host (GH) mode by adding a dichromatic dye such as a merocyanine dye, a styryl dye, an azo dye, an azomethine dye, an azoxy dye, a quinophthalone dye, an anthraquinone dye or a tetrazine dye to the liquid crystal composition. Moreover, the liquid crystal composition of the present invention can also be used as the liquid crystal composition for NCAP in which microcapsules containing the nematic liquid crystal are used, and as the liquid crystal composition for a polymer dispersion type liquid crystal display device (PDLCD) typified by a polymer network liquid crystal display device (PNLCD) in which a three-dimensional network polymer is formed in the liquid crystal. In addition, the liquid crystal composition of the present invention can also be used as the liquid crystal composition for a double refraction control (ECB) mode and a dynamic scattering mode (DS).

The compound represented by the general formula (1) of the present invention can be manufactured by using a usual chemical technique of an organic synthesis. For example, by suitably combining known reactions described in magazines such as Organic Synthesis, Organic Reactions and Shin Zikken Kagaku Koza, the compound represented by the general formula (1) can be synthesized.

A fluorovinyl site and a difluorovinyl site at a terminal can be build up in accordance with a procedure shown by the following reaction formula. That is to say, a cyclohexanone derivative (T-1) prepared by a method described in literature is subjected to a Wittig reaction by the use of a phosphonium salt of chloromethyl methyl ether, and the resulting enol ether is then converted under acidic conditions into an aldehyde substance (T-2). This aldehyde substance is reacted with sodium chlorodifluoroacetate in the presence of triphenylphosphine to obtain a difluorocompound of the compounds (1). Furthermore, this difluorocompound is subjected to a reduction reaction to prepare a monofluorocompound of the compounds (1).

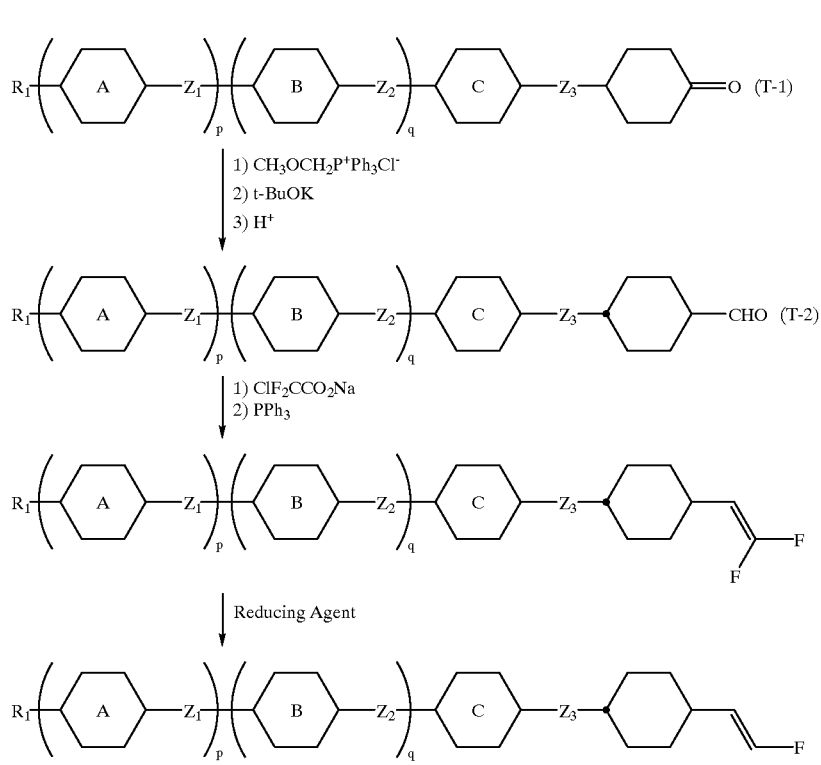

(a)

The compound of the chemical formula (1) in which m is 1 can be prepared by subjecting the above aldehyde substance (T-2) to the reactions of the following reaction formula (b) in turn.

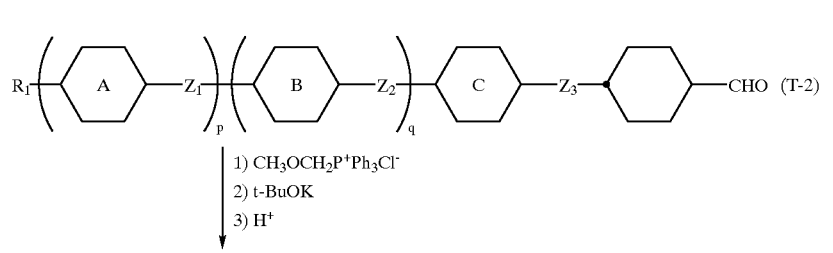

(b)

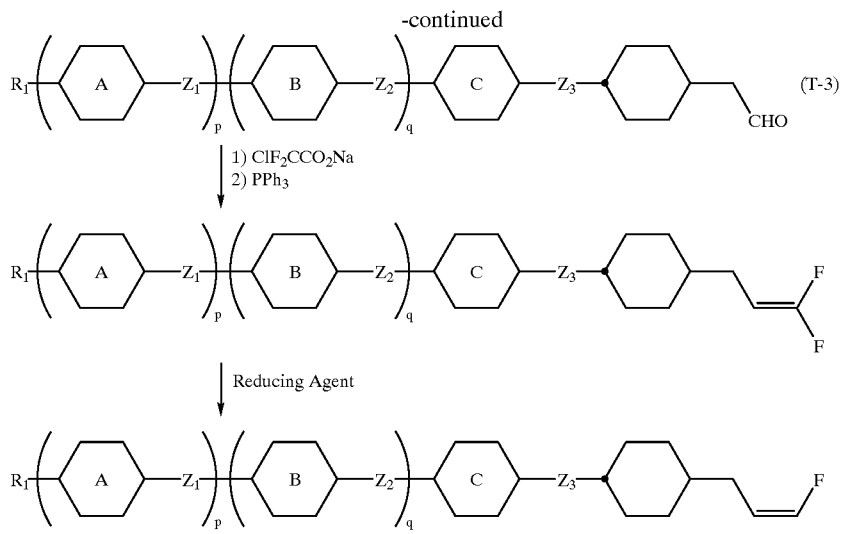

As shown in the following reaction formula (c), the compound of the chemical formula (1) in which m is 2 can be prepared by reacting the above derivative (T-1) with 3-(1,3-dioxane-2-yl)ethyltriphenylphosphonium bromide, reducing the resulting Wittig adduct (T-4), carrying out a protective group removal reaction to obtain an aldehyde substance (T-5), and then subjecting this aldehyde substance (T-5) to the above reaction.

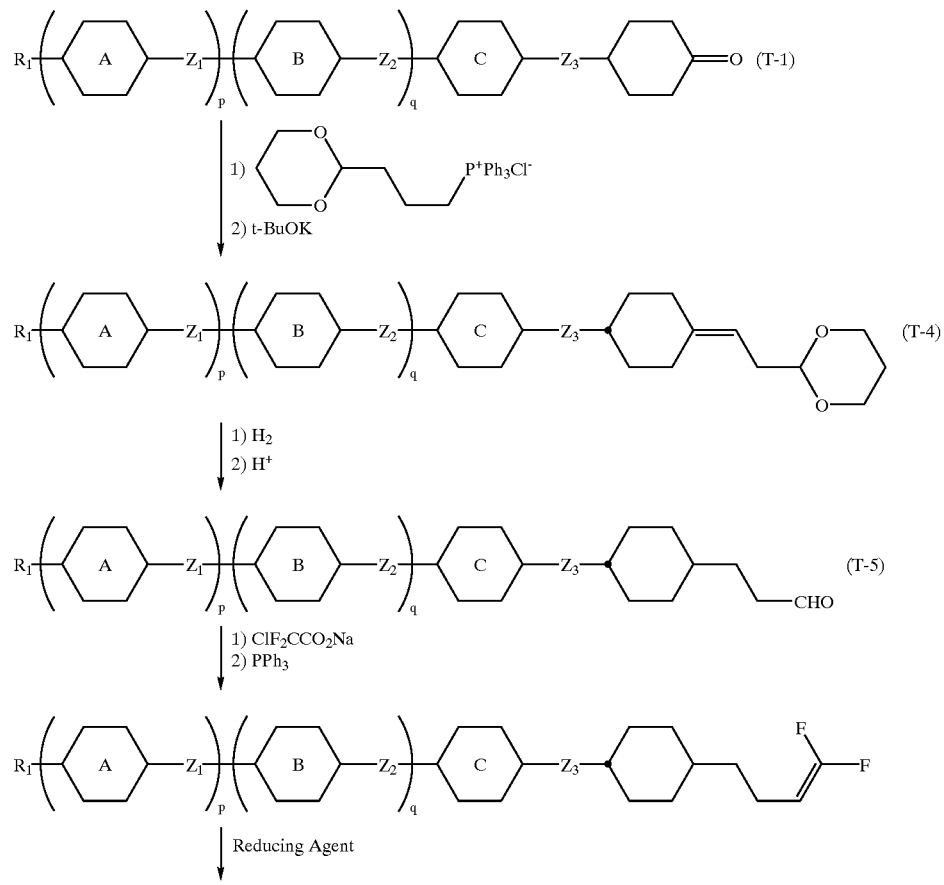

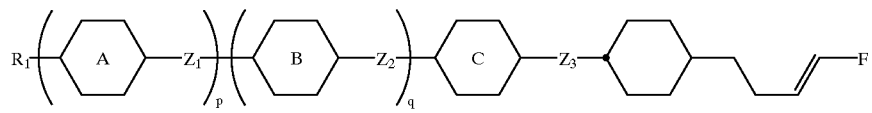

The compound of the chemical formula (1) in which m is 3 or more can be prepared by suitably combining some reactions of the above reaction formulae (a) and (b).

Description will be made in more detail by the use of the following reaction formula (d). A cyclohexanone derivative (T-6) or an aldehyde substance (T-7) is reacted with a phenyllithium derivative prepared from a phenyl bromide (T-8) and a lithium reagent, and then carrying out dehydration and a hydrogenation reaction to obtain a compound (T-9). Next, this compound (T-9) is reacted with the lithium reagent again and then a compound (T-10) or (T-11), followed by dehydration and hydrogenation to obtain a cyclohexanone derivative (T-12). This derivative (T-12) can be converted into a compound (1-2) by the process of the reaction formulae (a) to (c).

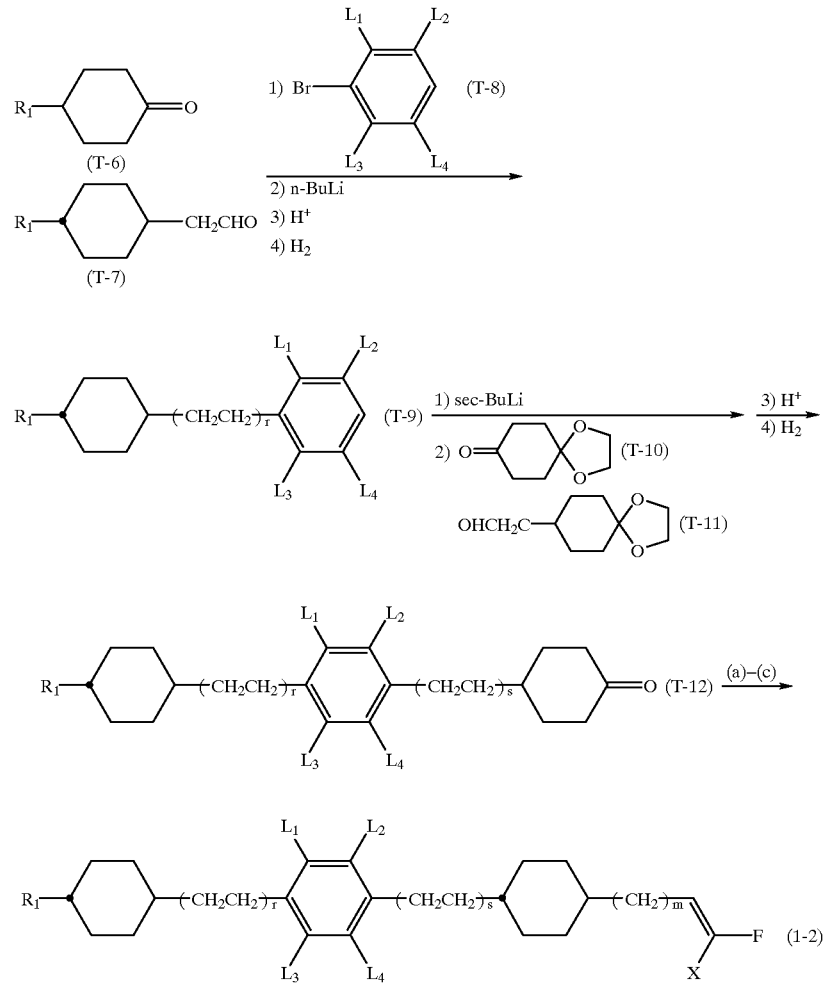

Furthermore, as shown by the following reaction formula (e), phenol or an alcohol derivative (T-13) is reacted with a bromide (T-14) in the presence of basic conditions to obtain an ether (T-15). Next, this ether is subjected to a protective group removal reaction under acidic conditions to obtain a cyclohexanone derivative (T-16), and for this derivative (T-16), the above reaction formulae (a) to (c) are conducted to obtain a compound (1-3).

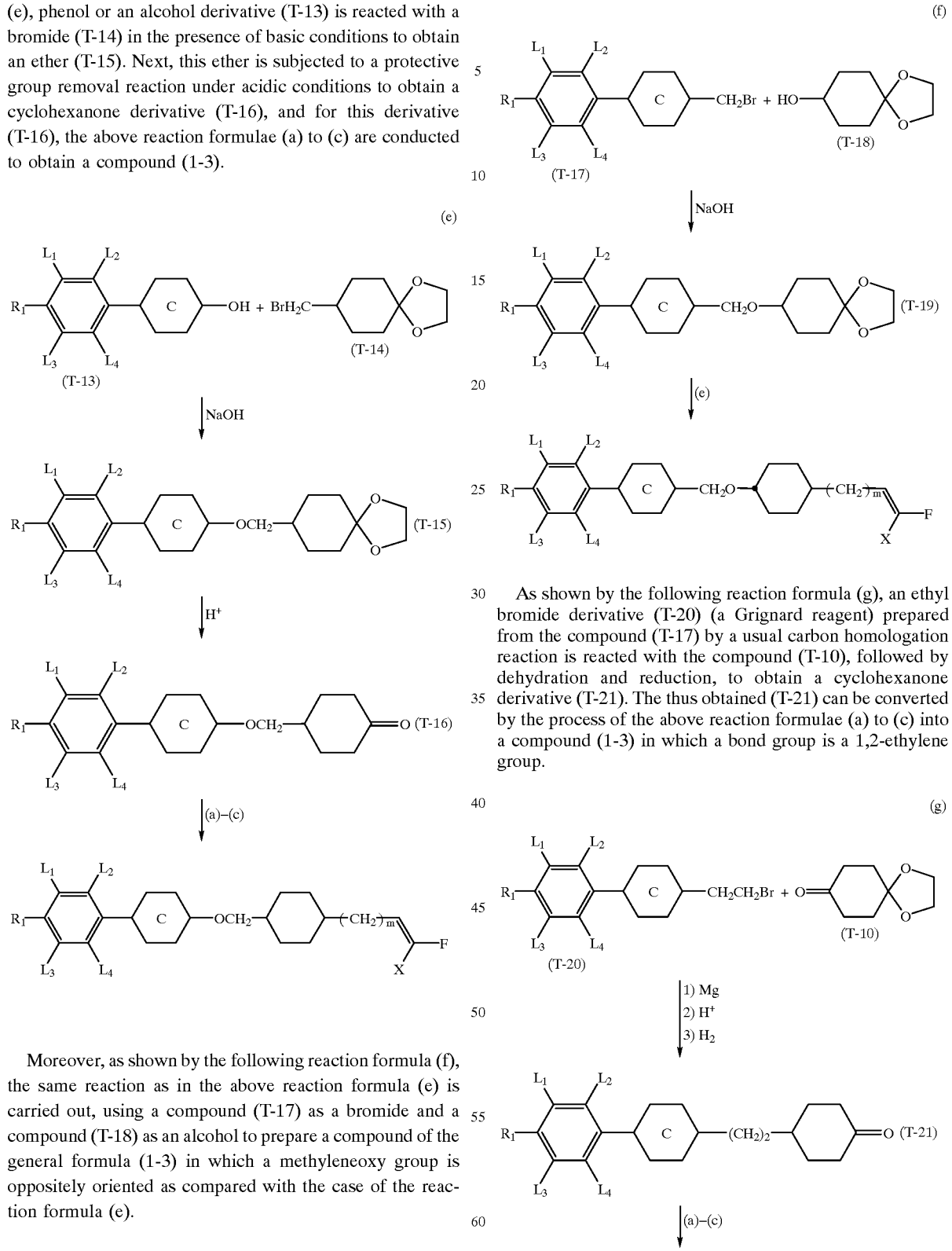

Moreover, as shown by the following reaction formula (f), the same reaction as in the above reaction formula (e) is carried out, using a compound (T-17) as a bromide and a compound (T-18) as an alcohol to prepare a compound of the general formula (1-3) in which a methyleneoxy group is oppositely oriented as compared with the case of the reaction formula (e).

As shown by the following reaction formula (g), an ethyl bromide derivative (T-20) (a Grignard reagent) prepared from the compound (T-17) by a usual carbon homologation reaction is reacted with the compound (T-10), followed by dehydration and reduction, to obtain a cyclohexanone derivative (T-21). The thus obtained (T-21) can be converted by the process of the above reaction formulae (a) to (c) into a compound (1-3) in which a bond group is a 1,2-ethylene group.

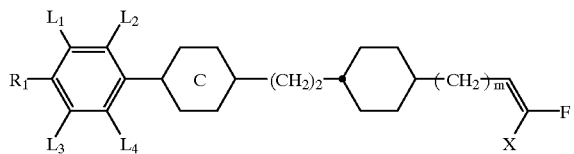
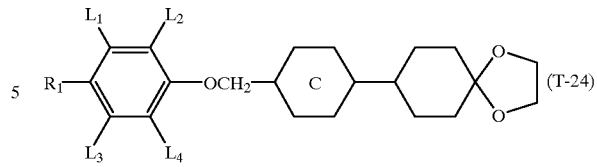

As shown by the following reaction formula (h), the compound (T-20) is further subjected to the carbon homologation reaction to obtain a butyl bromide derivative (T-21), and the same reaction as in the above reaction formula (g) is then conducted to prepare a composition (1-3) in which a bond group is a 1,4-butylene group.

(h)

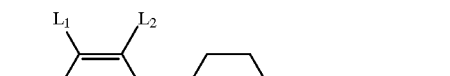

Carbon Homologation Reaction

(g)

As shown by the following reaction formula (i), a phenol derivative (T-22) is reacted with a bromide (T-23) to obtain an ether (T-24). Next, this ether (T-24) is subjected to the process of the above chemical formula (e) to prepare a compound (1-3) in which $Z_2$ is $OCH_2$.

(i)

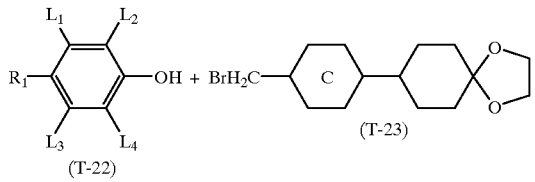

NaOH

Furthermore, as shown in the following reaction formula (j), a bromide (T-25) is reacted with phenol or an alcohol (T-26) in accordance with the process of the above (e) to prepare a compound (1-3) in which $Z_2$ is $CH_2O$.

(j)

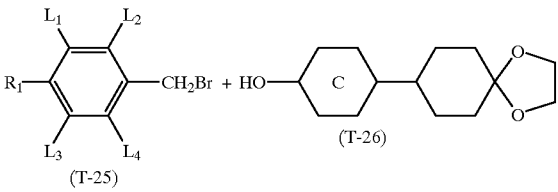

NaOH

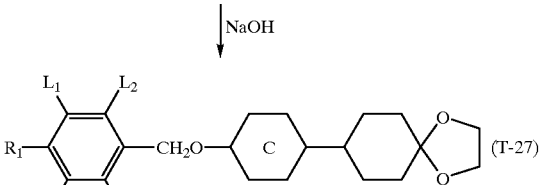

(e)

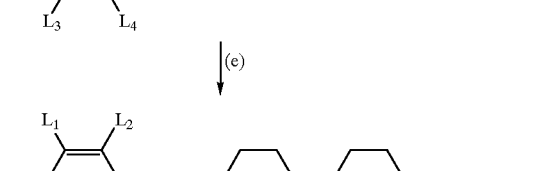

As shown in the following reaction formula (k), a phenethyl bromide derivative (T-28) (a Grignard reagent) is reacted with a monoketal (T-29), followed by dehydration, to obtain a cyclohexene derivative (T-30). Next, a cyclohexene ring portion of this derivative (T-30) is hydrogenated, and the resulting cyclohexanone (T-31) is then subjected to the reactions of the above reaction formulae (a) to (c), thereby obtaining a compound (1-3) in which a ring C is 1,4-cyclohexylene. Moreover, the derivative (T-30) is dehydrogenated with chloranil or the like to obtain a compound (T-32), and the reactions of the above reaction formulae (a) to (c) are then conducted to obtain a compound (1-3) in which the ring C is 1,4-phenylene.

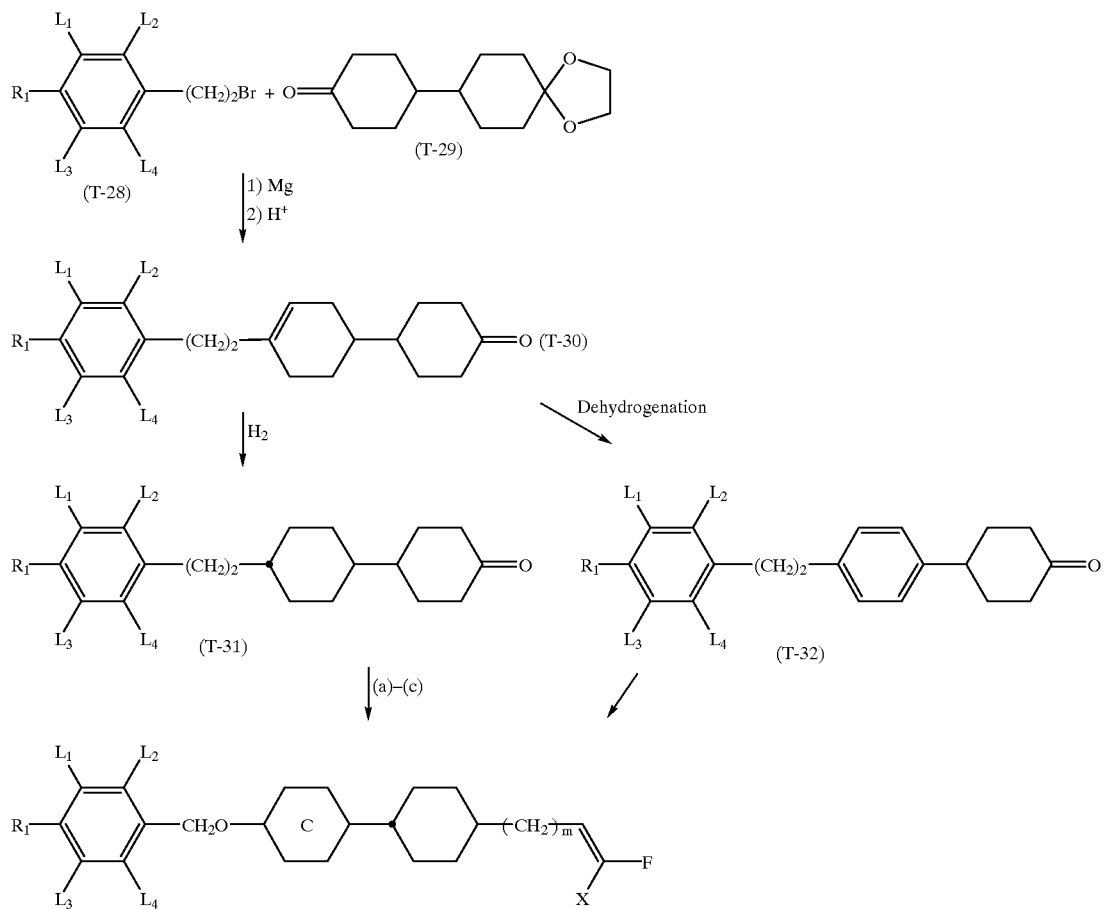

As shown in the following reaction formula (l), phenethyl bromide (T-28) is subjected to the carbon homologation reaction to obtain butyl bromide (T-33). Next, butyl bromide (T-33) is subjected to the above reaction (g) to prepare a compound (1-3) in which $Z_2$ is 1,4-butylene.

(l)

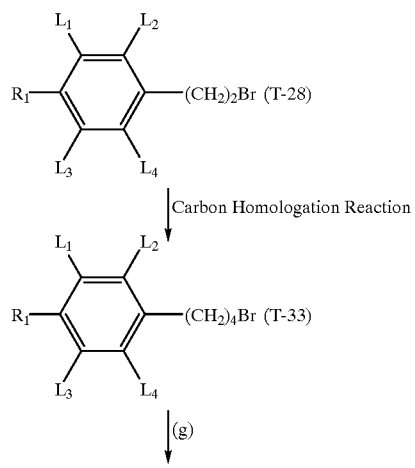

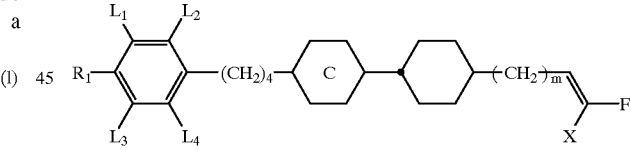

As shown in the following reaction formula (m), an aldehyde (T-35) obtained by demethylation and then oxidation of a compound (T-34) described in Japanese Patent Publication No. 16331/1991 is subjected to the above reactions (a) to (b), thereby obtaining a compound (1-1-1) in which m is 0. Alternatively, when the above reactions (a) to (c) are applied to an aldehyde (T-36) obtained by subjecting the aldehyde (T-35) to the carbon homologation reaction, a compound (1-1-1) in which m is 1 or more is obtained.

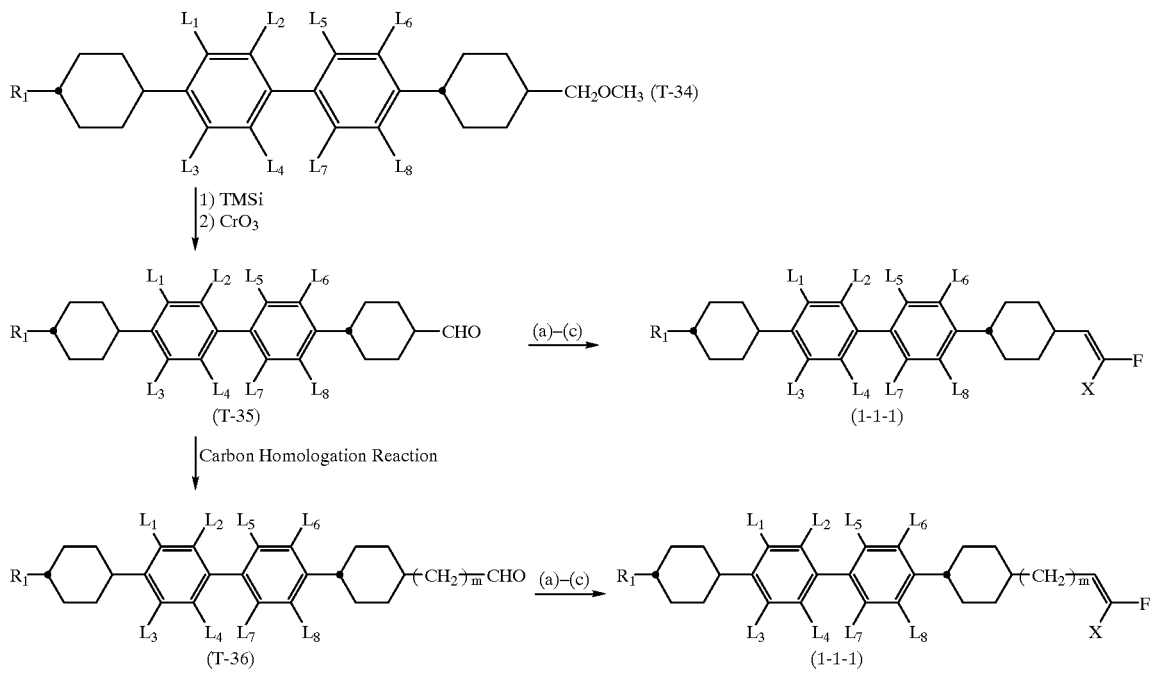
(m)
As shown in the following reaction formula (n), a bromide (T-37) is reacted with the compound (T-10), followed by dehydration and then hydrogenation, to obtain a cyclohexane derivative (T-38). This derivative (T-38) can be converted into a compound (T-39) by the carbon homologation reaction. The compounds (T-38) and (T-39) can each be converted into a compound (1-1-2) by the above reactions (a) to (c).
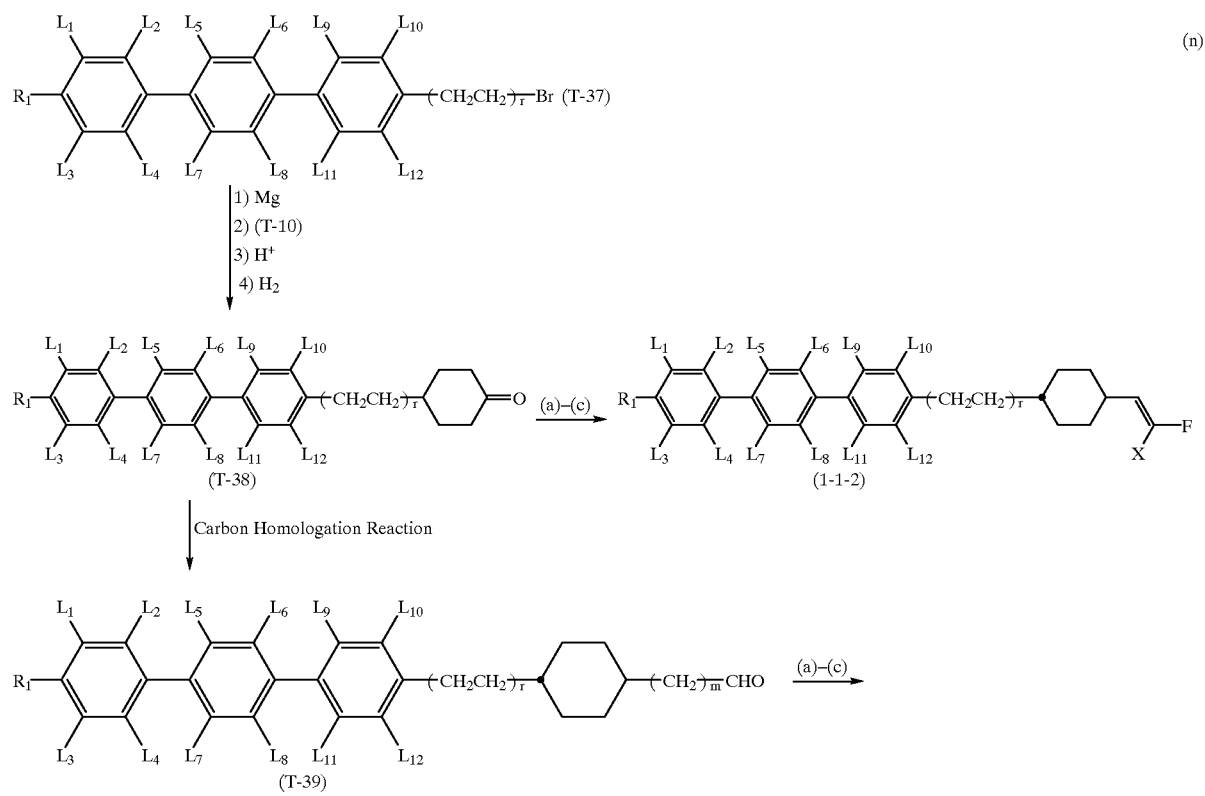
(n)

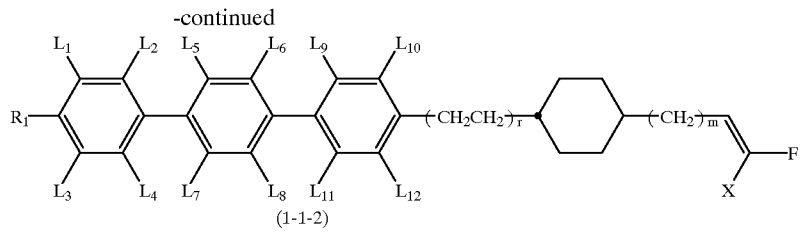
(1-1-2)
As shown in the following reaction formula (o), a bromide (T-40) is reacted with the compound (T-29), followed by dehydration and then hydrogenation, to obtain a cyclohexanone derivative (T-41). This derivative (T-41) can be converted into a compound (T-42) by the carbon homologation reaction. The compounds (T-41) and (T-42) can each be converted into a compound (1-1-3) by the above reactions (a) to (c).
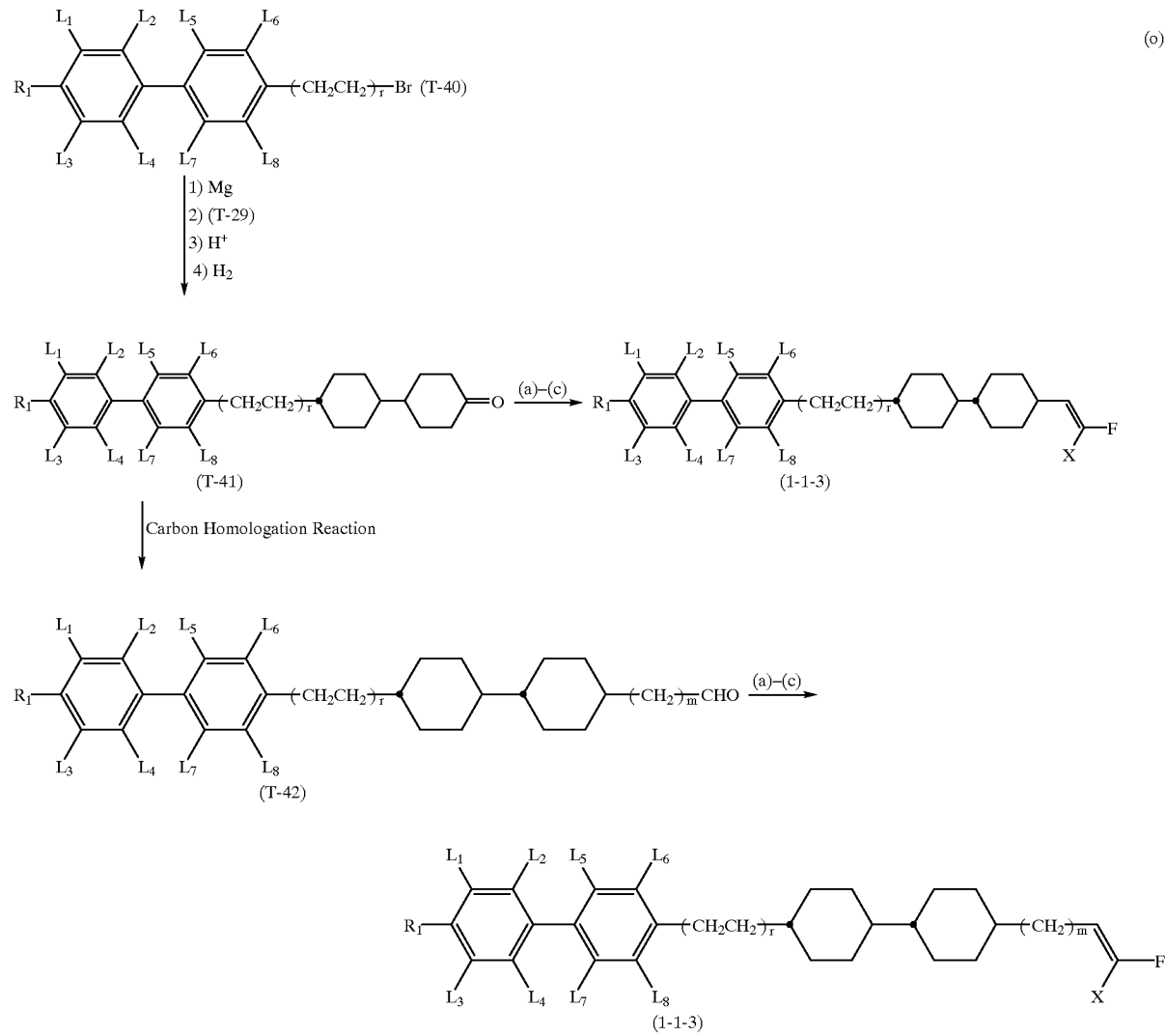
(o)

As shown in the following reaction formula (p), a cis-olefin (T-45) obtained from a phosphonium salt (T-43) and an aldehyde (T-44) is subjected to inversion of a conformation to obtain a compound (T-46). The inversion reaction can be suitably carried out in a manner described in Japanese Patent Publication Nos. 2653/1995 and 2654/1995. This compound (T-46) is reduced with DIBAL (diisobutylaluminum hydride) to obtain an aldehyde (T-47). This aldehyde (T-47) can be converted into a compound (T-48) by the usual carbon homologation reaction. The compounds (T-47) and (T-48) can each be converted into a compound (1-4-1) by the above reactions (a) to (c).

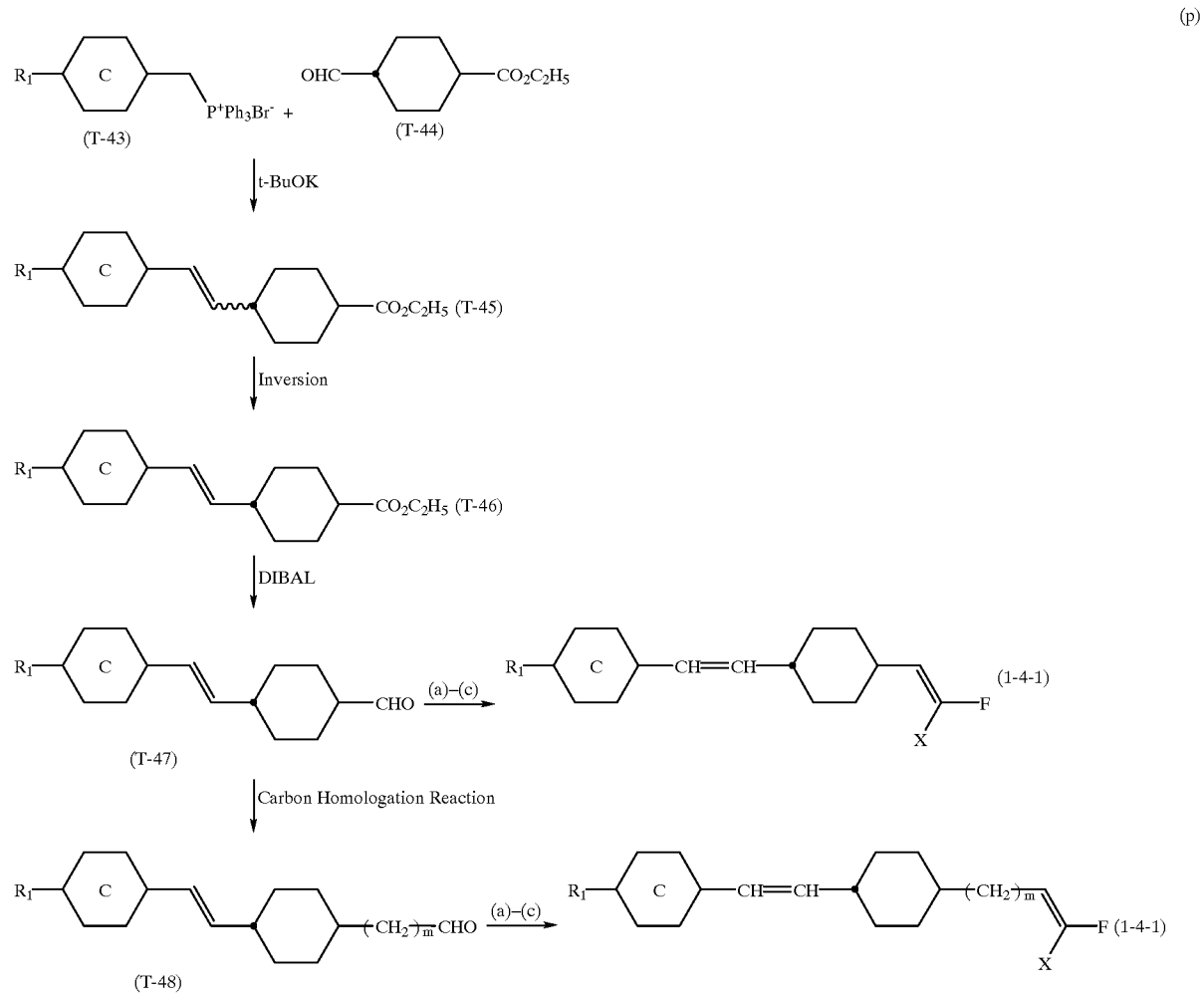

(p)

As shown in the following reaction formula (q), compounds (1-4-2) and (1-4-3) can be prepared from compounds (T-49) and (T-50), respectively, in accordance with the procedure (p).

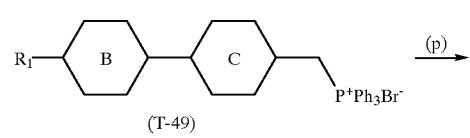

(q)

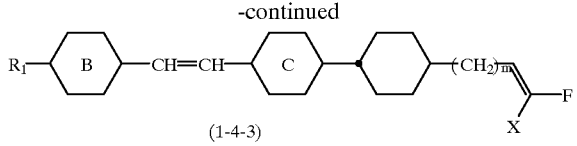

As shown in the following reaction formula (r), an iodide (T-51) is reacted with butyl lithium and tetrafluoroethylene in turn to obtain a compound (T-52). A compound (T-53) similarly treated with the base is then reacted with the above compound (T-52) to obtain a compound (T-54). Afterward, this compound (T-54) is substituted jected to the reactions (a) to (c), thereby preparing a compound (1-4-4).

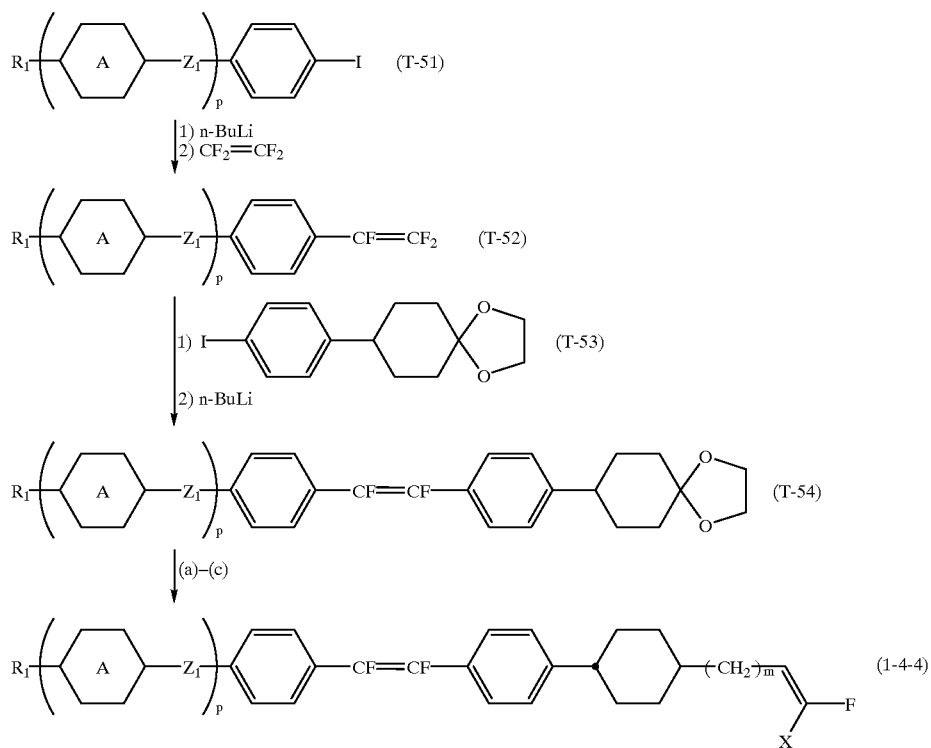

(r)

As shown in the following reaction formula (s), a dithiocarboxylic acid (T-55) prepared from a Grignard reagent of a phenyl halide and carbon disulfide is converted into an acid chloride. Next, this compound is reacted with a phenol (T-56) to obtain a thioester, and this thioester is then fluorinated with DAST (diethylaminosulfur trifluoride) to obtain a compound (T-57). Afterward, this compound (T-57) is subjected to the reactions (a) to (c), thereby preparing a compound (1-4-5).

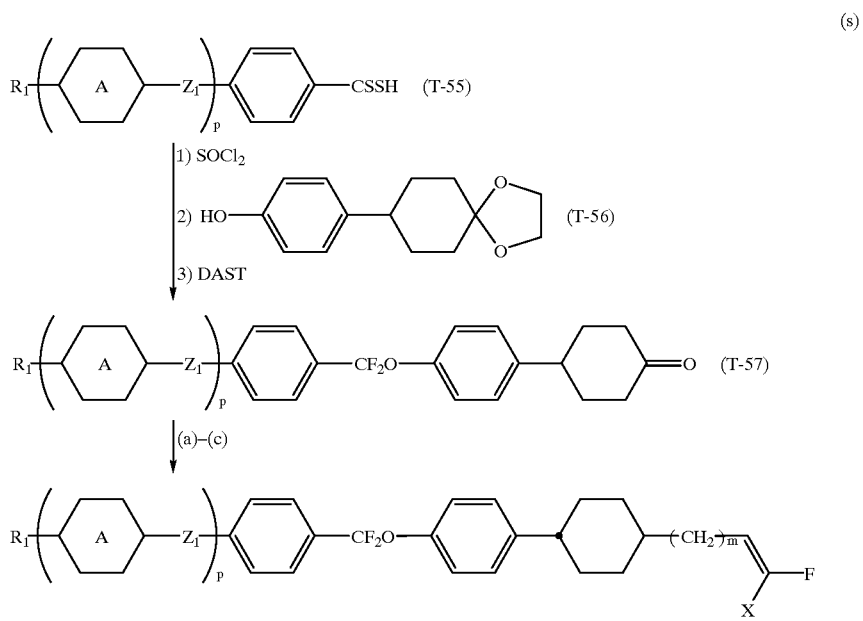

(s)

As shown in the following reaction formula (t), a compound (1-4-5) can be prepared in accordance with the above process (s) by the use of a phenol (T-58) and a dithiocarboxylic acid (T-59).

As shown in the following reaction formula (v), a compound (1-4-7) can be prepared by subjecting a cyclohexanone (T-65) obtained from a ketone (T-63) and a bromide (Y-64) to the above reactions (a) to (c).

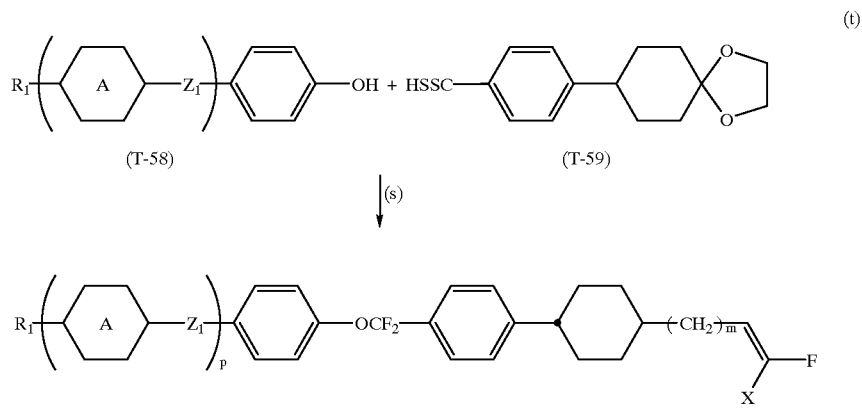

As shown in the following reaction formula (u), a compound (1-4-6) can be prepared by subjecting a cyclohexanone (T-62) obtained from a ketone (T-60) and a bromide (T-61) to the above reactions (a) to (c).

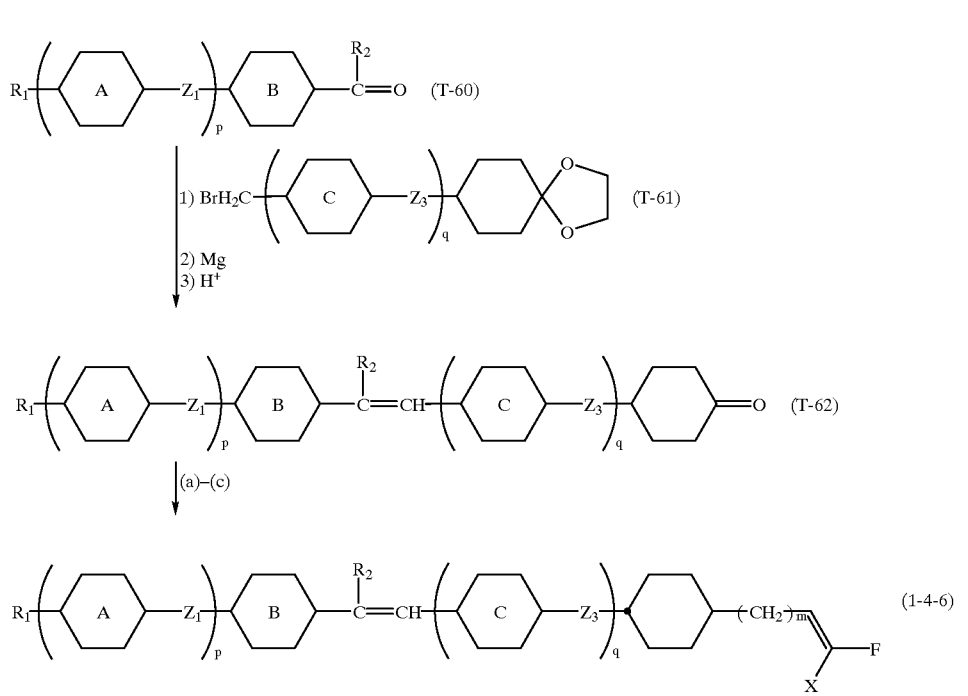

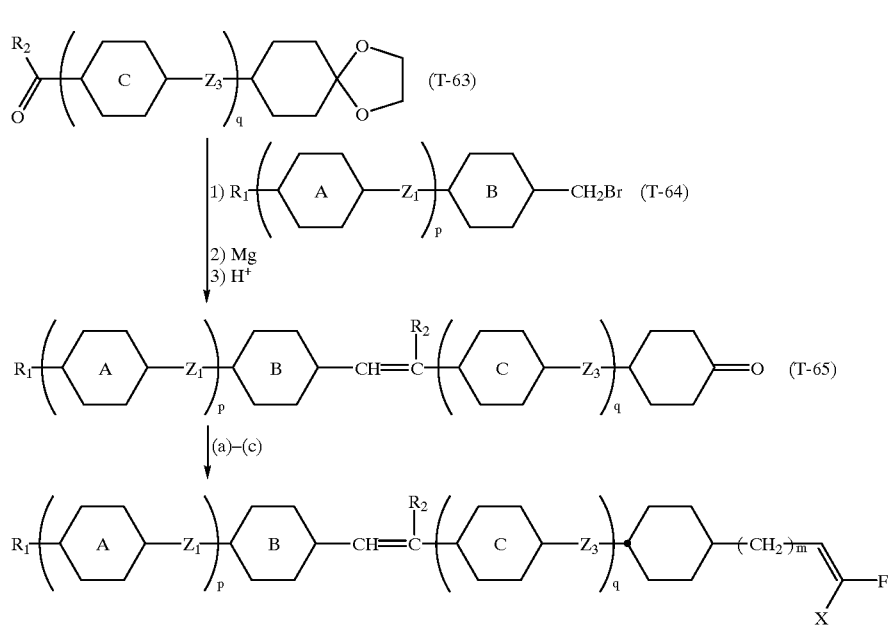

(v)

EXAMPLES

Next, the present invention will be described in more detail with reference to examples. The scope of the present invention should not be limited to these examples at all.

Example 1

Preparation of 4'-propyl-4-(4-(4-(4-fluoro-3-butenyl)cyclohexyl)cyclohexyl)biphenyl [a compound of the general formula (1) in which $R_1$=a propyl group, a ring A=a ring B=1,4-phenylene, a ring C=1,4-cyclohexylene, $Z_1=Z_2=Z_3$=a single bond, p=q=1, m=2, and X=a hydrogen atom]

To a mixture of 2-(1,3-dioxane-2-yl)ethyltriphenylphosphonium bromide (110 mmol) and 50 ml of THF, t-BuOK (110 mmol) was added, followed by stirring at room temperature for 30 minutes. Next, 50 ml of a THF solution containing 4-(4-(4'-propylbiphenyl-4-yl)cyclohexyl)cyclohexanone (100 mmol) prepared from 4'-propyl-4-bromobiphenyl and bicyclohexandione=monoethylene ketal in accordance with a process of Japanese Patent Application Laid-open No. 211711/1994 was added thereto at 0° C. or less, followed by stirring at the same temperature for 2 hours.

THF was removed under reduced pressure, and 500 ml of heptane was then added thereto. Next, the precipitated crystals were removed by filtration, and the resulting filtrate was then concentrated. To the residue, there were added 30 ml of toluene, 100 ml of ethanol and 10 g of 5% palladium carbon, and the mixture was then stirred under a hydrogen atmosphere for 14 hours. After it was confirmed that the absorption of the hydrogen gas stopped, the catalyst was removed by filtration. The filtrate was concentrated, and the residue was recrystallized from ethanol 3 times, thereby obtaining 4'-propyl-4-(4-(4-(2-(1,3-dioxane-2-yl)ethyl)cyclohexyl)cyclohexyl)biphenyl (33 mmol).

A mixture of 4'-propyl-4-(4-(4-(2-(1,3-dioxane-2-yl)ethyl)cyclohexyl)cyclohexyl)biphenyl (30 mmol), 100 ml of toluene and 30 ml of formic acid was refluxed for 2 hours, and the reaction product was then cooled to room temperature. Afterward, the reaction product was sufficiently washed with water, saturated sodium hydrogencarbonate and water in this order, and then dried over anhydrous magnesium sulfate. The solvent was removed under reduced pressure, and the resulting residue was then recrystallized from heptane, thereby obtaining 3-(4-(4-(4'-propylbiphenyl-4-yl)cyclohexyl)cyclohexyl)propanal (25 mmol).

To a mixture of 3-(4-(4-(4'-propylbiphenyl-4-yl)cyclohexyl)cyclohexyl)propanal (25 mmol), triphenylphosphine (26 mmol) and 70 ml of dry DMF, 60 ml of a DMF solution containing sodium chlorodifluoroacetate (26 mmol) was added dropwise at about 100° C. After the completion of the dropping, the solution was stirred for 30 minutes, while the same temperature was maintained. After the solution was cooled to room temperature, 100 ml of toluene was added, followed by extraction.

The solvent was removed, and the resulting residue was purified by column chromatography (a toluene-heptane mixing solvent) and then recrystallization (heptane) to obtain 4'-propyl-4-(4-(4-(4,4-difluoro-3-butenyl)cyclohexyl)cyclohexyl)biphenyl (19 mmol) [a compound of the general formula (1) in which $R_1$=a propyl group, a ring A=a ring B=1,4-phenylene, a ring C=1,4-cyclohexylene, $Z_1=Z_2=Z_3$=a single bond, p=q=0, m=2, and X=a fluorine atom].

Solution of sodium bis(2-methoxyethoxy)aluminum hydride in toluene (Red-Al 17 mmol) was added to a mixture of 4'-propyl-4-(4-(4-(4,4-difluoro-3-butenyl)cyclohexyl)cyclohexyl)biphenyl (15 mmol) and 50 ml of THF, followed by reflux for 10 hours. Next, the reaction product was poured into 200 ml of 2M hydrochloric acid, and extraction was then carried out with 100 ml of toluene. After the resulting organic layer was separated and then dried, the solvent was removed, and the residue was purified by column chromatography (a toluene-heptane mixing solvent) and next recrystallization (heptane) to obtain the desired compound (4 mmol). Its structure was properly supported by spectrum data.

In accordance with the procedure of Example 1, the compounds represented by the following formula (1-1-3) were prepared.

(1-1-3)

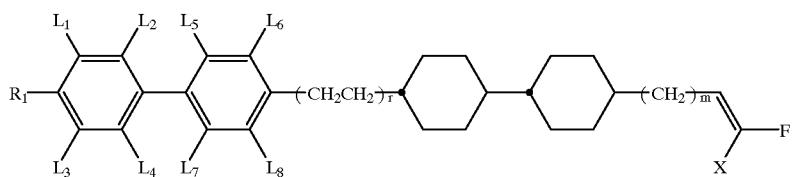

Typically, the compounds shown in Tables 1 and 2 were prepared.

TABLE 1

| r | R$_1$ | L1 | L2 | L3 | L4 | L5 | L6 | L7 | L8 | m | X |
|---|---|---|---|---|---|---|---|---|---|---|---|
| 0 | C$_3$H$_7$ | H | H | H | H | H | H | H | H | 0 | H |
| 0 | C$_3$H$_7$ | H | H | H | H | H | H | H | H | 0 | F |
| 0 | CH$_2$=CH | H | H | H | H | H | H | H | H | 0 | F |
| 0 | C$_5$H$_{11}$ | H | H | H | H | H | H | H | H | 0 | F |
| 0 | C$_3$H$_7$ | H | F | H | H | H | H | H | H | 0 | F |
| 0 | C$_3$H$_7$ | H | H | H | H | H | F | H | H | 0 | F |
| 0 | C$_3$H$_7$ | H | F | H | H | H | F | H | H | 0 | F |
| 0 | CH$_3$O | F | H | H | H | H | H | H | H | 0 | F |
| 0 | C$_3$H$_7$ | H | H | H | H | H | H | H | H | 1 | H |
| 0 | C$_3$H$_7$ | H | H | H | H | H | H | H | H | 1 | F |
| 0 | C$_3$H$_7$ | H | H | H | H | H | H | H | H | 2 | F |
| 0 | C$_3$H$_7$ | H | F | H | H | H | H | H | H | 2 | F |
| 0 | C$_5$H$_{11}$ | F | F | H | H | H | H | H | H | 2 | F |
| 0 | C$_3$H$_7$ | H | H | H | H | H | H | H | H | 3 | F |
| 0 | C$_5$H$_{11}$ | H | H | H | H | H | H | H | H | 4 | F |
| 0 | C$_3$H$_7$ | H | H | H | H | H | H | H | H | 5 | H |

TABLE 2

| r | R$_1$ | L1 | L2 | L3 | L4 | L5 | L6 | L7 | L8 | m | X |
|---|---|---|---|---|---|---|---|---|---|---|---|
| 1 | C$_3$H$_7$ | H | H | H | H | H | H | H | H | 0 | H |
| 1 | C$_3$H$_7$ | H | H | H | H | H | H | H | H | 0 | F |
| 1 | CH$_2$=CH | H | H | H | H | H | H | H | H | 0 | F |
| 1 | C$_5$H$_{11}$ | H | H | H | H | H | H | H | H | 0 | F |
| 1 | C$_3$H$_7$ | H | F | H | H | H | H | H | H | 0 | F |
| 1 | C$_3$H$_7$ | H | H | H | H | H | F | H | H | 0 | F |
| 1 | C$_3$H$_7$ | H | F | H | H | H | F | H | H | 0 | F |
| 1 | CH$_3$O | F | H | H | H | H | H | H | H | 0 | F |
| 1 | C$_3$H$_7$ | H | H | H | H | H | H | H | H | 1 | H |
| 1 | C$_3$H$_7$ | H | H | H | H | H | H | H | H | 1 | F |
| 1 | C$_3$H$_7$ | H | H | H | H | H | H | H | H | 2 | F |
| 1 | C$_3$H$_7$ | H | F | H | H | H | H | H | H | 2 | F |
| 1 | C$_5$H$_{11}$ | F | F | H | H | H | H | H | H | 2 | F |
| 1 | C$_3$H$_7$ | H | H | H | H | H | H | H | H | 3 | F |
| 1 | C$_5$H$_{11}$ | H | H | H | H | H | H | H | H | 4 | F |
| 1 | C$_3$H$_7$ | H | H | H | H | H | H | H | H | 5 | H |

In accordance with the procedure of Example 1, the compounds represented by the following formula (1-1-1) were prepared.

(1-1-1)

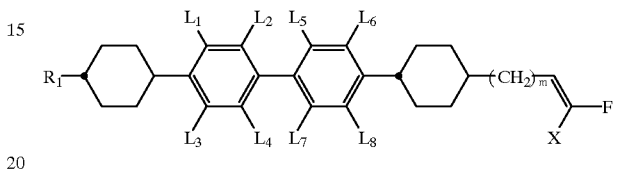

Typically, the compounds shown in Table 3 were prepared. In the following tables, transition temperatures (° C.) of compounds are added, and C, S, N and I mean a crystalline phase, a smectic phase, a nematic phase and an isotropic phase, respectively.

TABLE 3

| R$_1$ | L1 | L2 | L3 | L4 | L5 | L6 | L7 | L8 | m | X |
|---|---|---|---|---|---|---|---|---|---|---|---|
| C$_3$H$_7$ | H | H | H | H | H | H | H | H | 0 | H |
| C$_3$H$_7$ | H | H | H | H | H | H | H | H | 0 | F |
| C$_4$H$_9$ | H | H | H | H | H | H | H | H | 0 | H |
| C$_5$H$_{11}$ | H | H | H | H | H | H | H | H | 0 | F*1) |
| CH$_2$=CH | H | H | H | H | H | H | H | H | 0 | F |
| ╲╱╱ | H | H | H | H | H | H | H | H | 0 | F |
| ╲═╱╲╱ | H | H | H | H | H | H | H | H | 0 | F |
| F╲╱═╲╱ | H | H | H | H | H | H | H | H | 0 | F |
| C$_3$H$_7$ | H | F | H | H | H | H | H | H | 0 | F |
| C$_3$H$_7$ | H | H | H | H | F | H | H | H | 0 | F |
| C$_3$H$_7$ | F | F | H | H | H | H | H | H | 0 | F |
| C$_3$H$_7$ | H | H | H | H | H | H | H | H | 2 | H |
| C$_3$H$_7$ | H | H | H | H | H | H | H | H | 2 | F |
| C$_3$H$_7$ | H | F | H | H | H | H | H | H | 2 | F |
| C$_5$H$_{11}$ | H | H | H | H | F | H | H | H | 2 | F |

*1) C 56.8 S 214.3 N 268.3 I

In accordance with the procedure of Example 1, the compounds represented by the following formula (1-1-2) were prepared.

(1-1-2)

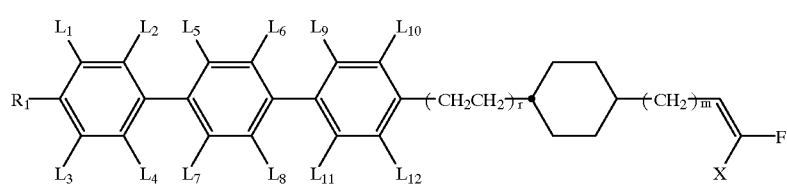

Typically, the compounds shown in Tables 4 and 5 were prepared.

TABLE 4

| r | $R_1$ | L1 | L2 | L3 | L4 | L5 | L6 | L7 | L8 | L9 | L10 | L11 | L12 | m | X |
|---|---|---|---|---|---|---|---|---|---|---|---|---|---|---|---|
| 0 | $C_3H_7$ | H | H | H | H | H | H | H | H | H | H | H | H | 0 | H |
| 0 | $C_3H_7$ | H | H | H | H | H | H | H | H | H | H | H | H | 0 | F |
| 0 | $C_3H_7$ | H | H | H | H | H | F | H | H | H | H | H | H | 0 | F |
| 0 | $C_5H_{11}$ | H | H | H | H | H | F | H | H | H | H | H | H | 0 | F |
| 0 | $CH_3OCH_2$ | H | H | H | H | H | F | F | H | H | H | H | H | 0 | F |
| 0 | $C_3H_7$ | H | H | H | H | F | H | H | F | H | H | H | H | 0 | F |
| 0 | $C_3H_7$ | H | H | H | H | H | H | H | H | H | H | H | H | 2 | F |
| 0 | $C_5H_{11}$ | H | H | H | H | H | H | H | H | H | H | H | H | 2 | F |
| 0 | $C_3H_7$ | H | H | H | H | H | H | H | H | H | H | H | H | 4 | F |

TABLE 5

| r | $R_1$ | L1 | L2 | L3 | L4 | L5 | L6 | L7 | L8 | L9 | L10 | L11 | L12 | m | X |
|---|---|---|---|---|---|---|---|---|---|---|---|---|---|---|---|
| 1 | $C_3H_7$ | H | H | H | H | H | H | H | H | H | H | H | H | 0 | H |
| 1 | $C_3H_7$ | H | H | H | H | H | H | H | H | H | H | H | H | 0 | F |
| 1 | $C_3H_7$ | H | H | H | H | H | F | H | H | H | H | H | H | 0 | F |
| 1 | $C_5H_{11}$ | H | H | H | H | H | F | H | H | H | H | H | H | 0 | F |
| 1 | $CH_3OCH_2$ | H | H | H | H | H | F | F | H | H | H | H | H | 0 | F |
| 1 | $C_3H_7$ | H | H | H | H | F | H | H | F | H | H | H | H | 0 | F |
| 1 | $C_3H_7$ | H | H | H | H | H | H | H | H | H | H | H | H | 2 | F |
| 1 | $C_5H_{11}$ | H | H | H | H | H | H | H | H | H | H | H | H | 2 | F |
| 1 | $C_3H_7$ | H | H | H | H | H | H | H | H | H | H | H | H | 4 | F |

In accordance with the procedure of Example 1, the compounds represented by the following formula (1-1) were prepared.

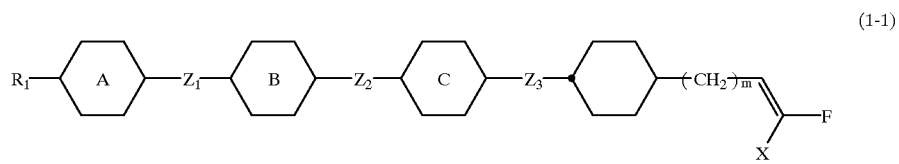

(1-1)

Typically, the compounds shown in Table 6 were prepared.

TABLE 6

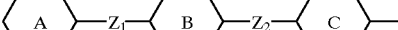

| $R_1$ | structure | m | X |
|---|---|---|---|
| $C_3H_7$ |  | 0 | H |
| $C_3H_7$ |  | 0 | F |
| $C_3H_7$ | 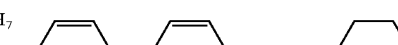 | 0 | F |

TABLE 6-continued

| $R_1$ | structure | m | X |
|---|---|---|---|
| $C_3H_7$ |  | 2 | F |
| $C_3H_7$ | 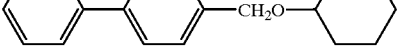 | 0 | F |
| $C_3H_7$ | 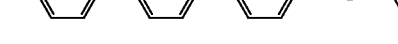 | 2 | F |

TABLE 6-continued

| $R_1$ | A-$Z_1$-B-$Z_2$-C-$Z_3$ | m | X |
|---|---|---|---|
| $C_3H_7$ | phenyl-(2-fluoro-phenyl)-phenyl-CH$_2$O-cyclohexyl | 0 | F |
| $C_3H_7$ | phenyl-phenyl-cyclohexyl-(CH$_2$)$_4$ | 0 | H |
| $C_3H_7$ | phenyl-phenyl-cyclohexyl-(CH$_2$)$_4$ | 0 | F |
| $C_3H_7$ | phenyl-phenyl-cyclohexyl-(CH$_2$)$_4$ | 2 | F |
| $C_3H_7$ | phenyl-phenyl-cyclohexyl-(CH$_2$)$_4$ | 4 | F |
| $C_3H_7$ | phenyl-phenyl-(1,3-dioxane)-(CH$_2$)$_2$ | 0 | F |

Example 2

Preparation of 2,3-difluoro-4-(4-propylcyclohexyl)-1-(4-(2,2-difluoroethenyl)cyclohexyl)benzene [a compound of the general formula (1) in which $R_1$=a propyl group, a ring C=2,3-difluoro-1,4-phenylene, a ring B=1,4-cyclohexylene, $Z_2$=$Z_3$=a single bond, p=0, q=1, m=0, and X=a fluorine atom]

A hexane solution (corresponding to 49 mmol) sec-butyl lithium was added dropwise at −78° C. to 90 ml of a THF solution containing 2,3-difluoro-1-(4-propylcyclohexyl) benzene (45 mmol) prepared from 2,3-difluorobromobenzene and 4-propylcyclohexanone in accordance with a process of Japanese Patent Application Laid-open No. 176240/1984, followed by stirring for 30 minutes.

Next, 50 ml of a THF solution containing cyclohexane-1,4-dione=monoketal (49 mmol) was added to the solution at the same temperature, and the temperature of the mixture was gradually raised to room temperature. Afterward, 90 ml of water was added, and the solution was then sufficiently extracted with ethyl acetate. The resulting organic layer was dried over anhydrous magnesium sulfate. The solvent was removed under reduced pressure, and to the residue, 100 ml of toluene and p-toluene-sulfonic acid monohydrate (2 mmol) were added. The solution was then refluxed for 5 hours, while water produced was removed.

After cooling, the solution was sufficiently washed with water, and then dried over anhydrous magnesium sulfate. The solvent was removed under reduced pressure, and the residue was purified by column chromatography (toluene) to obtain 4-(2,3-difluoro-4-(4-propylcyclohexyl)phenyl) cyclohex-3-enone (29 mmol). To the thus obtained product, 50 ml of ethanol and 1 g of Raney nickel were added, followed by stirring under a hydrogen atmosphere for 5 hours.

After it was confirmed that the absorption of the hydrogen gas stopped, the catalyst was removed by filtration. The filtrate was concentrated to obtain 4-(2,3-difluoro-4-(4-propylcyclohexyl)phenyl)cyclohexanone (25 mmol). This product was a mixture of a cis form and a trans form, but it was used in the next reaction as it was.

A mixture of methoxymethyltriphenylphosphonium chloride (27 mmol), t-BuOK (28 mmol) and 50 ml of THF was stirred at room temperature for 1 hour to obtain a red solution. Next, 80 ml of a THF solution containing 4-(2,3-difluoro-4-(4-propylcyclohexyl)phenyl)cyclohexanone (25 mmol) was added at SoC or less, followed by stirring for 2 hours. The solvent was removed under reduced pressure, and 200 ml of heptane was added to the residue. Afterward, the precipitated crystals were removed by filtration, and the resulting filtrate was then concentrated to obtain an enol ether.

Furthermore, a mixture of the enol ether (25 mmol), 60 ml of THF and 60 ml of 6M hydrochloric acid was stirred at room temperature overnight. The solution was extracted with 100 ml of toluene, and the solvent was removed under reduced pressure. The resulting residue was purified through column chromatography (toluene) to obtain 4-(2,3-difluoro-4-(4-propylcyclohexyl)phenyl)cyclohexanecarboaldehyde (19 mmol).

To a mixture of 4-(2,3-difluoro-4-(4-propylcyclohexyl) phenyl)cyclohexanecarboaldehyde (19 mmol), triphenylphosphine (22 mmol) and 70 ml of dry DMF, 60 ml of a DMF solution containing sodium chlorodifluoroacetate (23 mmol) was added dropwise at about 100° C. After the completion of the dropping, the solution was stirred for 30 minutes, while the same temperature was maintained. After the solution was cooled to room temperature, 100 ml of toluene was added, followed by extraction. The solvent was removed, and the resulting residue was purified by repeating column chromatography (a toluene-heptane mixing solvent) and then recrystallization (heptane) to obtain the desired compound (3.5 mmol). Its structure was properly supported by spectrum data.

In accordance with the procedure of Example 2, the compounds represented by the following formula (1-2) were prepared.

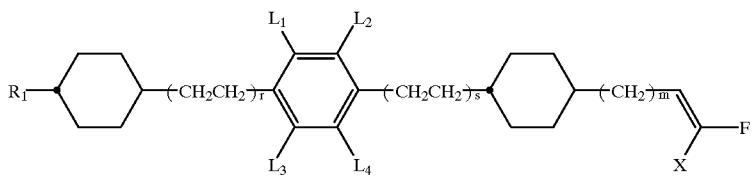

(1-2)

Typically, the compounds shown in Tables 7 to 10 were prepared.

TABLE 7

| r | s | R₁ | L1 | L2 | L3 | L4 | m | X |
|---|---|---|---|---|---|---|---|---|
| 0 | 0 | $C_3H_7$ | H | H | H | H | 0 | H |
| 0 | 0 | $C_5H_{11}$ | H | H | H | H | 0 | H |
| 0 | 0 | $C_3H_7$ | H | H | H | H | 0 | F |
| 0 | 0 | $C_5H_{11}$ | H | H | H | H | 0 | F |
| 0 | 0 | $CH_2$=CH | H | H | H | H | 0 | F |
| 0 | 0 | $C_3H_7$ | F | H | H | H | 0 | F |
| 0 | 0 | $C_3H_7$ | H | F | H | H | 0 | F |
| 0 | 0 | $C_3H_7$ | F | F | H | H | 0 | F |
| 0 | 0 | $C_5H_{11}$ | F | F | H | H | 0 | F *2) |
| 0 | 0 | $C_3H_7$ | F | F | F | H | 0 | F |
| 0 | 0 | $C_3H_7$ | H | H | H | H | 2 | F |
| 0 | 0 | $C_3H_7$ | F | H | H | H | 2 | F |
| 0 | 0 | $C_3H_7$ | H | F | H | H | 2 | F |
| 0 | 0 | $C_3H_7$ | F | F | H | H | 2 | F |
| 0 | 0 | $C_3H_7$ | H | H | H | H | 4 | F |

*2) C 95.3 N 113.2 I

TABLE 8

| r | s | R₁ | L1 | L2 | L3 | L4 | m | X |
|---|---|---|---|---|---|---|---|---|
| 1 | 0 | $C_3H_7$ | H | H | H | H | 0 | H |
| 1 | 0 | $C_5H_{11}$ | H | H | H | H | 0 | H |
| 1 | 0 | $C_3H_7$ | H | H | H | H | 0 | F *3) |
| 1 | 0 | $C_5H_{11}$ | H | H | H | H | 0 | F |
| 1 | 0 | $CH_2$=CH | H | H | H | H | 0 | F |
| 1 | 0 | $C_3H_7$ | F | H | H | H | 0 | F |
| 1 | 0 | $C_3H_7$ | H | F | H | H | 0 | F |
| 1 | 0 | $C_3H_7$ | F | F | H | H | 0 | F |
| 1 | 0 | $C_5H_{11}$ | F | F | H | H | 0 | F |
| 1 | 0 | $C_3H_7$ | F | F | F | H | 0 | F |
| 1 | 0 | $C_3H_7$ | H | H | H | H | 2 | F |
| 1 | 0 | $C_3H_7$ | F | H | H | H | 2 | F |
| 1 | 0 | $C_3H_7$ | H | F | H | H | 2 | F |
| 1 | 0 | $C_3H_7$ | F | F | H | H | 2 | F |
| 1 | 0 | $C_3H_7$ | H | H | H | H | 4 | F |

*3) C 54.2 S 80.4 N 120.3 I

TABLE 9

| r | s | R₁ | L1 | L2 | L3 | L4 | m | X |
|---|---|---|---|---|---|---|---|---|
| 0 | 1 | $C_3H_7$ | H | H | H | H | 0 | H |
| 0 | 1 | $C_5H_{11}$ | H | H | H | H | 0 | H |
| 0 | 1 | $C_3H_7$ | H | H | H | H | 0 | F |
| 0 | 1 | $C_5H_{11}$ | H | H | H | H | 0 | F |
| 0 | 1 | $CH_2$=CH | H | H | H | H | 0 | F |
| 0 | 1 | $C_3H_7$ | F | H | H | H | 0 | F |
| 0 | 1 | $C_3H_7$ | H | F | H | H | 0 | F |
| 0 | 1 | $C_3H_7$ | F | F | H | H | 0 | F |
| 0 | 1 | $C_5H_{11}$ | F | F | H | H | 0 | F |
| 0 | 1 | $C_3H_7$ | F | F | F | H | 0 | F |
| 0 | 1 | $C_3H_7$ | H | H | H | H | 2 | F |
| 0 | 1 | $C_3H_7$ | F | H | H | H | 2 | F |
| 0 | 1 | $C_3H_7$ | H | F | H | H | 2 | F |
| 0 | 1 | $C_3H_7$ | F | F | H | H | 2 | F |
| 0 | 1 | $C_3H_7$ | H | H | H | H | 4 | F |

TABLE 10

| r | s | R₁ | L1 | L2 | L3 | L4 | m | X |
|---|---|---|---|---|---|---|---|---|
| 1 | 1 | $C_3H_7$ | H | H | H | H | 0 | H |
| 1 | 1 | $C_5H_{11}$ | H | H | H | H | 0 | H |
| 1 | 1 | $C_3H_7$ | H | H | H | H | 0 | F |
| 1 | 1 | $C_5H_{11}$ | H | H | H | H | 0 | F |
| 1 | 1 | $CH_2$=CH | H | H | H | H | 0 | F |

TABLE 10-continued

| r | s | R₁ | L1 | L2 | L3 | L4 | m | X |
|---|---|---|---|---|---|---|---|---|
| 1 | 1 | $C_3H_7$ | F | H | H | H | 0 | F |
| 1 | 1 | $C_3H_7$ | H | F | H | H | 0 | F |
| 1 | 1 | $C_3H_7$ | F | F | H | H | 0 | F |
| 1 | 1 | $C_5H_{11}$ | F | F | H | H | 0 | F |
| 1 | 1 | $C_3H_7$ | F | F | F | H | 0 | F |
| 1 | 1 | $C_3H_7$ | H | H | H | H | 2 | F |
| 1 | 1 | $C_3H_7$ | F | H | H | H | 2 | F |
| 1 | 1 | $C_3H_7$ | H | F | H | H | 2 | F |
| 1 | 1 | $C_3H_7$ | F | F | H | H | 2 | F |
| 1 | 1 | $C_3H_7$ | H | H | H | H | 4 | F |

Example 3

Preparation of 4-(4-(4-(4-pentylphenyl)butyl)yclohexyl)-1-(2,2-difluoroethenyl)cyclohexane [a compound of the general formula (1) in which $R_1$=a pentyl group, a ring B=1,4-phenylene, a ring C=1,4-cyclohexylene, $Z_2$=1,4-butylene, $Z_3$=a single bond, p=0, q=1, m=0, and X=a fluorine atom]

A mixture of methoxymethyltriphenylphosphonium chloride (55 mmol), t-BuOK (58 mmol) and 100 ml of THF was stirred at room temperature for 1 hour to obtain a red solution. Next, 100 ml of a THF solution containing 4-(4-(4-(4-pentylphenyl)butyl)cyclohexyl)cyclohexanone (50 mmol) prepared from 4-(4-pentylphenyl)butyl bromide and bicyclohexanedione=monoethylene ketal in accordance with a process of Japanese Patent Application Laid-open No. 211711/1994 was added at 5° C. or less, followed by stirring for 2 hours. The solvent was removed under reduced pressure, and 400 ml of heptane was added to the residue. Afterward, the precipitated crystals were removed by filtration, and the resulting filtrate was then concentrated to obtain an enol ether.

Furthermore, a mixture of the enol ether, 100 ml of THF and 120 ml of 6M hydrochloric acid was stirred at room temperature overnight. The solution was extracted with 100 ml of toluene, and the solvent was removed under reduced pressure. The resulting residue was purified through column chromatography (toluene) to obtain 4-(4-(4-(4-pentylphenyl)butyl)cyclohexyl)cyclohexanecarboaldehyde (42 mmol).

To a mixture of 4-(4-(4-(4-pentylphenyl)butyl)cyclohexyl)cyclohexanecarboaldehyde (42 mmol), triphenylphosphine (45 mmol) and 140 ml of dry DMF, 150 ml of a DMF solution containing sodium chlorodifluoroacetate (47 mmol) was added dropwise at about 100° C. After the completion of the dropping, the solution was stirred for 30 minutes, while the same temperature was maintained. After the solution was cooled to room temperature, 200 ml of toluene was added, followed by extraction. The solvent was removed, and the resulting residue was purified by column chromatography (a toluene-heptane mixing solvent) and then recrystallization (ethanol-benzene) to obtain the desired compound (21 mmol). Its structure was properly supported by spectrum data.

In accordance with the procedure of Example 3, the compounds represented by the following formula (1-3) were prepared.

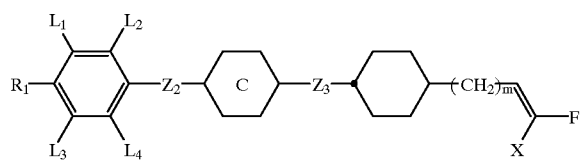
(1-3)

Typically, the compounds shown in Tables 11 to 14 were prepared.

TABLE 11

| Z2 Z3' | C | R1 | L1 | L2 | L3 | L4 | m | X |
|---|---|---|---|---|---|---|---|---|
| —CH$_2$CH$_2$ | cyclohexyl | C$_3$H$_7$ | H | H | H | H | 0 | F |
| —CH$_2$CH$_2$ | dioxane | C$_3$H$_7$ | H | H | H | H | 0 | F |
| —CH$_2$CH$_2$ | cyclohexyl | C$_3$H$_7$ | F | H | H | H | 0 | F |
| —CH$_2$CH$_2$ | cyclohexyl | C$_3$H$_7$ | F | F | H | H | 0 | F |
| —CH$_2$CH$_2$ | phenyl | allyl | H | H | H | H | 2 | F |
| —CH$_2$CH$_2$ | F-phenyl | C$_3$H$_7$ | H | H | H | H | 0 | F |
| —CH$_2$CH$_2$ | F-phenyl | C$_3$H$_7$ | H | F | H | H | 2 | F |
| —CH$_2$O | cyclohexyl | C$_3$H$_7$ | H | H | H | H | 0 | F |
| —CH$_2$O | phenyl | C$_5$H$_{11}$ | H | H | H | H | 0 | F |

TABLE 11-continued

| Z2 Z3' | C | R1 | L1 | L2 | L3 | L4 | m | X |
|---|---|---|---|---|---|---|---|---|
| —OCH$_2$ | cyclohexyl | C$_3$H$_7$ | H | H | H | H | 0 | F |
| —OCH$_2$ | cyclohexyl | C$_3$H$_7$ | F | H | H | H | 0 | F |
| —OCH$_2$ | phenyl | C$_3$H$_7$ | H | H | H | H | 0 | F |

TABLE 12

| Z2 | Z3 | C | R1 | L1 | L2 | L3 | L4 | m | X |
|---|---|---|---|---|---|---|---|---|---|
| (CH$_2$)$_4$ | — | cyclohexyl | C$_3$H$_7$ | H | H | H | H | 0 | F |
| (CH$_2$)$_4$ | — | dioxane | C$_3$H$_7$ | H | H | H | H | 0 | F |
| (CH$_2$)$_4$ | — | cyclohexyl | C$_3$H$_7$ | F | H | H | H | 0 | F |
| (CH$_2$)$_4$ | — | cyclohexyl | C$_3$H$_7$ | F | F | H | H | 0 | F |
| (CH$_2$)$_4$ | — | phenyl | C$_3$H$_7$ | H | H | H | H | 2 | F |
| (CH$_2$)$_4$ | — | F-phenyl | C$_3$H$_7$ | H | H | H | H | 0 | F |
| (CH$_2$)$_4$ | — | F-phenyl | C$_3$H$_7$ | H | F | H | H | 2 | F |

TABLE 13

| Z2 | Z3 |  C | R₁ | L1 | L2 | L3 | L4 | m | X |
|---|---|---|---|---|---|---|---|---|---|
| — | CH₂CH₂ |  | C₃H₇ | H | H | H | H | 0 | H |
| — | CH₂CH₂ |  | C₃H₇ | H | H | H | H | 0 | F |
| — | CH₂CH₂ |  | C₃H₇ | F | H | H | H | 0 | F |
| — | CH₂CH₂ |  | CH₃O | H | H | H | H | 0 | F |
| — | CH₂CH₂ |  | C₃H₇ | H | H | H | H | 2 | F |
| — | CH₂CH₂ |  | C₃H₇ | H | H | H | H | 0 | F |
| — | CH₂CH₂ |  | C₃H₇ | F | H | H | H | 0 | F |
| — | CH₂CH₂ |  | C₃H₇ | F | H | H | F | 0 | F |
| — | CH₂CH₂ |  | C₃H₇ | H | H | H | H | 0 | F |
| — | CH₂CH₂ |  | C₃H₇ | H | F | H | H | 0 | F |
| — | CH₂CH₂ |  | C₃H₇ | H | F | H | H | 0 | F |

TABLE 13-continued

| Z2 | Z3 |  C | R₁ | L1 | L2 | L3 | L4 | m | X |
|---|---|---|---|---|---|---|---|---|---|
| — | CH₂CH₂ |  | C₃H₇ | H | H | H | H | 2 | F |
| — | CH₂O |  | C₃H₇ | H | H | H | H | 0 | F |
| — | CH₂O |  | C₃H₇ | H | H | H | H | 0 | F |
| — | OCH₂ |  | C₃H₇ | F | H | H | H | 4 | F |

TABLE 14

| Z2 | Z3 |  C | R₁ | L1 | L2 | L3 | L4 | m | X |
|---|---|---|---|---|---|---|---|---|---|
| — | (CH₂)₄ |  | C₃H₇ | H | H | H | H | 0 | H |
| — | (CH₂)₄ |  | C₃H₇ | H | H | H | H | 0 | F |
| — | (CH₂)₄ |  | C₃H₇ | F | H | H | H | 0 | F |
| — | (CH₂)₄ |  | CH₃O | H | H | H | H | 0 | F |
| — | (CH₂)₄ |  | C₃H₇ | H | H | H | H | 2 | F |
| — | (CH₂)₄ |  | C₃H₇ | H | H | H | H | 0 | F |
| — | (CH₂)₄ |  | C₃H₇ | F | H | H | H | 0 | F |
| — | (CH₂)₄ |  | C₃H₇ | F | H | H | F | 0 | F |

TABLE 14-continued

| Z2 | Z3 | ![C ring] | R₁ | L1 | L2 | L3 | L4 | m | X |
|---|---|---|---|---|---|---|---|---|---|
| — | (CH₂)₄ | phenyl with F | C₃H₇ | H | H | H | H | 0 | F |
| — | (CH₂)₄ | phenyl with F | C₃H₇ | H | F | H | H | 0 | F |
| — | (CH₂)₄ | phenyl with 2F | C₃H₇ | H | F | H | H | 0 | F |
| — | (CH₂)₄ | phenyl with 2F | C₃H₇ | H | H | H | H | 2 | F |

Example 4

Preparation of 4-(2-(4-propylcyclohexyl)ethenyl)-1-(2,2-difluoroethenyl)cyclohexane [a compound of the general formula (1) in which $R_1$=a propyl group, a ring C=1,4-cyclohexylene, $Z_3$=—CH=CH—, p=q=0, m=0, and X=a fluorine atom]

A mixture of ethyl 4-(2-(4-propylcyclohexyl)ethenyl)cyclohexanecarboxylate (20 mmol) and 50 ml of toluene was cooled to −60° C. or less, and a toluene solution (corresponding to 22 mol) of diisobutylaluminum hydride was then added dropwise, followed by gradually raising the temperature of the solution to room temperature.

The reaction product was poured into a 3M hydrochloric acid, and 50 ml of toluene was added, followed by extraction. The resulting organic layer was sufficiently washed, and then dried over anhydrous magnesium sulfate. The solvent was removed under reduced pressure, and the residue was purified through column chromatography (toluene) to obtain 4-(2-(4-propylcyclohexyl)ethenyl)cyclohexanecarboaldehyde (13 mmol).

To a mixture of 4-(2-(4-propylcyclohexyl)ethenyl)cyclohexanecarboaldehyde (13 mmol), triphenylphosphine (15 mmol) and 60 ml of dry DMF, 50 ml of a DMF solution containing sodium chlorodifluoroacetate (18 mmol) was added dropwise at about 100° C. After the completion of the dropping, the solution was stirred for 30 minutes, while the same temperature was maintained. After the solution was cooled to room temperature, 100 ml of toluene was added, followed by extraction. The solvent was removed, and the resulting residue was purified by column chromatography (a toluene-heptane mixing solvent) and then recrystallization (ethanol-benzene) to obtain the desired compound (11 mmol). Its structure was properly supported by spectrum data.

In accordance with the procedure of Example 4, the compounds represented by the following formula (1-4-1) were prepared.

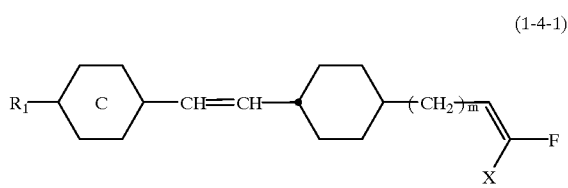

(1-4-1)

Typically, the compounds shown in Table 15 were prepared.

TABLE 15

| C ring | R₁ | m | X |
|---|---|---|---|
| cyclohexyl | CH₃ | 0 | H |
| cyclohexyl | C₃H₇ | 0 | H |
| cyclohexyl | C₂H₅ | 0 | F |
| cyclohexyl | C₅H₁₁ | 0 | F |
| cyclohexyl | CH₂=CH—CH₂— | 1 | F |
| cyclohexyl | C₃H₇ | 2 | F |
| cyclohexyl | C₅H₁₁ | 2 | F |
| cyclohexyl | C₃H₇ | 4 | F |
| cyclohexenyl | C₃H₇ | 0 | F |

TABLE 15-continued

| C R₁ | m | X |
|---|---|---|
| (F-phenyl) C₃H₇ | 0 | F |

In accordance with the procedure of Example 4, the compounds represented by the following formula (1-4-2) were prepared.

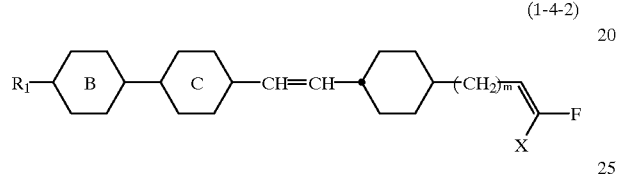

(1-4-2)

Typically, the compounds shown in Table 16 were prepared.

TABLE 16

| B | C | R₁ | m | X |
|---|---|---|---|---|
| hex | hex | C₂H₅ | 0 | H |
| hex | hex | C₃H₇ | 0 | H |
| hex | hex | C₂H₅ | 0 | F |
| hex | hex | C₃H₇ | 0 | F |
| hex | hex | C₅H₁₁ | 0 | F |
| hex | hex | C₂H₅ | 2 | H |
| hex | hex | CH₂=CHCH₂CH₂- | 2 | H |

TABLE 16-continued

| B | C | R₁ | m | X |
|---|---|---|---|---|
| hex | hex | C₂H₅ | 2 | F |
| hex | hex | C₃H₇ | 2 | F |
| hex | hex | C₅H₁₁ | 2 | F |
| hex | hex | C₃H₇ | 4 | F |
| phenyl | hex | C₂H₅ | 0 | H |
| phenyl | hex | C₃H₇ | 0 | H |
| phenyl | hex | C₂H₅ | 0 | F |
| phenyl | hex | C₃H₇ | 0 | F |
| phenyl | hex | C₅H₁₁ | 0 | F |
| phenyl | hex | C₂H₅ | 2 | F |
| phenyl | hex | C₃H₇ | 2 | F |
| phenyl | hex | C₂H₅ | 4 | F |
| F-phenyl | hex | C₃H₇ | 0 | F |

TABLE 16-continued

| B | C | R₁ | m | X |
|---|---|----|---|---|
| F-phenyl | cyclohexyl | $C_3H_7$ | 2 | F |

In accordance with the procedure of Example 4, the compounds represented by the following formula (1-4-3) were prepared.

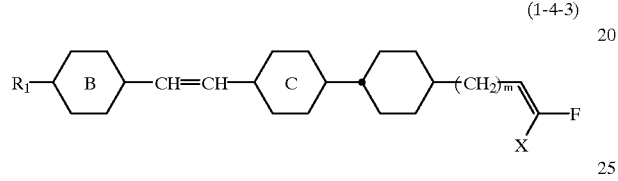

(1-4-3)

Typically, the compounds shown in Table 17 were prepared.

TABLE 17

| B | C | $R_1$ | m | X |
|---|---|-------|---|---|
| cyclohexyl | cyclohexyl | $C_2H_5$ | 0 | H |
| cyclohexyl | cyclohexyl | $C_3H_7$ | 0 | H |
| cyclohexyl | cyclohexyl | $C_2H_5$ | 0 | F |
| cyclohexyl | cyclohexyl | (vinyl) | 0 | F |
| cyclohexyl | cyclohexyl | $C_5H_{11}$ | 0 | F |
| cyclohexyl | cyclohexyl | $C_2H_5$ | 2 | F |
| cyclohexyl | cyclohexyl | $C_3H_7$ | 2 | H |

TABLE 17-continued

| B | C | $R_1$ | m | X |
|---|---|-------|---|---|
| cyclohexyl | cyclohexyl | $C_2H_5$ | 2 | H |
| cyclohexyl | cyclohexyl | $C_3H_7$ | 2 | F |
| cyclohexyl | cyclohexyl | $C_5H_{11}$ | 2 | F |
| cyclohexyl | cyclohexyl | $C_3H_7$ | 4 | F |
| phenyl | cyclohexyl | $C_2H_3$ | 0 | H |
| phenyl | cyclohexyl | $C_3H_7$ | 0 | H |
| phenyl | cyclohexyl | $C_2H_5$ | 0 | F |
| phenyl | cyclohexyl | $C_3H_7$ | 0 | F |
| phenyl | cyclohexyl | $C_5H_{11}$ | 0 | F |
| phenyl | cyclohexyl | $C_2H_5$ | 2 | F |
| phenyl | cyclohexyl | $C_3H_7$ | 2 | F |
| phenyl | cyclohexyl | $C_2H_5$ | 4 | F |
| F-phenyl | cyclohexyl | $C_3H_7$ | 0 | F |

TABLE 17-continued

| B C | | | |
|---|---|---|---|
| | $R_1$ | m | X |
| F─⌬ ─⌬ | $C_3H_7$ | 2 | F |

Example 5

Preparation of 4-(4-(1,2-difluoro-2-(4-propylphenyl) ethenyl)phenyl)-1-(2,2-difluoroethenyl)cyclohexane [a compound of the general formula (1) in which $R_1$=a propyl group, a ring B=a ring C=1,4-phenylene, $Z_2$=—CF=CF—, $Z_3$=a single bond, p=0, q=1, m=0, and X=a fluorine atom]

A hexane solution (corresponding to 27 mmol) of butyl lithium was added at −78° C. to 95 ml of a THF solution containing 4-(4-(1,3-dioxane-2-yl)cyclohexyl)phenyl iodide (30 mmol), followed by stirring at the same temperature for 30 minutes. Next, tetrafluoroethylene (corresponding to 33 mmol) was added thereto through a bubbling tube, and the solution was then stirred at the same temperature for 1 hour.

A hexane solution (corresponding to 27 mmol) of butyl lithium was added at −78° C. to 95 ml of a THF solution of 4-propylphenyl iodide (30 mmol), followed by stirring at the same temperature for 30 minutes. This solution was gradually added dropwise to the above solution, and the temperature of the solution was then raised to room temperature. Next, 50 ml of methanol and 50 ml of water were slowly added in this order, and the solvent was removed under reduced pressure. The resulting residue was purified through column chromatography (toluene) to obtain 2-(4-(4-(1,2-difluoro-2-( 4-propylphenyl)ethenyl)phenyl)cyclohexyl)-1, 3-dioxane (12 mmol).

A mixture of 2-(4-(4-(1,2-difluoro-2-(4-propylphenyl) ethenyl)phenyl)cyclohexyl)-1,3-dioxane (12 mmol), 40 ml of toluene and 20 ml of formic acid was stirred at 50° C. for 1 hour. Afterward, the temperature of the solution was raised to room temperature, and solution was sufficiently washed with water, and then dried over anhydrous magnesium sulfate. The solvent was removed under reduced pressure, and the residue was purified through column chromatography (toluene) to obtain 4-(4-(1,2-difluoro-2-(4-propylphenyl)ethenyl)phenyl)cyclohexanecaboaldehyde (8 mmol).

To a mixture of 4-(4-(1,2-difluoro-2-(4-propylphenyl) ethenyl)phenyl)cyclohexanecaboaldehyde (8 mmol), triphenylphosphine (9 mmol) and 40 ml of dry DMF, 30 ml of a DMF solution containing sodium chlorodifluoroacetate (9 mmol) was added dropwise at about 80° C. After the completion of the dropping, the solution was cooled to room temperature, 50 ml of toluene was added, followed by extraction. The solvent was removed, and the resulting residue was purified by column chromatography (a toluene-heptane mixing solvent) and then recrystallization (ethanol-benzene) to obtain the desired compound (2 mmol). Its structure was properly supported by spectrum data.

In accordance with the procedure of Example 5, the compounds represented by the following formula (1-4-4) were prepared.

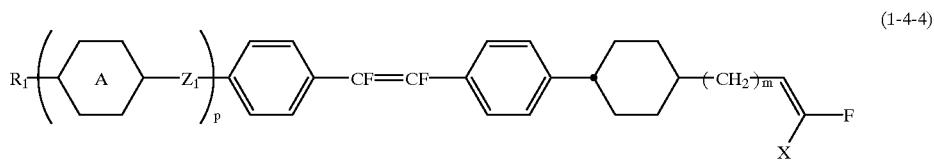

(1-4-4)

Typically, the compounds shown in Tables 18 and 19 were prepared.

TABLE 18

| $R_1$ | m | X |
|---|---|---|
| $CH_3$ | 0 | H |
| $C_2H_5$ | 0 | H |
| $C_3H_7$ | 0 | H |
| $C_4H_9$ | 0 | H |
| $C_5H_{11}$ | 0 | H |
| $CH_3$ | 0 | F |
| $C_2H_5$ | 0 | F |
| $C_3H_7$ | 0 | F |
| $C_4H_9$ | 0 | F |
| $C_5H_{11}$ | 0 | F |
| $C_4H_9$ | 1 | F |
| $C_3H_7$ | 2 | F |
| $C_2H_5$ | 3 | F |
| $C_3H_7$ | 4 | F | p = 0

TABLE 19

| A ─$Z_1$ | | | |
|---|---|---|---|
| | $R_1$ | m | X |
| ⌬ | $C_3H_7$ | 0 | F |
| ⌬ | $C_3H_7$ | 2 | F |
| ⌬(O,O) | $C_3H_7$ | 0 | F |

TABLE 19-continued

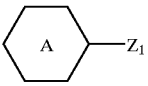

| A-Z₁ | R₁ | m | X |
|---|---|---|---|
| cyclohexyl-CH₂CH₂- | C₃H₇ | 0 | F |
| cyclohexyl-(CH₂)₄- | C₃H₇ | 0 | F |
| cyclohexenyl | C₃H₇ | 0 | H |
| cyclohexenyl | C₃H₇ | 0 | F |
| cyclohexenyl | C₃H₇ | 0 | F |
| phenyl-CH₂CH₂- | C₂H₅ | 0 | F |
| fluorophenyl | C₂H₅ | 0 | F | p = 1 anhydrous magnesium sulfate. The solvent was removed under reduced pressure, and the residue was purified through column chromatography (toluene-heptane) to obtain a thione ester (23 mmol).

Diethylaminosulfur trifluoride (25 mmol) was added to 30 ml of a methylene chloride solution containing the thione ester (20 mmol), followed by stirring at room temperature for 2 hours. Afterward, 50 ml of water and 30 ml of toluene were added, and the solution was stirred and the separated organic layer was then concentrated under reduced pressure. The residue was recrystallized from ether to obtain 2-(4-(4-(4-propylphenyl)difluoromethoxy)phenyl)cyclohexyl-1,3-dioxane (12 mmol).

A mixture of 2-(4-(4-(4-propylphenyl)difluoromethoxy) phenyl)cyclohexyl-1,3-dioxane (12 mmol), 50 ml of toluene and 10 ml of formic acid was refluxed for 30 minutes. The solution was cooled to room temperature, and then washed three times with 30 ml of water. The solvent was removed under reduced pressure, and the residue was then purified through column chromatography (toluene) to obtain (4-(4-(4-propylphenyl)difluoromethoxy)phenyl) cyclohexanecarboaldehyde (10 mmol).

To a mixture of (4-(4-(4-propylphenyl)difluoromethoxy) phenyl)cyclohexanecarboaldehyde (10 mmol), triphenylphosphine (11 mmol) and 40 ml of dry DMF, 30 ml of a DMF solution containing sodium chlorodifluoroacetate (12 mmol) was added dropwise at about 80° C. After the completion of the dropping, the solution was cooled to room temperature, 50 ml of toluene was added, followed by extraction. The solvent was removed, and the resulting residue was purified by column chromatography (a toluene-heptane mixing solvent) and then recrystallization (ethanol-benzene) to obtain the desired compound (6 mmol) Its structure was properly supported by spectrum data.

In accordance with the procedure of Example 6, the compounds represented by the following formula (1-4-5) were prepared.

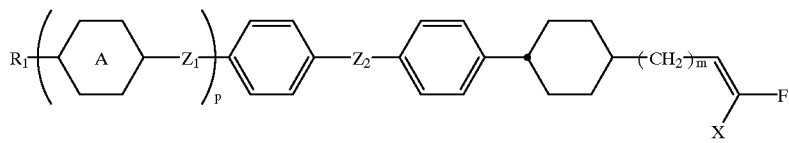

(1-4-5)

Example 6

Preparation of 4-(4-(4-propylphenyldifluoromethoxy) phenyl)-1-(2,2-difluoroethenyl)cyclohexane [a compound of the general formula (1) in which $R_1$=a propyl group, a ring B=a ring C=1,4-phenylene, $Z_2$=—CF₂O—, $Z_3$=a single bond, p=0, q=1, m=0, and X=a fluorine atom]

A mixture of 4-propylphenyldithiocarboxylic acid (50 mmol), thionyl chloride (55 mmol) and 100 ml of toluene was stirred at 50° C. for 1 hour. Afterward, excessive thionyl chloride was removed under reduced pressure to obtain an acid chloride as a residue. Next, this acid chloride was added to a mixture of 4-(4-(1,3-dioxane-2-yl)cyclohexyl)phenol (60 mmol) and 100 ml of pyridine, and the solution was then stirred at 45° C. for 5 hours. The temperature of the solution was returned to room temperature, and extraction was then carried out with 50 ml of toluene. The resulting organic layer was sufficiently washed with water, and then dried over Typically, the compounds shown in Tables 20 and 21 were prepared.

TABLE 20

| $Z_2$ | $R_1$ | m | X |
|---|---|---|---|
| CF₂O | C₂H₅ | 0 | H |
| CF₂O | C₃H₇ | 0 | H |
| CF₂O | C₂H₅ | 0 | F |
| CF₂O | C₃H₇ | 0 | F |
| CF₂O | C₂H₅ | 2 | F |
| CF₂O | C₃H₇ | 2 | F |
| CF₂O | C₅H₁₁ | 2 | F |
| CF₂O | C₃H₇ | 4 | F |
| OCF₂ | C₂H₅ | 0 | H |
| OCF₂ | C₃H₇ | 0 | H |

TABLE 20-continued

| $Z_2$ | $R_1$ | m | X |
|---|---|---|---|
| $OCF_2$ | $C_2H_5$ | 0 | F |
| $OCF_2$ | $C_3H_7$ | 0 | F |
| $OCF_2$ | $C_2H_5$ | 2 | F |
| $OCF_2$ | $C_3H_7$ | 2 | F |
| $OCF_2$ | $C_5H_{11}$ | 2 | F |
| $OCF_2$ | $C_3H_7$ | 4 | F | p = 0

TABLE 21

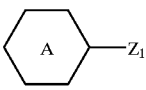

| $Z_2$ | (ring A) | $R_1$ | m | X |
|---|---|---|---|---|
| $CF_2O$ | 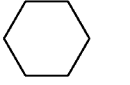 | $C_3H_7$ | 0 | F |
| $CF_2O$ | 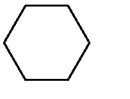 | $C_3H_7$ | 2 | F |
| $CF_2O$ | 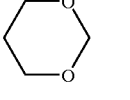 | $C_3H_7$ | 0 | F |
| $CF_2O$ | 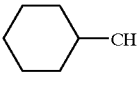 | $C_3H_7$ | 0 | F |
| $CF_2O$ |  | $C_3H_7$ | 0 | F |
| $CF_2O$ | 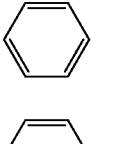 | $C_3H_7$ | 0 | F |
| $CF_2O$ | 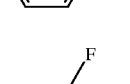 | $C_3H_7$ | 2 | F |
| $CF_2O$ | 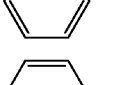 | $C_3H_7$ | 0 | F |
| $CF_2O$ |  | $C_3H_7$ | 0 | F |
| $OCF_2O$ |  | $C_3H_7$ | 0 | F |

TABLE 21-continued

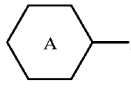

| $Z_2$ | (ring A) | $R_1$ | m | X |
|---|---|---|---|---|
| $OCF_2O$ | 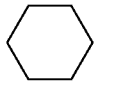 | $C_3H_7$ | 2 | F |
| $OCF_2O$ | 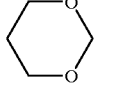 | $C_3H_7$ | 0 | F |
| $OCF_2O$ | 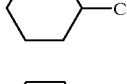 | $C_3H_7$ | 0 | F |
| $OCF_2O$ | 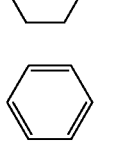 | $C_3H_7$ | 0 | F |
| $OCF_2O$ |  | $C_3H_7$ | 0 | F |
| $OCF_2O$ | 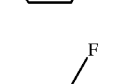 | $C_3H_7$ | 2 | F |
| $OCF_2O$ | 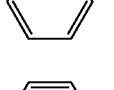 | $C_3H_7$ | 0 | F |
| $OCF_2O$ | 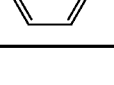 | $C_3H_7$ | 0 | F | p = 1

Example 7

Preparation of 4-(2-methyl-2-(4-propylcyclohexyl)ethenyl)-1-(2,2-difluoroethenyl)cyclohexane [a compound of the general formula (1) in which $R_1$=a propyl group, a ring C=1,4-cyclohexylene, $Z_3$=—$CR_2$=CH—, $R_2$=a methyl group, p=q=0, m=0, and X=a fluorine atom]

To a mixture of 4-(2-methyl-2-(4-propylcyclohexyl)ethenyl)cyclohexanecarboaldehyde (20 mmol) prepared in accordance with a process of Example 4, triphenylphosphine (22 mmol) and 100 ml of dry DMF, 70 ml of a DMF solution containing sodium chlorodifluoroacetate (23 mmol) was added dropwise at about 100° C. After the completion of the dropping, the solution was stirred for 30 minutes, while the same temperature was maintained. After the solution was cooled to room temperature, 100 ml of toluene was added, followed by extraction. The solvent was removed, and the resulting residue was purified by column chromatography (a toluene-heptane mixing solvent) and then recrystallization (ethanol-benzene) to obtain the desired compound (15 mmol). Its structure was properly supported by spectrum data.

In accordance with the procedure of Example 7, the compounds represented by the following formula (1-4-6) were prepared.

(1-4-6)

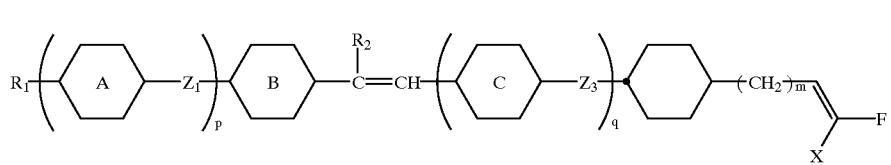

Typically, the compounds shown in Tables 22 to 24 were prepared.

TABLE 22

| B | R₁ | R₂ | m | X |
|---|---|---|---|---|
| cyclohexyl | C₃H₇ | CH₃ | 0 | F |
| cyclohexyl | C₃H₇ | CH₃ | 0 | F |
| cyclohexyl | C₃H₇ | CH₃ | 2 | F |
| cyclohexyl | C₃H₇ | C₂H₅ | 0 | F |
| cyclohexyl | vinyl | CH₃ | 0 | F |
| phenyl | C₃H₇ | CH₃ | 0 | F |
| phenyl | butenyl | C₃H₇ | 2 | F | p = q = 0

TABLE 23

| A–Z₁ | B | R₁ | R₂ | m | X |
|---|---|---|---|---|---|
| phenyl | cyclohexyl | C₃H₇ | CH₃ | 0 | F |

TABLE 23-continued

| A–Z₁ | B | R₁ | R₂ | m | X |
|---|---|---|---|---|---|
| cyclohexyl-(CH₂)₄ | cyclohexyl | C₃H₇ | CH₃ | 0 | F |
| phenyl | dioxanyl | C₃H₇ | CH₃ | 0 | F |
| phenyl | cyclohexyl | C₃H₇ | CH₃ | 2 | F |
| F-phenyl | phenyl | C₃H₇ | CH₃ | 0 | F |
| phenyl | phenyl-vinyl | | CH₃ | 0 | F |
| phenyl | phenyl-butenyl | | CH₃ | 0 | F | p = 1, q = 0

TABLE 24

| B | cyclohexyl-(CH₂)₄ | R₁ | R₂ | m | X |
|---|---|---|---|---|---|
| cyclohexyl | cyclohexyl | C₃H₇ | CH₃ | 0 | F |
| cyclohexyl | cyclohexyl | C₃H₇ | CH₃ | 2 | F |

TABLE 24-continued

| Structure | R₁ | R₂ | m | X |
|---|---|---|---|---|
| B—⟨cyclohexyl⟩—(CH₂)₄ | C₃H₇ | CH₃ | 4 | F |
| ⟨phenyl⟩—⟨phenyl⟩ | C₅H₁₁ | C₂H₅ | 0 | F |
| ⟨phenyl⟩—⟨phenyl⟩ | C₃H₇ | CH₃ | 0 | F |
| ⟨phenyl⟩—⟨cyclohexyl⟩—CH₂CH₂ | | | | |
| ⟨phenyl⟩—⟨phenyl⟩—CH=CH— | | CH₃ | 0 | F |
| ⟨phenyl⟩—⟨phenyl⟩—CH=CH—CH₂— | | CH₃ | 0 | F | p = 0, q = 1

In accordance with the procedure of Example 7, the compounds represented by the following formula (1-4-7) were prepared.

$$R_1 {\left(\!\!\left\langle A \right\rangle\!\!- Z_1\!\!\right)}\!\!\left(\!\!\left\langle B \right\rangle\!\!- C\!\!=\!\!\overset{R_2}{\underset{}{C}}\!H\!\!\right)\!\!\left(\!\!\left\langle C \right\rangle\!\!- Z_3\!\!\right)_q\!\!-\!\!\left\langle \text{cyclohexyl} \right\rangle\!\!-\!\!(CH_2)_m\!\!-\!\!\underset{X}{\overset{}{C}}\!\!=\!\!\underset{F}{\overset{}{C}}H \quad (1\text{-}4\text{-}7)$$

Typically, the compounds shown in Tables 25 to 27 were prepared.

TABLE 25

| Structure | R₁ | R₂ | m | X |
|---|---|---|---|---|
| B—⟨phenyl⟩ | C₃H₇ | CH₃ | 0 | H |

TABLE 25-continued

| Structure | R₁ | R₂ | m | X |
|---|---|---|---|---|
| B—⟨phenyl⟩ | C₃H₇ | CH₃ | 0 | F |
| ⟨phenyl⟩ | C₃H₇ | CH₃ | 2 | F |
| ⟨phenyl⟩ | C₃H₇ | C₂H₅ | 0 | F |
| ⟨phenyl⟩—CH=CH— | | CH₃ | 0 | F |
| ⟨phenyl⟩ | C₃H₇ | CH₃ | 0 | F |

TABLE 25-continued

| Structure | R₁ | R₂ | m | X |
|---|---|---|---|---|
| B—⟨phenyl⟩ | | | | |
| ⟨phenyl⟩—CH=CH—CH₂— | | C₃H₇ | 2 | F | p = q = 0

TABLE 26
| A —Z₁ B | | R₁ | R₂ | m | X |
|---|---|---|---|---|---|
| 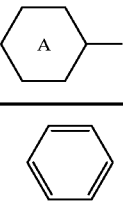 | 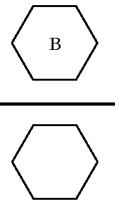 | C₃H₇ | CH₃ | 0 | F |
| 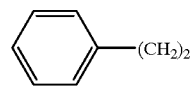 |  | C₃H₇ | CH₃ | 0 | F |
|  | 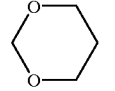 | C₃H₇ | CH₃ | 0 | F |
|  |  | C₃H₇ | CH₃ | 2 | F |
| 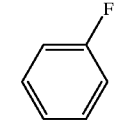 | 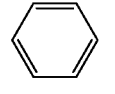 | C₃H₇ | CH₃ | 0 | F |
|  |  |  | CH₃ | 0 | F |
|  |  | 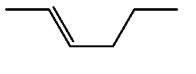 | CH₃ | 0 | F |
p = 1, q = 0
TABLE 27
| B C —Z₃ | | R₁ | R₂ | m | X |
|---|---|---|---|---|---|
| 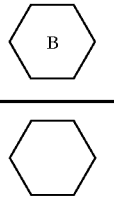 | 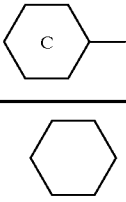 | C₃H₇ | CH₃ | 0 | F |
| 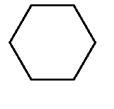 | 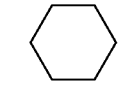 | C₃H₇ | CH₃ | 2 | F |
| 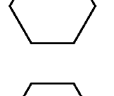 | 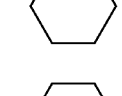 | C₃H₇ | CH₃ | 4 | F |
| 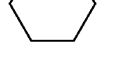 | 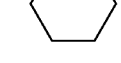 | C₅H₁₁ | C₂H₅ | 0 | F |

TABLE 27-continued

| B | C-Z₃ | | R₁ | R₂ | m | X |
|---|---|---|---|---|---|---|
| hexagon | hexagon-CH₂CH₂ | | C₃H₇ | CH₃ | 0 | F |
| hexagon | hexagon | allyl | | CH₃ | 0 | F |
| hexagon | hexagon | butenyl | | CH₃ | 0 | F | p = 0, q = 1

In accordance with the procedure of Examples 1 to 7, the compounds represented by the above formula (1) were prepared.

Typically, the compounds shown in Tables 28 to 32 were prepared.

TABLE 28

| C | Z₃ | R₁ | m | X |
|---|---|---|---|---|
| hexagon | —propyl-O— | C₃H₇ | 0 | H |
| hexagon | —propyl-O— | C₃H₇ | 0 | F |
| hexagon | —propyl-O— | C₃H₇ | 0 | F |
| hexagon | —propyl-O— | C₃H₇ | 2 | F |
| hexagon | —propyl-O— butenyl | | 2 | F |
| benzene | —propyl-O— | C₃H₇ | 0 | F |
| F-benzene | —propyl-O— | C₅H₁₁ | 0 | F |

TABLE 28-continued

| C | Z₃ | R₁ | m | X |
|---|---|---|---|---|
| hexagon | —O-propyl— | C₃H₇ | 0 | H |
| hexagon | —O-propyl— | C₃H₇ | 0 | F |
| hexagon | —O-propyl— | C₃H₇ | 0 | F |
| hexagon | —O-propyl— | C₃H₇ | 2 | F |
| hexagon | —O-propyl— | butenyl | 2 | F |
| benzene | —O-propyl— | C₃H₇ | 0 | F |
| F-benzene | —O-propyl— | C₅H₁₁ | 0 | F | p = q = 0

TABLE 29

| C | Z₃ | R₁ | m | X |
|---|----|----|---|---|
| hexane | -CH=CH-CH₂- | C₃H₇ | 0 | H |
| hexane | -CH=CH-CH₂- | C₃H₇ | 0 | F |
| hexane | -CH=CH-CH₂- | C₃H₇ | 0 | F |
| hexane | -CH=CH-CH₂- | C₃H₇ | 2 | F |
| hexane | -CH=CH-CH₂- | -CH₂-CH=CH-CH₂- | 2 | F |
| benzene | -CH=CH-CH₂- | C₃H₇ | 0 | F |
| fluorobenzene | -CH₂-CH=CH-CH₂- | C₅H₁₁ | 0 | F |
| hexane | -CH₂-CH=CH- | C₃H₇ | 0 | H |

TABLE 29-continued

| C | Z₃ | R₁ | m | X |
|---|----|----|---|---|
| hexane | -CH₂-CH=CH-CH₂- | C₃H₇ | 0 | F |
| hexane | -CH₂-CH=CH-CH₂- | C₃H₇ | 0 | F |
| hexane | -CH₂-CH=CH-CH₂- | C₃H₇ | 2 | F |
| hexane | -CH₂-CH=CH-CH₂- | -CH₂-CH=CH-CH₂- | 2 | F |
| benzene | -CH₂-CH=CH-CH₂- | C₃H₇ | 0 | F |
| fluorobenzene | -CH₂-CH=CH-CH₂- | C₅H₁₁ | 0 | F |

$p = q = 0$

TABLE 30

| B | C | R₁ | Z₂ | Z₃ | m | X |
|---|---|----|----|----|---|---|
| hexane | hexane | C₃H₇ | — | -CH₂-CH₂-O- | 0 | F |
| hexane | hexane | C₃H₇ | — | -CH₂-CH₂-O- | 2 | F |
| benzene | hexane | C₃H₇ | — | -CH₂-CH₂-O- | 0 | F |

TABLE 30-continued

| B | C | R₁ | Z₂ | Z₃ | m | X |
|---|---|----|----|----|---|---|
| | | | — | | 0 | F |
| | | C₃H₇ | — | | 0 | F |
| | | C₃H₇ | — | | 0 | F |
| | | C₃H₇ | — | | 2 | F |
| | | C₃H₇ | — | | 0 | F |
| | | | — | | 0 | F |
| | | C₃H₇ | — | | 0 | F | p = 0, q = 1

TABLE 31

| B | C | R₁ | Z₂ | Z₃ | m | X |
|---|---|----|----|----|---|---|
| | | C₃H₇ | — | | 0 | F |
| | | C₃H₇ | — | | 2 | F |
| | | C₃H₇ | — | | 0 | F |
| | | | — | | 0 | F |

TABLE 31-continued

| B | C | R₁ | Z₂ | Z₃ | m | X |
|---|---|----|----|----|---|---|
| ⬡ | ⬡ | C₃H₇ | — | ╱╲╱ | 0 | F |
| ⬡ | ⬡ | C₃H₇ | — | ╱╲╱ | 0 | F |
| ⬡ | ⬡ | C₃H₇ | — | ╱╲╱ | 2 | F |
| ⬡ | ⬡ | C₃H₇ | — | ╱╲╱ | 0 | F |
| ⬡ | ⬡ | ╱╲╱ | — | ╱╲╱ | 0 | F |
| ⬡ | ⬡ | C₃H₇ | — | ╱╲╱ | 0 | F |

$p = 0, q = 1$

TABLE 32

| A | B | C | R₁ | Z₁ | Z₂ | Z₃ | m | X |
|---|---|---|----|----|----|----|---|---|
| ⬡ | ⬡ | ⬡ | C₃H₇ | — | — | ╱╲╱O— | 0 | F |
| ⬡ | ⬡ | ⬡ | ╱╲ | — | — | ╱╲╱O— | 0 | F |
| ⬡ | ⬡ | ⬡ | ╱╲ | — | — | ╱╲╱O— | 0 | F |
| ⬡ | ⬡ | ⬡ | C₃H₇ | — | — | O╱╲╱ | 0 | F |
| ⬡ | ⬡ | ⬡ | ╱╲ | — | — | O╱╲╱ | 0 | F |

TABLE 32-continued

| A B C | R$_1$ | Z$_1$ | Z$_2$ | Z$_3$ | m | X |
|---|---|---|---|---|---|---|
| ⬡⬡⬡ | CH$_2$=CH-CH$_2$- | — | — | -O-CH$_2$- | 0 | F |
| ⬡⬡⬡ | C$_3$H$_7$ | — | — | -CH$_2$-CH=CH- | 0 | F |
| ⬡⬡⬡ | CH$_2$=CH-CH$_2$- | — | — | -CH$_2$-CH=CH- | 0 | F |
| ⬡⬡⬡ | CH$_2$=CH-CH$_2$- | — | — | -CH$_2$-CH=CH- | 0 | F |
| ⬡⬡⬡ | C$_3$H$_7$ | — | — | -CH$_2$-CH=CH- | 0 | F |
| ⬡⬡⬡ | CH$_2$=CH-CH$_2$- | — | — | -CH$_2$-CH=CH- | 0 | F |
| ⬡⬡⬡ | CH$_2$=CH-CH$_2$- | — | — | -CH$_2$-CH=CH- | 0 | F | p = 1

Examples of compositions prepared by the use of the compounds represented by the general formula (1) of the present invention will be described.

However, the compounds which can be used in the examples are represented by symbols which are defined in Table 33 given below. For example, when the hydrogen atoms of trans-1,4-cyclohexylene in the following partial structural formula (w) are substituted by deuterium at positions Q$_1$, Q$_2$ and Q$_3$, it is represented by a symbol H[1D, 2D,3D]. Moreover, when the hydrogen atoms of trans-1,4-cyclohexylene are substituted by deuterium at positions Q$_5$, Q$_6$ and Q$_7$, it is represented by a symbol H[5D,6D,7D]. Thus, the substitution positions of deuterium are shown by the numbers in the brackets [ ].

TABLE 33

Representation of Compounds by Use of Symbols
R—(A$_1$)—Z$_1$— . . . —Z$_n$—(A$_n$)—X

| | Symbol |
|---|---|
| 1) Left Terminal Group R— | |
| C$_n$H$_{2n+1}$— | n— |
| C$_n$H$_{2n+1}$O— | nO— |
| C$_n$H$_{2n+1}$OC$_m$H$_{2m}$— | nOm— |
| CH$_2$=CH— | V— |
| CH$_2$=CHC$_n$H$_{2n}$— | Vn— |

TABLE 33-continued

Representation of Compounds by Use of Symbols
R—(A$_1$)—Z$_1$— . . . —Z$_n$—(A$_n$)—X

| | Symbol |
|---|---|
| C$_n$H$_{2n+1}$CH=CHC$_m$H$_{2m}$— | nVm— |
| C$_2$H$_{2n+1}$CH=CHC$_m$H$_{2m}$CH=CHC$_k$H$_{2k}$— | nVmVk— |
| 2) Ring Structure —(A$_1$)—, (A$_n$)— | Symbol |
| (benzene ring) | B |
| (fluoro-substituted benzene) | B(F) |
| (difluoro-substituted benzene) | B(2F,3F) |

TABLE 33-continued

Representation of Compounds by Use of Symbols
R—(A₁)—Z₁— . . . —Zₙ—(Aₙ)—X

| Structure | Symbol |
|---|---|
| (difluorobenzene ring with F at 2,3 positions) | B(F,F) |
| (cyclohexane ring) | H |
| (pyrimidine ring) | Py |
| (dioxane ring) | D |
| (cyclohexene ring) | Ch |

| 3) Bond Group —Z₁—, —Zₙ— | Symbol |
|---|---|
| —C₂H₄— | 2 |
| —C₄H₈— | 4 |
| —COO— | E |
| —C≡C— | T |
| —CH=CH— | V |
| —CF₂O— | CF2O |
| —OCF₂— | OCF2 |
| —CF=CF— | FVF |
| —C(CH₃)=CH— | V(Me) |

| 4) Right Terminal Group —X | Symbol |
|---|---|
| —F | —F |
| —Cl | —CL |
| —CN | —C |
| —CF₃ | —CF3 |
| —OCF₃ | —OCF3 |
| —OCF₂H | —OCF2H |
| —CₙH₂ₙ₊₁ | —n |
| —OCₙH₂ₙ₊₁ | —On |
| —COOCH₃ | —EMe |
| —CₙH₂ₙCH=CH₂ | —nV |
| —CₘH₂ₘCH=CHCₙH₂ₙ₊₁ | —mVn |
| —CₘH₂ₘCH=CHCₙH₂ₙF | —mVnF |
| —CH=CF₂ | —VFF |
| —CₙH₂ₙCH=CF₂ | —nVFF |
| —C≡C—CN | —TC |

5) Examples of Representation

Ex. 1 3-H2B(F,F)B(F)—F

Ex. 2 3-HB(F)TB-2

(structure: C₃H₇—cyclohexane—C₂H₄—difluorobenzene—difluorobenzene—F)

Ex. 3 IV2-BEB(F,F)—C (structure: C₃H₇—cyclohexane—fluorobenzene—C≡C—benzene—C₂H₅)

(structure: CH₃CH=CHCH₂CH₂—benzene—COO—difluorobenzene—CN)

(w)

(cyclohexane with Q₁–Q₈ labels)

Incidentally, $T_{NI}$ is a temperature at a clearing point; a viscosity η was measured at 20° C.; and an optical anisotropy Δn, a dielectric anisotropy Δε, a threshold voltage $V_{th}$ and a pitch length P of helical twist were measured at 25° C., respectively. In addition, % is based on weight.

Example 8

TABLE 34

| | |
|---|---|
| 5-HB(2F,3F)H—VFF | 5.0% |
| 1V2-BEB(F,F)—C | 5.0% |
| 3-HB—C | 25.0% |
| 1-BTB-3 | 5.0% |
| 2-BTB-1 | 10.0% |
| 3-HH-4 | 11.0% |
| 3-HHB-1 | 11.0% |
| 3-HHB-3 | 4.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |
| CM33 | 0.8 part |
| $T_{NI}$ = 87.5 (° C.) | |
| η = 15.5 (mPa · s) | |
| Δn = 0.162 | |
| Δε = 7.0 | |
| Vth = 2.11 (V) | |
| P = 11 μm | |

Example 9

TABLE 35

| | |
|---|---|
| 5-HBBH—VFF | 3.0% |
| V2-HB—C | 12.0% |
| 1V2-HB—C | 12.0% |
| 3-HB—C | 15.0% |
| 3-H[1D,2D,3D]—C | 9.0% |
| 3-HB(F)—C | 5.0% |
| 2-BTB-1 | 2.0% |
| 3-HH-4 | 8.0% |
| 3-HH—VFF | 6.0% |
| 2-H[1D,2D,3D]HB—C | 3.0% |
| 3-HB—C | 6.0% |
| 3-HB(F)TB-2 | 8.0% |
| 3-H2BTB-2 | 5.0% |
| 3-H2BTB-3 | 2.0% |
| 3-H2BTB-4 | 4.0% |
| $T_{NI}$ = 91.2 (° C.) | |
| $\eta$ = 17.7 (mPa · s) | |
| $\Delta n$ = 0.152 | |
| $\Delta_\epsilon$ = 8.8 | |
| Vth = 1.98 (V) | |

Example 10

TABLE 36

| | |
|---|---|
| 5-HB(2F,3F)H—VFF | 4.0% |
| 5-HBBH—VFF | 4.0% |
| 2O1-BEB(F)—C | 5.0% |
| 3O1-BEB(F)—C | 15.0% |
| 4O1-BEB(F)—C | 13.0% |
| 5O1-BEB(F)—C | 13.0% |
| 2-HHB(F)—C | 15.0% |
| 3-HHB(F)—C | 15.0% |
| 3-HB(F)TB-3 | 4.0% |
| 3-HB(F)TB-4 | 4.0% |
| 3-HHB-1 | 4.0% |
| 3-HHB—O1 | 4.0% |
| $T_{NI}$ = 92.5 (° C.) | |
| $\eta$ = 87.9 (mPa · s) | |
| $\Delta n$ = 0.147 | |
| $\Delta_\epsilon$ = 31.0 | |
| Vth = 0.86 (V) | |

Example 11

TABLE 37

| | |
|---|---|
| 3-BBHH—2VFF | 2.0% |
| 3-BH2H—VFF | 3.0% |
| 5-PyB—F | 4.0% |
| 3-PyB(F)—F | 4.0% |
| 2-BB—C | 5.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O5 | 3.0% |
| 6-PyB—O6 | 3.0% |
| 6-PyB—O7 | 3.0% |
| 6-PyB—O8 | 3.0% |
| 3-PyBB—F | 6.0% |
| 4-PyBB—F | 6.0% |
| 5-PyBB—F | 6.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-3 | 5.0% |
| 3-H2BTB-4 | 5.0% |
| $T_{NI}$ = 94.4 (° C.) | |

TABLE 37-continued

| | |
|---|---|
| $\eta$ = 36.5 (mPa · s) | |
| $\Delta n$ = 0.197 | |
| $\Delta_\epsilon$ = 6.5 | |
| Vth = 2.26 (V) | |

Example 12

TABLE 38

| | |
|---|---|
| V—HBH—VFF | 3.0% |
| 3-DB—C | 10.0% |
| 4-DB—C | 10.0% |
| 2-BEB—C | 12.0% |
| 3-BEB—C | 4.0% |
| 3-PyB(F)—F | 6.0% |
| 3-HEB—O4 | 8.0% |
| 4-HEB—O2 | 6.0% |
| 5-HEB—O1 | 6.0% |
| 3-HEB—O2 | 5.0% |
| 5-HEB—O2 | 4.0% |
| 5-HEB-5 | 5.0% |
| 4-HEB-5 | 5.0% |
| 1O—BEB-2 | 4.0% |
| 3-HHB-1 | 3.0% |
| 3-HHEBB—C | 3.0% |
| 3-HBEBB—C | 3.0% |
| 5-HBEBB—C | 3.0% |
| $T_{NI}$ = 68.4 (° C.) | |
| $\eta$ = 39.5 (mPa · s) | |
| $\Delta n$ = 0.121 | |
| $\Delta_\epsilon$ = 11.5 | |
| Vth = 1.30 (V) | |

Example 13

TABLE 39

| | |
|---|---|
| 3-HVH—2VFF | 4.0% |
| V2-HBBH—VFF | 2.0% |
| 3-HB—C | 18.0% |
| 7-HB—C | 3.0% |
| 1O1-HB—C | 10.0% |
| 3-HB(F)—C | 10.0% |
| 2-PyB-2 | 2.0% |
| 3-PyB-2 | 2.0% |
| 4-PyB-2 | 2.0% |
| 1O1-HH-3 | 3.0% |
| 2-BTB—O1 | 7.0% |
| 3-HHB-1 | 7.0% |
| 3-HHB—F | 4.0% |
| 3-HHB—O1 | 4.0% |
| 3-HHB-3 | 6.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |
| $T_{NI}$ = 81.9 (° C.) | |
| $\eta$ = 18.1 (mPa · s) | |
| $\Delta n$ = 0.143 | |
| $\Delta_\epsilon$ = 8.2 | |
| Vth = 1.74 (V) | |

Example 14

TABLE 40

| | |
|---|---|
| 3-BHVH—VFF | 3.0% |
| 5-HVHH—VFF | 3.0% |
| V—HV(Me)H—VFF | 4.0% |
| 2O1-BEB(F)—C | 5.0% |

TABLE 40-continued

| | |
|---|---|
| 3O1-BEB(F)—C | 12.0% |
| 5O1-BEB(F)—C | 4.0% |
| 1V2-BEB(F,F)—C | 10.0% |
| 3-HH—EMe | 10.0% |
| 3-HB—O2 | 14.0% |
| 7-HEB—F | 2.0% |
| 3-HHEB—F | 2.0% |
| 5-HHEB—F | 2.0% |
| 3-HBEB—F | 4.0% |
| 2O1-HBEB(F)—C | 2.0% |
| 3-HB(F)EB(F)—C | 2.0% |
| 3-HBEB(F,F)—C | 2.0% |
| 3-HHB—F | 4.0% |
| 3-HHB—O1 | 4.0% |
| 3-HHB-3 | 7.0% |
| 3-HEBEB—F | 2.0% |
| 3-HEBEB-1 | 2.0% |

$T_{NI} = 76.8$ (° C.)
$\eta = 35.7$ (mPa·s)
$\Delta n = 0.114$
$\Delta_\epsilon = 23.4$
Vth = 0.99 (V)

Example 15

TABLE 41

| | |
|---|---|
| 3-BFVFB—VFF | 4.0% |
| 5-BEB(F)—C | 5.0% |
| V-HB—C | 11.0% |
| 5-PyB—C | 6.0% |
| 4-BB-3 | 7.0% |
| 3-HH—2V | 10.0% |
| 5-HH—V | 11.0% |
| V-HHB-1 | 7.0% |
| V2-HHB-1 | 15.0% |
| 3-HHB-1 | 9.0% |
| 1V2-HBB-2 | 10.0% |
| 3-HHEBH-3 | 5.0% |

$T_{NI} = 95.2$ (° C.)
$\eta = 15.7$ (mPa·s)
$\Delta n = 0.123$
$\Delta_\epsilon = 4.8$
Vth = 2.36 (V)

Example 16

TABLE 42

| | |
|---|---|
| 3-BCF2OBH—2VFF | 2.0% |
| 3-BD2H—VFF | 3.0% |
| 2O1-BEB(F)—C | 5.0% |
| 3O1-BEB(F)—C | 12.0% |
| 5O1-BEB(F)—C | 4.0% |
| 1V2-BEB(F,F)—C | 16.0% |
| 3-HB—O2 | 10.0% |
| 3-HH-4 | 3.0% |
| 3-HHB—F | 3.0% |
| 3-HHB-1 | 8.0% |
| 3-HHB—O1 | 4.0% |
| 3-HBEB—F | 2.0% |
| 3-HHEB—F | 4.0% |
| 5-HHEB—F | 7.0% |
| 3-H2BTB-2 | 4.0% |
| 3-H2BTB-3 | 4.0% |
| 3-H2BTB-4 | 4.0% |
| 3-HB(F)TB-2 | 5.0% |

$T_{NI} = 89.2$ (° C.)
$\eta = 40.2$ (mpa·s)
$\Delta n = 0.143$
$\Delta_\epsilon = 28.0$
Vth = 1.01 (V)

Example 17

TABLE 43

| | |
|---|---|
| 3-HVH—VF | 5.0% |
| 2-BEB—C | 12.0% |
| 3-BEB—C | 4.0% |
| 4-BEB—C | 6.0% |
| 3-HB—C | 28.0% |
| 3-HEB—O4 | 7.0% |
| 4-HEB—O2 | 8.0% |
| 5-HEB—O1 | 8.0% |
| 3-HEB—O2 | 6.0% |
| 5-HEB—O2 | 5.0% |
| 3-HHB-1 | 7.0% |
| 3-HHB—O1 | 4.0% |

$T_{NI} = 63.5$ (° C.)
$\eta = 24.2$ (mPa·s)
$\Delta n = 0.112$
$\Delta_\epsilon = 10.0$
Vth = 1.35 (V)

Example 18

TABLE 44

| | |
|---|---|
| 3-BB(F)BH—VFF | 3.0% |
| 2-BEB—C | 10.0% |
| 5-BB—C | 12.0% |
| 7-BB—C | 7.0% |
| 1-BTB-3 | 7.0% |
| 2-BTB-1 | 10.0% |
| 1O—BEB-2 | 10.0% |
| 1O—BEB-5 | 12.0% |
| 2-HHB-1 | 4.0% |
| 3-HHB—F | 4.0% |
| 3-HHB-1 | 7.0% |
| 3-HHB—O1 | 4.0% |
| 3-HHB-3 | 10.0% |

$T_{NI} = 69.3$ (° C.)
$\eta = 20.9$ (mPa·s)
$\Delta n = 0.164$
$\Delta_\epsilon = 6.5$
Vth = 1.78 (V)

Example 19

TABLE 45

| | |
|---|---|
| 3-B(F)B(F)2H—2VFF | 4.0% |
| V2-HBBH—VFF | 3.0% |
| 1V2-BEB(F,F)—C | 8.0% |
| 3-HB—C | 10.0% |
| V2V—HB—C | 14.0% |
| V2V—HH-3 | 19.0% |
| 3-HB—O2 | 4.0% |
| 3-HHB-1 | 10.0% |
| 3-HHB-3 | 12.0% |
| 3-HB(F)TB-2 | 2.0% |
| 3-HB(F)TB-3 | 4.0% |
| 3-H2BTB-2 | 2.0% |
| 3-H2BTB-3 | 4.0% |
| 3-H2BTB-4 | 4.0% |

$T_{NI} = 98.5$ (° C.)
$\eta = 18.5$ (mPa·s)
$\Delta n = 0.124$
$\Delta_\epsilon = 7.7$
Vth = 2.13 (V)

Example 20

TABLE 46

| | |
|---|---|
| 5-HB(2F,3F)H—VFF | 5.0% |
| 5-BTB(F)TB-3 | 10.0% |
| V2-HB—TC | 10.0% |
| 3-HB—TC | 10.0% |
| 3-HB—C | 10.0% |
| 5-HB—C | 7.0% |
| 5-BB—C | 3.0% |
| 2-BTB-1 | 10.0% |
| 2-BTB—O1 | 5.0% |
| 3-HH-4 | 5.0% |
| 3-HHB-1 | 10.0% |
| 3-HHB-3 | 6.0% |
| 3-H2BTB-2 | 3.0% |
| 3-H2BTB-3 | 3.0% |
| 3-HB(F)TB-2 | 3.0% |
| $T_{NI}$ = 97.3 (° C.) | |
| $\eta$ = 14.9 (mPa · s) | |
| $\Delta n$ = 0.205 | |
| $\Delta_\epsilon$ = 6.7 | |
| Vth = 2.12 (V) | |

Example 21

TABLE 47

| | |
|---|---|
| 5-HB(2F,3F)H—VFF | 5.0% |
| 5-HBBH—VFF | 4.0% |
| 1V2-BEB(F,F)—C | 6.0% |
| 3-HB—C | 18.0% |
| 2-BTB-1 | 10.0% |
| 5-HH—VFF | 25.0% |
| 1-BHH—VFF | 4.0% |
| 1-BHH—2VFF | 11.0% |
| 3-H2BTB-2 | 5.0% |
| 3-H2BTB-3 | 4.0% |
| 3-H2BTB-4 | 4.0% |
| 3-HHB-1 | 4.0% |
| $T_{NI}$ = 86.3 (° C.) | |
| $\eta$ = 14.3 (mPa · s) | |
| $\Delta n$ = 0.136 | |
| $\Delta_\epsilon$ = 6.6 | |
| Vth = 2.05 (V) | |

Example 22

TABLE 48

| | |
|---|---|
| 5-HB(2F,3F)H—VFF | 4.0% |
| 3-HVH—VF | 4.0% |
| 2-HB—C | 5.0% |
| 3-HB—C | 12.0% |
| 3-HB—O2 | 11.0% |
| 2-BTB-1 | 3.0% |
| 3-HHB-1 | 8.0% |
| 3-HHB—F | 4.0% |
| 3-HHB—O1 | 5.0% |
| 3-HHB-3 | 10.0% |
| 3-HHEB—F | 4.0% |
| 5-HHEB—F | 4.0% |
| 2-HHB(F)—F | 7.0% |
| 3-HHB(F)—F | 7.0% |
| 5-HHB(F)—F | 7.0% |
| 3-HHB(F,F)—F | 5.0% |
| $T_{NI}$ = 99.8 (° C.) | |
| $\eta$ = 18.7 (mPa · s) | |
| $\Delta n$ = 0.101 | |
| $\Delta_\epsilon$ = 4.4 | |
| Vth = 2.60 (V) | |

Example 23

TABLE 49

| | |
|---|---|
| 5-HB(2F,3F)H—VFF | 5.0% |
| 2-HHB(F)—F | 15.0% |
| 3-HHB(F)—F | 15.0% |
| 5-HHB(F)—F | 15.0% |
| 2-H2HB(F)—F | 10.0% |
| 3-H2HB(F)—F | 5.0% |
| 5-H2HB(F)—F | 10.0% |
| 2-HBB(F)—F | 6.0% |
| 3-HBB(F)—F | 6.0% |
| 5-HBB(F)—F | 13.0% |
| CN | 0.3 part |
| $T_{NI}$ = 97.4 (° C.) | |
| $\eta$ = 26.1 (mPa · s) | |
| $\Delta n$ = 0.095 | |
| $\Delta_\epsilon$ = 5.0 | |
| Vth = 2.22 (V) | |
| P = 79 $\mu$m | |

Example 24

TABLE 50

| | |
|---|---|
| 3-BH2H—VFF | 4.0% |
| 7-HB(F)—F | 5.0% |
| 5-H2B(F)—F | 5.0% |
| 3-HB—O2 | 10.0% |
| 3-HH-4 | 2.0% |
| 3-HH[5D,6D,7D]-4 | 3.0% |
| 2-HHB(F)—F | 10.0% |
| 3-HHB(F)—F | 10.0% |
| 5-HH[5D,6D,7D]B(F)—F | 10.0% |
| 3-H2HB(F)—F | 5.0% |
| 2-HBB(F)—F | 3.0% |
| 3-HBB(F)—F | 3.0% |
| 5-HBB(F)—F | 6.0% |
| 2-H2BB(F)—F | 5.0% |
| 3-H2BB(F)—F | 6.0% |
| 3-HHB-1 | 4.0% |
| 3-HHB—O1 | 5.0% |
| 3-HHB-3 | 4.0% |
| $T_{NI}$ = 87.0 (° C.) | |
| $\eta$ = 18.7 (mPa · s) | |
| $\Delta n$ = 0.092 | |
| $\Delta_\epsilon$ = 3.3 | |
| Vth = 2.65 (V) | |

Example 25

TABLE 51

| | |
|---|---|
| 3-B(F)B(F)2H—2VFF | 4.0% |
| 7-HB(F,F)—F | 3.0% |
| 3-HB—O2 | 7.0% |
| 2-HHB(F)—F | 10.0% |
| 3-HHB(F)—F | 10.0% |
| 5-HHB(F)—F | 10.0% |
| 2-HBB(F)—F | 9.0% |
| 3-HBB(F)—F | 9.0% |
| 5-HBB(F)—F | 16.0% |
| 2-HBB—F | 2.0% |
| 3-HBB—F | 2.0% |
| 5-HBB—F | 3.0% |
| 3-HBB(F,F)—F | 5.0% |
| 5-HBB(F,F)—F | 10.0% |
| $T_{NI}$ = 84.2 (° C.) | |
| $\eta$ = 25.6 (mPa · s) | |
| $\Delta n$ = 0.113 | |
| $\Delta_\epsilon$ = 5.7 | |
| Vth = 2.01 (V) | |

Example 26

TABLE 52

| | |
|---|---|
| 3-BCF2OBH—2VFF | 3.0% |
| 3-BFVFB—VFF | 4.0% |
| 7-HB(F,F)—F | 3.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 5.0% |
| 4-HHB(F,F)—F | 5.0% |
| 3-HH2B(F,F)—F | 15.0% |
| 5-HH2B(F,F)—F | 10.0% |
| 3-HBB(F,F)—F | 12.0% |
| 5-HBB(F,F)—F | 5.0% |
| 3-HBCF2OB(F,F)—F | 6.0% |
| $T_{NI}$ = 74.8 (° C.) | |
| $\eta$ = 22.2 (mPa · s) | |
| $\Delta n$ = 0.093 | |
| $\Delta_\epsilon$ = 8.3 | |
| Vth = 1.58 (V) | |

Example 27

TABLE 53

| | |
|---|---|
| 3-BD2H—VFF | 5.0% |
| 3-BBHH—2VFF | 3.0% |
| 7-HB(F,F)—F | 5.0% |
| 3-H2HB(F,F)—F | 12.0% |
| 4-H2HB(F,F)—F | 10.0% |
| 3-HHB(F,F)—F | 10.0% |
| 4-HHB(F,F)—F | 5.0% |
| 3-HBB(F,F)—F | 10.0% |
| 3-HHEB(F,F)—F | 10.0% |
| 4-HHEB(F,F)—F | 3.0% |
| 5-HHEB(F,F)—F | 3.0% |
| 2-HBEB(F,F)—F | 3.0% |
| 3-HBEB(F,F)—F | 5.0% |
| 5-HBEB(F,F)—F | 3.0% |
| 3-HDB(F,F)—F | 10.0% |
| 3-HHBB(F,F)—F | 3.0% |
| $T_{NI}$ = 78.4 (° C.) | |
| $\eta$ = 36.2 (mPa · s) | |
| $\Delta n$ = 0.088 | |
| $\Delta_\epsilon$ = 12.5 | |
| Vth = 1.42 (V) | |

Example 28

TABLE 54

| | |
|---|---|
| 3-BB(F)BH—VFF | 4.0% |
| 3-HVH—2VFF | 3.0% |
| 3-HB—CL | 10.0% |
| 5-HB—CL | 4.0% |
| 7-HB—CL | 4.0% |
| 1O1-HH-5 | 2.0% |
| 2-HBB(F)—F | 8.0% |
| 3-HBB(F)—F | 8.0% |
| 5-HBB(F)—F | 14.0% |
| 4-HHB—CL | 8.0% |
| 5-HHB—CL | 8.0% |
| 3-H2HB(F)—CL | 4.0% |
| 3-HBB(F,F)—F | 10.0% |
| 5-H2BB(F,F)—F | 9.0% |
| 3-HB(F)VB-2 | 2.0% |
| 3-HB(F)VB-3 | 2.0% |
| $T_{NI}$ = 92.8 (° C.) | |
| $\eta$ = 20.9 (mPa · s) | |
| $\Delta n$ = 0.129 | |
| $\Delta_\epsilon$ = 4.9 | |
| Vth = 2.32 (V) | |

Example 29

TABLE 55

| | |
|---|---|
| 5-HBBH—VFF | 4.0% |
| 3-HHB(F,F)—F | 9.0% |
| 3-H2HB(F,F)—F | 8.0% |
| 4-H2HB(F,F)—F | 8.0% |
| 5-H2HB(F,F)—F | 8.0% |
| 3-HBB(F,F)—F | 21.0% |
| 5-HBB(F,F)—F | 20.0% |
| 3-H2BB(F,F)—F | 10.0% |
| 5-HHBB(F,F)—F | 3.0% |
| 5-HHEBB—F | 2.0% |
| 3-HH2BB(F,F)—F | 3.0% |
| 1O1-HBBH-4 | 2.0% |
| 1O1-HBBH-5 | 2.0% |
| $T_{NI}$ = 97.6 (° C.) | |
| $\eta$ = 33.7 (mPa · s) | |
| $\Delta n$ = 0.116 | |
| $\Delta_\epsilon$ = 9.2 | |
| Vth = 1.74 (V) | |

Example 30

TABLE 56

| | |
|---|---|
| 5-HBBH—VFF | 2.0% |
| 5-HVHH—VFF | 2.0% |
| V—HV(Me)H—VFF | 2.0% |
| 5-HB—F | 12.0% |
| 6-HB—F | 9.0% |
| 7-HB—F | 5.0% |
| 2-HHB—OCF3 | 5.0% |
| 3-HHB—OCF3 | 7.0% |
| 4-HHB—OCF3 | 7.0% |
| 5-HHB—OCF3 | 5.0% |
| 3-HH2B—OCF3 | 4.0% |
| 5-HH2B—OCF3 | 4.0% |
| 3-HHB(F,F)-OCF3 | 5.0% |
| 3-HBB(F)—F | 10.0% |
| 5-HBB(F)—F | 10.0% |
| 3-HH2B(F)—F | 3.0% |
| 3-HB(F)BH-3 | 2.0% |
| 5-HBBH-3 | 2.0% |
| 3-HHB(F,F)—OCF2H | 4.0% |
| $T_{NI}$ = 88.7 (° C.) | |
| $\eta$ = 15.2 (mPa · s) | |
| $\Delta n$ = 0.093 | |
| $\Delta_\epsilon$ = 4.5 | |
| Vth = 2.40 (V) | |

Example 31

TABLE 57

| | |
|---|---|
| V2-HBBH—VFF | 2.0% |
| V—HBH—VFF | 3.0% |
| 3-BHVH—VFF | 2.0% |
| 5-H4HB(F,F)—F | 7.0% |
| 5-H4HB—OCF3 | 10.0% |
| 3-H4HB(F,F)—CF3 | 8.0% |
| 5-H4HB(F,F)—CF3 | 10.0% |
| 3-HB—CL | 6.0% |
| 5-HB—CL | 4.0% |
| 2-H2BB(F)—F | 5.0% |
| 3-H2BB(F)—F | 10.0% |
| 5-HVHB(F,F)—F | 5.0% |
| 3-HHB—OCF3 | 3.0% |
| 3-H2HB—OCF3 | 5.0% |
| V—HHB(F)—F | 5.0% |
| 3-HHB(F)—F | 5.0% |
| 5-HHEB—OCF3 | 2.0% |
| 3-HBEB(F,F)—F | 5.0% |
| 5-HH—V2F | 3.0% |
| $T_{NI}$ = 3.8 (° C.) | |

Example 32

TABLE 58

| | |
|---|---|
| 5-HBBH—VFF | 4.0% |
| 5-HB(2F,3F)H—VFF | 2.0% |
| 2-HHB(F)—F | 2.0% |
| 3-HHB(F)—F | 2.0% |
| 5-HHB(F)—F | 2.0% |
| 2-HBB(F)—F | 6.0% |
| 3-HBB(F)—F | 6.0% |
| 5-HBB(F)—F | 10.0% |
| 2-H2BB(F)—F | 9.0% |
| 3-H2BB(F)—F | 9.0% |
| 3-HBB(F,F)—F | 25.0% |
| 5-HBB(F,F)—F | 19.0% |
| 1O1-HBBH-4 | 2.0% |
| 1O1-HBBH-5 | 2.0% |
| $T_{NI}$ = 92.0 (° C.) | |
| $\eta$ = 33.3 (mPa · s) | |
| $\Delta n$ = 0.136 | |
| $\Delta_\epsilon$ = 7.4 | |
| Vth = 1.90 (V) | |

Example 33

TABLE 59

| | |
|---|---|
| 3-HVH—VF | 3.0% |
| 3-BFVFB—VFF | 3.0% |
| 5-HB—CL | 12.0% |
| 3-HH-4 | 4.0% |
| 3-HB—O2 | 20.0% |
| 3-H2HB(F,F)—F | 8.0% |
| 3-HHB(F,F)—F | 8.0% |
| 3-HBB(F,F)—F | 6.0% |
| 2-HHB(F)—F | 5.0% |
| 3-HHB(F)—F | 5.0% |
| 5-HHB(F)—F | 5.0% |
| 2-H2HB(F)—F | 2.0% |
| 3-H2HB(F)—F | 1.0% |
| 5-H2HB(F)—F | 2.0% |
| 3-HHBB(F,F)—F | 4.0% |
| 3-HBCF2OB—OCF3 | 4.0% |
| 5-HBCF2OB(F,F)—CF3 | 4.0% |
| 3-HHB-1 | 2.0% |
| 3-HHB—O1 | 2.0% |
| $T_{NI}$ = 69.2 (° C.) | |
| $\eta$ = 13.9 (mPa · s) | |
| $\Delta n$ = 0.090 | |
| $\Delta_\epsilon$ = 4.1 | |
| Vth = 2.21 (V) | |

Example 34

TABLE 60

| | |
|---|---|
| 3-HVH—VF | 10.0% |
| 3-HVH—2VFF | 10.0% |
| 3-BHVH—VFF | 10.0% |
| 3-BH2H—VFF | 10.0% |
| V2-HBBH—VFF | 2.0% |
| 1V2-BEB(F,F)—C | 5.0% |
| 3-HB—C | 25.0% |
| 1-BTB-3 | 3.0% |
| 3-HH-4 | 2.0% |

TABLE 60-continued

| | |
|---|---|
| 3-HHB-1 | 3.0% |
| 3-H2BTB-2 | 2.0% |
| 3-H2BTB-3 | 2.0% |
| 3-H2BTB-4 | 4.0% |
| 3-HB(F)TB-2 | 6.0% |
| 3-HB(F)TB-3 | 6.0% |
| $T_{NI}$ = 91.9 (° C.) | |
| $\eta$ = 15.8 (mPa · s) | |
| $\Delta n$ = 0.138 | |
| $\Delta_\epsilon$ = 6.7 | |
| Vth = 2.16 (V) | |

What is claimed is:

1. A fluorovinyl derivative compound represent by the general formula (1)

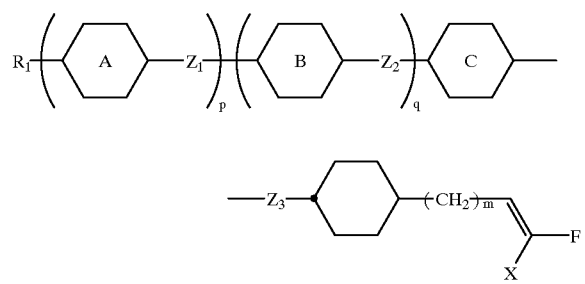

wherein $R_1$ is an alkyl group having 1 to 18 carbon atoms, and a methylene group in the alkyl group may be substituted by an oxygen atom, a sulfur atom, —CH=CH— or —C≡C— and a hydrogen atom in the alkyl group may be substituted by a halogen atom or a cyano group;

rings A, B and C are each independently 1,4-cyclohexylene, 1,4-cyclohexenylene, 1,4-phenylene, 1,3-dioxane-2,5-diyl, pyridine-2,5-diyl or pyrimidine-2,5-diyl in which a hydrogen atom in the ring may be substituted by a halogen atom;

$Z_1$, $Z_2$ and $Z_3$ are each independently a single bond, —CH$_2$CH$_2$—, —CH=CH—,-CH$_2$O—, —OCH$_2$—, —(CH$_2$)$_4$—, —(CH$_2$)$_3$—O—, —O—(CH$_2$)$_3$—, —(CH$_2$)$_2$—CH=CH—, —CH=CH—(CH$_2$)$_2$—, —CF$_2$O—, —OCF$_2$—, —CR$_2$=CH—, —CH=CR$_2$— or —CF=CF—, and $R_2$ is an alkyl group having 1 to 5 carbon atoms;

X is a hydrogen atom or a fluorine atom; p and q are each independently 0 or 1; and m is an integer of 0 to 5;

except for (1) a compound in which p is 0, q is 0, $Z_3$ is the single bond, —CH$_2$CH$_2$—, —CH$_2$O— or —OCH$_2$—, and the ring C is 1,4-cyclohexylene or 1,4-phenylene, (2) a compound in which p is 0, q is 1, $Z_2$ and $Z_3$ are each the single bond, the ring B is 1,4-phenylene, and the ring C is 1,4-cyclohexylene or 1,4-phenylene, and (3) a compound in which p is 0, is 1, $Z_2$ is a single bond, $Z_3$ is —CH$_2$CH$_2$—, the ring B is 1,4-phenylene, the ring C is 1,4-cyclohexylene, and X is a hydrogen atom.

2. The fluorovinyl derivative compound according to claim 1 wherein at least one of $Z_1$, $Z_2$ and $Z_3$ is —CH=CH—, —(CH$_2$)$_3$O—, —O—(CH$_2$)$_3$—, —(CH$_2$)$_2$—CH=CH—, —CH=CH—(CH$_2$)$_2$—, —CF$_2$O—, —OCF$_2$—, —CR$_2$=CH—, —CH=CR$_2$— or —CF=CF—; and R$_2$ is an alkyl group having 1 to 5 carbon atoms.

3. The fluorovinyl derivative compound according to claim 1 wherein at least one of Z$_1$, Z$_2$ and Z$_3$ is —CH=CH—, —(CH$_2$)$_2$—CH=CH—, —CH=CH—(CH$_2$)$_2$— or —CF=CF—.

4. The fluorovinyl derivative compound according to claim 1 wherein at least one of Z$_1$, Z$_2$ and Z$_3$ is —(CH$_2$)$_3$—O—, —O—(CH$_2$)$_3$—, —CF$_2$O— or —OCF$_2$—.

5. The fluorovinyl derivative compound according to claim 1 wherein at least one of Z$_1$, Z$_2$ and Z$_3$ is —CR$_2$=CH— or —CH=CR$_2$—; and R$_2$ is an alkyl group having 1 to 5 carbon atoms.

6. A fluorovinyl derivative compound represented by the general formula (1-1)

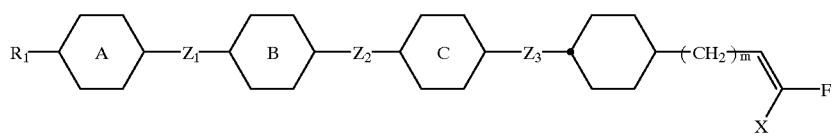

(1-1)

wherein R$_1$, X and m are as defined in claim 1; Z$_1$, Z$_2$ and Z$_3$ are each independently a single bond, —CH$_2$CH$_2$—, —CH$_2$O—, —OCH$_2$— or —(CH$_2$)$_4$—; and rings A, B and C are each independently 1,4-cyclohexylene or 1,4-phenylene in which a hydrogen atom in the ring may be substituted by a halogen atom.

7. A fluorovinyl derivative compound represented by the general formula (1-2)

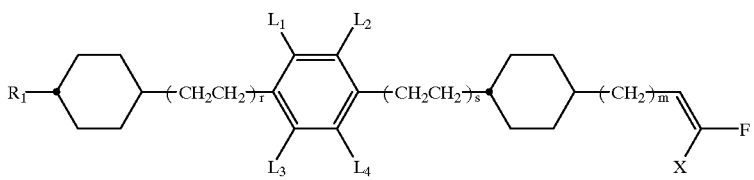

(1-2)

wherein R$_1$, X and m are as defined in claim 1; r and s are each independently 0 or 1; and L$_1$, L$_2$, L$_3$ and L$_4$ are each independently a hydrogen atom or a fluorine atom.

8. The fluorovinyl derivative compound according to claim 7 wherein r+s is 1 or 0.

9. The fluorovinyl derivative compound according to claim 7 wherein r+s is 2.

10. A fluorovinyl derivative compound represented by the general formula (1-3)

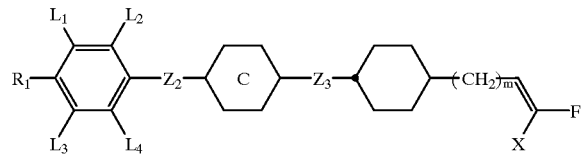

(1-3)

wherein R$_1$, X, m, L$_1$, L$_2$, L$_3$ and L$_4$ are as defined in claim 7; Z$_2$ and Z$_3$ are each independently a single bond, —CH$_2$CH$_2$—, —CH$_2$O—, —OCH$_2$— or —(CH$_2$)$_4$—, and Z$_2$ and Z$_3$ are not simultaneously the single bonds; and a ring C is 1,4-cyclohexylene or 1,4-phenylene in which a hydrogen atom in the ring may be substituted by a halogen atom.

11. The fluorovinyl derivative compound according to claim 10 wherein the ring C is 1,4-cyclohexylene.

12. The fluorovinyl derivative compound according to claim 10 wherein the ring C is 1,4-phenylene in which a hydrogen atom in the ring may be substituted by a halogen atom.

13. A fluorovinyl derivative compound represented by the general formula (1-1-1)

(1-1-1)

wherein R$_1$, X and m are as defined in claim 1; and L$_1$ to L$_8$ are each independently a hydrogen atom or a fluorine atom.

14. A fluorovinyl derivative compound represented by the general formula (1-1-2)

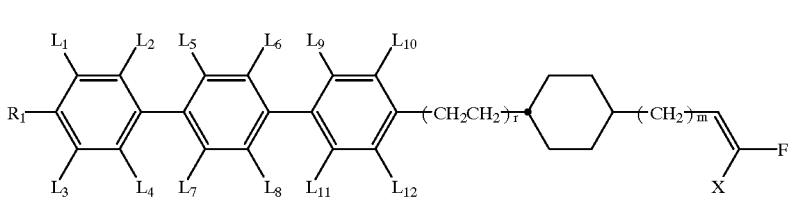

(1-1-2)

wherein $R_1$, X and m are as defined in claim 1; $L_1$ to $L_{12}$ are each independently a hydrogen atom or a fluorine atom; and r is 0 or 1.

15. A fluorovinyl derivative compound represented by the general formula (1-1-3)

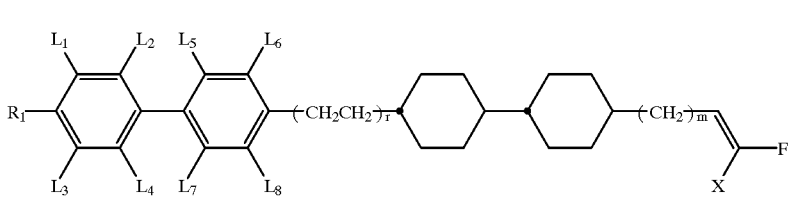

(1-1-3)

wherein $R_1$, X and m are as defined in claim 1; $L_1$ to $L_8$ are each independently a hydrogen atom or a fluorine atom; and r is 0 or 1.

16. A fluorovinyl derivative compound represented by the general formula (1-4-1)

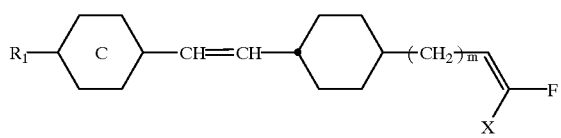

(1-4-1)

wherein $R_1$, X and m are as defined in claim 1; and the ring C is 1,4-cyclohexylene or 1,4-phenylene in which a hydrogen atom in the ring may be substituted by a halogen atom.

17. A fluorovinyl derivative compound represented by the general formula (1-4-2)

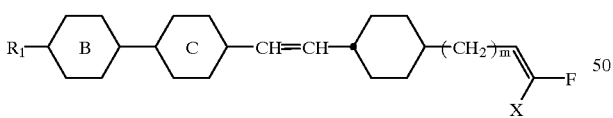

(1-4-2)

wherein $R_1$, X and m are as defined in claim 1; and the rings B and C are each 1,4-cyclohexylene or 1,4-phenylene in which a hydrogen atom in the ring may be substituted by a halogen atom.

18. A fluorovinyl derivative compound represented by the general formula (1-4-3)

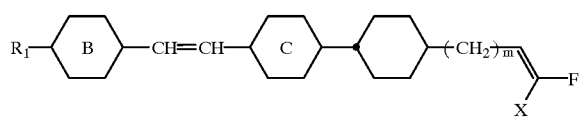

(1-4-3)

wherein $R_1$, X and m are as defined in claim 1; and the rings B and C are each 1,4-cyclohexylene or 1,4-phenylene in which a hydrogen atom in the ring may be substituted by a halogen atom.

19. A fluorovinyl derivative compound represented by the general formula (1-4-4)

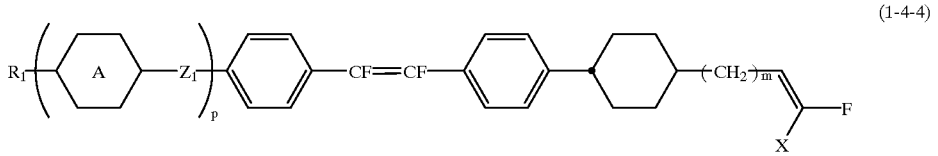

(1-4-4)

wherein $R_1$, X, m, Z, and p are as defined in claim 1; and the ring A is 1,4-cyclohexylene or 1,4-phenylene in which a hydrogen atom in the ring may be substituted by a halogen atom.

20. A fluorovinyl derivative compound represented by the general formula (1-4-5)

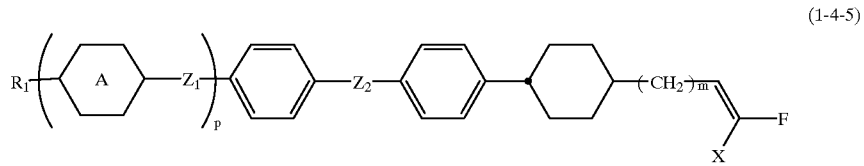

(1-4-5)

wherein $R_1$, X, m, $Z_1$ and p are as defined in claim 1; the ring A is 1,4-cyclohexylene or 1,4-phenylene in which a hydrogen atom in the ring may be substituted by a halogen atom; and $Z_2$ is —$CF_2O$— or —$OCF_2$—.

21. A fluorovinyl derivative compound represented by the general formula (1-4-6)

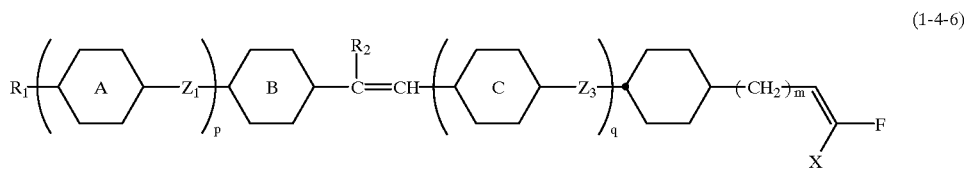

(1-4-6)

wherein $R_1$, X, m, $Z_1$, $Z_3$, p and q are as defined in claim 1; the rings A, B and C are each 1,4-cyclohexylene or 1,4-phenylene in which a hydrogen atom in the ring may be substituted by a halogen atom; and $R_2$ is an alkyl group having 1 to 5 carbon atoms.

22. A fluorovinyl derivative compound represented by the general formula (1-4-7)

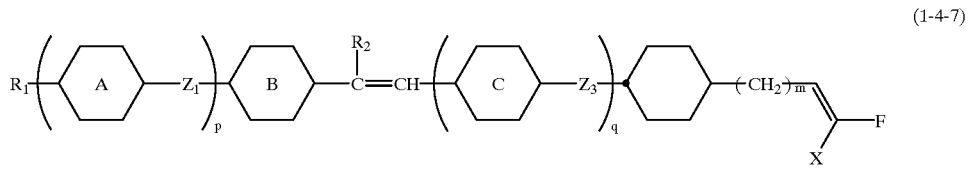

(1-4-7)

wherein $R_1$, X, m, $Z_1$, $Z_3$, p and q are as defined in claim 1; the rings A, B and C are each 1,4-cyclohexylene or 1,4-phenylene in which a hydrogen atom in the ring may be substituted by a halogen atom; and $R_2$ is an alkyl group having 1 to 5 carbon atoms.

23. A liquid crystal composition which contains at least one of the liquid crystal compounds described in claim 1.

24. A liquid crystal composition which contains, as a first component, at least one of the liquid crystal compounds described in claim 1, and as a second component, at least one compound selected from the group consisting of compounds of the general formulae (2), (3) and (4)

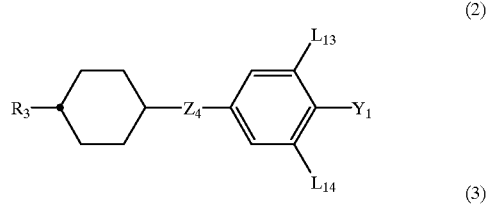

(2)

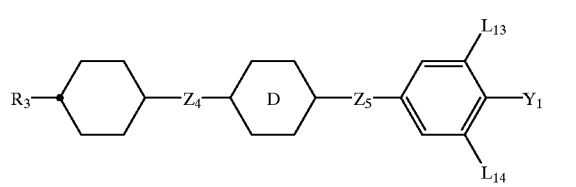

(3)

-continued (4)

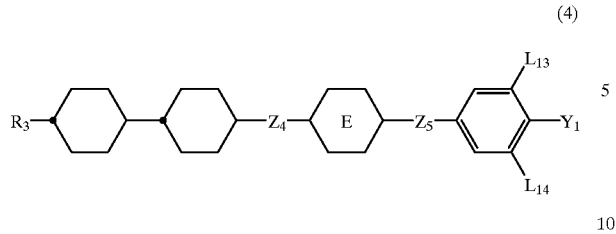

wherein $R_3$ is an alkyl group having 1 to 10 carbon atoms, and an optional unadjacent methylene group in the alkyl group may be substituted by an oxygen atom or —CH═CH—, and an optional hydrogen atom in the alkyl group may be substituted by a fluorine atom; $Y_1$ is a fluorine atom, a chlorine atom, $OCF_3$, $OCF_2H$, $CF_3$, $CF_2H$, $CFH_2$, $OCF_2CF_2H$ or $OCF_2CFHCF_3$; $L_{13}$ and $L_{14}$ are each independently a hydrogen atom or a fluorine atom; $Z_4$ and $Z_5$ are each independently a 1,2-ethylene group, a 1,4-butylene group, —COO—, —CF$_2$O—, —OCF$_2$—, —CH═CH— or a single bond; a ring D is trans-1,4-cyclohexylene, 1,3-dioxane-2,5-diyl or 1,4-phenylene in which a hydrogen atom may be substituted by a halogen atom; and a ring E is trans-1,4-cyclohexylene or 1,4-phenylene in which a hydrogen atom may be substituted by a fluorine atom.

25. A liquid crystal composition which contains, as a first component, at least one of the liquid crystal compounds described in claim 1, and as a second component, at least one compound selected from the group consisting of compounds of the general formulae (5) and (6)

(5)

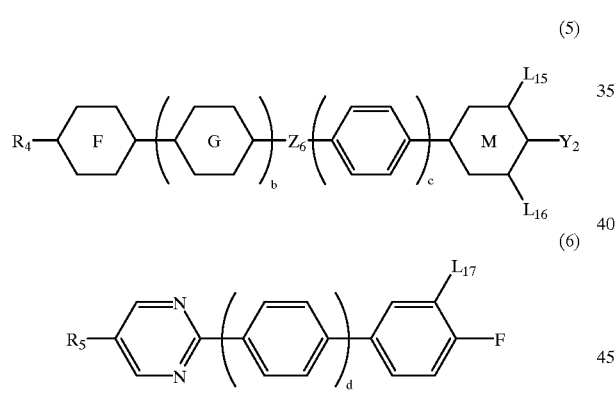

(6)

wherein $R_4$ and $R_5$ are each independently an alkyl group having 1 to 10 carbon atoms, and an optional unadjacent methylene group in the alkyl group may be substituted by an oxygen atom or —CH═CH—, and an optional hydrogen atom in the alkyl group may be substituted by a fluorine atom; $Y_2$ is a —CN group or —C≡C—CN; a ring F is trans-1,4-cyclohexylene, 1,4-phenylene, 1,3-dioxane-2,5-diyl or pyrimidine-2,5-diyl; a ring G is trans-1,4-cyclohexylene, 1,4-phenylene or pyrimidine-2,5-diyl in which a hydrogen atom may be substituted by a fluorine atom; a ring M is trans-1,4-cyclohexylene or 1,4-phenylene; $Z_6$ is a 1,2-ethylene group, —COO— or a single bond; $L_{15}$, $L_{16}$ and $L_{17}$ are each independently a hydrogen atom or a fluorine atom; and b, c and d are each independently 0 or 1.

26. A liquid crystal composition which contains at least one of the liquid crystal compounds described in claim 1 as a first component, at least one compound selected from the group consisting of compounds of the following general formulae (2), (3) and (4) as a second component (2)

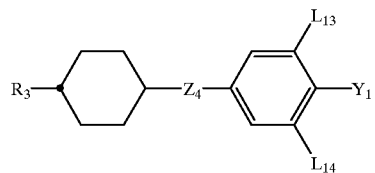

(3)

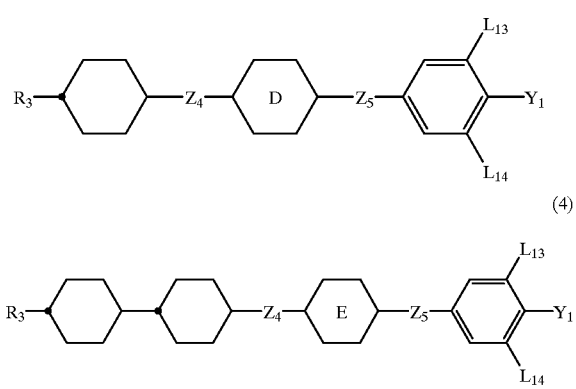

(4)

wherein $R_3$ is an alkyl group having 1 to 10 carbon atoms, and an optional unadjacent methylene group in the alkyl group may be substituted by an oxygen atom or —CH═CH—, and an optional hydrogen atom in the alkyl group may be substituted by a fluorine atom; $Y_1$ is a fluorine atom, a chlorine atom, $OCF_3$, $OCF_2H$, $CF_3$, $CF_2H$, $CFH_2$, $OCF_2CF_2H$ or $OCF_2CFHCF_3$; $L_{13}$ and $L_{14}$ are each independently a hydrogen atom or a fluorine atom; $Z_4$ and $Z_5$ are each independently a 1,2-ethylene group, a 1,4-butylene group, —COO—, —CF$_2$O—, —OCF$_2$—, —CH═CH— or a single bond; a ring D is trans-1,4-cyclohexylene, 1,3-dioxane-2,5-diyl or 1,4-phenylene in which a hydrogen atom may be substituted by a halogen atom; and a ring E is trans-1,4-cyclohexylene or 1,4-phenylene in which a hydrogen atom may be substituted by a fluorine atom; and at least one compound selected from the group consisting of compounds of the following general formulae (7), (8) and (9) as a third component (7)

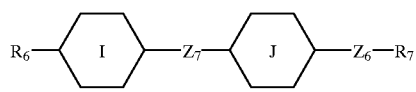

(8)

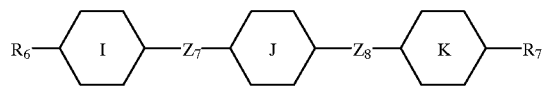

(9)

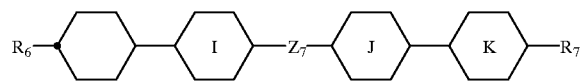

wherein $R_6$ and $R_7$ is each independently an alkyl group having 1 to 10 carbon atoms, and an optional unadjacent methylene group in the alkyl group may be substituted by an oxygen atom or —CH═CH—, and an optional hydrogen atom in the alkyl group may be substituted by a fluorine atom; rings I, J and 1< are each independently trans-1,4-cyclohexylene, pyrimidine-2,5-diyl or 1,4-phenylene in which a hydrogen atom may be substituted by a fluorine atom; $Z_7$ and $Z_8$ are each independently —C≡C—, —COO—, —CH$_2$Cl—1$_2$—, —CH=CH— or a single bond.

27. A liquid crystal composition which contains at least one of the liquid crystal compounds described in claim 1 as a first component, at least one compound selected from the group consisting of compounds of the following general formulae (5) and (6) as a second component (5)

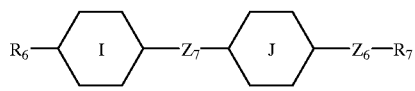

(6)

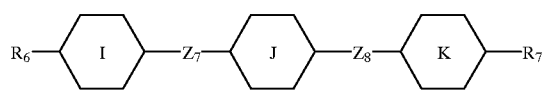

wherein $R_4$ and $R_5$ are each independently an alkyl group having 1 to 10 carbon atoms, and an optional unadjacent methylene group in the alkyl group may be substituted by an oxygen atom or —CH=CH—, and an optional hydrogen atom in the alkyl group may be substituted by a fluorine atom; $Y_2$ is a —CN group or —C≡C—CN; a ring F is trans-1,4-cyclohexylene, 1,4-phenylene, 1,3-dioxane-2,5-diyl or pyrimidine-2,5-diyl; a ring G is trans-1,4-cyclohexylene, 1,4-phenylene or pyrimidine-2,5-diyl in which a hydrogen atom may be substituted by a fluorine atom; a ring M is trans-1,4-cyclohexylene or 1,4-phenylene; $Z_6$ is a 1,2-ethylene group, —COO— or a single bond; $L_{15}$, $L_{16}$ and $L_{17}$ are each independently a hydrogen atom or a fluorine atom; and b, c and d are each independently 0 or 1; and at least one compound selected from the group consisting of compounds of the following general formulae (7), (8) and (9) as a third component (7)

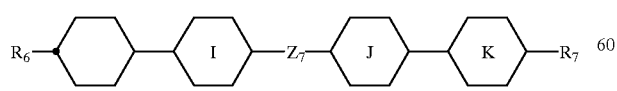

(8)

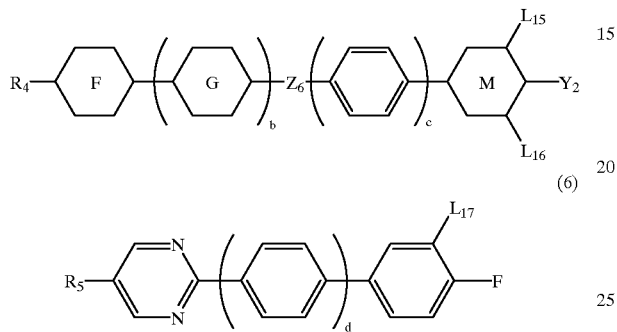

(9)

wherein $R_6$ and $R_7$ is each independently an alkyl group having 1 to 10 carbon atoms, and an optional unadjacent methylene group in the alkyl group may be substituted by an oxygen atom or —CH=CH—, and an optional hydrogen atom in the alkyl group may be substituted by a fluorine atom; rings, J and 1< are each independently trans-1,4-cyclohexylene, pyrimidine-2,5-diyl or 1,4-phenylene in which a hydrogen atom may be substituted by a fluorine atom; $Z_7$ and $Z_8$ are each independently —C≡C—, —COO—, —CH$_2$Cl—1$_2$—, —CH=CH— or a single bond.

28. A liquid crystal composition which contains at least one of the liquid crystal compounds described in claim 1 as a first component, at least one compound selected from the group consisting of compounds of the following general formulae (2), (3) and (4) as a second component (2)

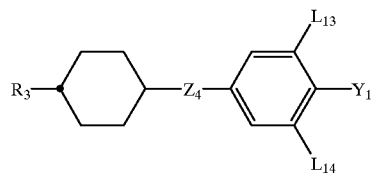

(3)

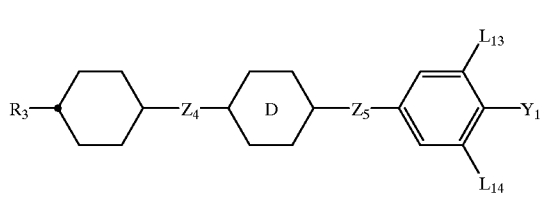

(4)

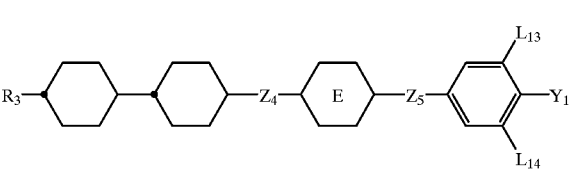

wherein $R_3$ is an alkyl group having 1 to 10 carbon atoms, and an optional unadjacent methylene group in the alkyl group may be substituted by an oxygen atom or —CH=CH—, and an optional hydrogen atom in the alkyl group may be substituted by a fluorine atom; $Y_1$ is a fluorine atom, a chlorine atom, OCF$_3$, OCF$_2$H, CF$_3$, CF$_2$H, CFH$_2$, OCF$_2$CF$_2$H or OCF$_2$CFHCF$_3$; $L_{13}$ and $L_{14}$ are each independently a hydrogen atom or a fluorine atom; $Z_4$ and $Z_5$ are each independently a 1,2-ethylene group, a 1,4-butylene group, —COO—, —CF$_2$O—, —OCF$_2$—, —CH=CH— or a single bond; a ring D is trans-1,4-cyclohexylene, 1,3-dioxane-2,5-diyl or 1,4-phenylene in which a hydrogen atom may be substituted by a halogen atom; and a ring E is trans-1,4-cyclohexylene or 1,4-phenylene in which a hydrogen atom may be substituted by a fluorine atom;

at least one compound selected from the group consisting of compounds of the following general formulae (5) and (6) as a third component (5)

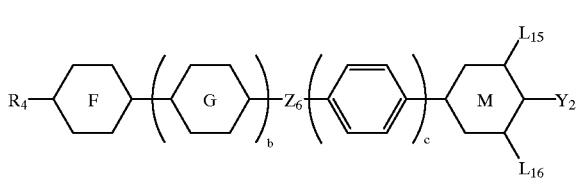

(6)

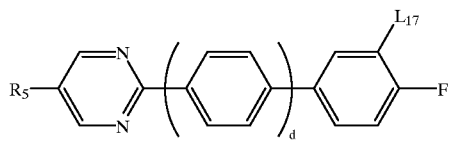

wherein $R_4$ and $R_5$ are each independently an alkyl group having 1 to 10 carbon atoms, and an optional unadjacent methylene group in the alkyl group may be substituted by an oxygen atom or —CH=CH—, and an optional hydrogen atom in the alkyl group may be substituted by a fluorine atom; $Y_2$ is a —CN group or —C=C—CN; a ring F is trans-1,4-cyclohexylene, 1,4-phenylene, 1,3-dioxane-2,5-diyl or pyrimidine-2,5-diyl; a ring G is trans-1,4-cyclohexylene, 1,4-phenylene or pyrimidine-2,5-diyl in which a hydrogen atom may be substituted by a fluorine atom; a ring M is trans-1,4-cyclohexylene or 1,4-phenylene; $Z_6$ is a 1,2-ethylene group, —COO— or a single bond; $L_{15}$, $L_{16}$ and $L_{17}$ are each independently a hydrogen atom or a fluorine atom; and b, c and d are each independently 0 or 1; and at least one compound selected from the group consisting of compounds of the general formulae (7), (8) and (9) as a fourth component (7)

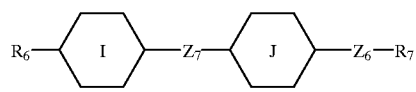

(8)

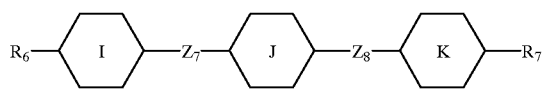

(9)

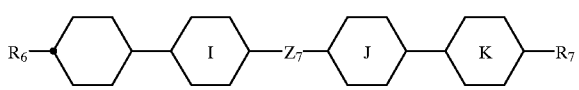

wherein $R_6$ and $R_7$ is each independently an alkyl group having 1 to 10 carbon atoms, and an optional unadjacent methylene group in the alkyl group may be substituted by an oxygen atom or —CH=CH—, and an optional hydrogen atom in the alkyl group may be substituted by a fluorine atom; rings, J and 1< are each independently trans-1,4-cyclohexylene, pyrimidine-2,5-diyl or 1,4-phenylene in which a hydrogen atom may be substituted by a fluorine atom; $Z_7$ and $Z_8$ are each independently —C≡C—, —COO—, —CH$_2$Cl—1$_2$—, —CH=CH— or a single bond.

29. A liquid crystal composition which comprises at least one fluorovinyl derivative compound represent by the general formula (1)

(1)

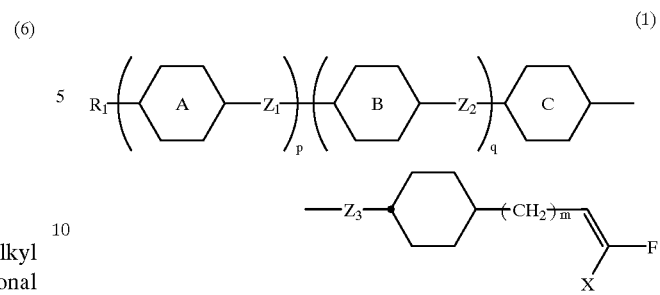

wherein $R_1$ is an alkyl group having 1 to 18 carbon atoms, and a methylene group in the alkyl group may be substituted by an oxygen atom, a sulfur atom, —CH=CH— or —C≡C— and a hydrogen atom in the alkyl group may be substituted by a halogen atom or a cyano group;

rings A, B and C are each independently 1,4-cyclohexylene, 1,4-cyclohexenylene, 1,4-phenylene, 1,3-dioxane-2,5-diyl, pyridine-2,5-diyl or pyrimidine-2,5-diyl in which a hydrogen atom in the ring may be substituted by a halogen atom;

$Z_1$, $Z_2$ and $Z_3$ are each independently a single bond, —CH$_2$CH$_2$—, —CH=CH—, -CH$_2$O—, —OCH$_2$—, —(CH$_2$)$_4$—, —(CH$_2$)$_3$—O—, —O—(CH$_2$)$_3$—, —(CH$_2$)$_2$—CH=CH—, —CH=CH—(CH$_2$)$_2$—, $_{CF_2}$O—, OCF$_2$—, —CR$_2$=CH—, —CH=CR$_2$— or —CF=CF—, and $R_2$ is an alkyl group having 1 to 5 carbon atoms;

X is a hydrogen atom or a fluorine atom; p and q are each independently 0 or 1; and m is an integer of O to 5;

except for (1) a compound in which p is 0, q is 0, $Z_3$ is the single bond, —CH$_2$CH$_2$—, —CH$_2$O— or —OCH$_2$—, and the ring C is 1,4-cyclohexylene or 1,4-phenylene, (2) a compound in which p is 0, q is 1, $Z_2$ and $Z_3$ are each the single bond, the ring B is 1,4-phenylene, and the ring C is 1,4-cyclohexylene or 1,4-phenylene, and (3) a compound in which p is 0, q is 1, $Z_2$ is a single bond, $Z_3$ is —CH$_2$CH$_2$—, the ring B is 1,4-phenylene, the ring C is 1,4-cyclohexylene, and X is a hydrogen atom; and at least one optically active compound.

30. A liquid crystal display device which comprises a liquid crystal composition which comprises at least one fluorovinyl derivative compound repreby the general formula (1)

(1)

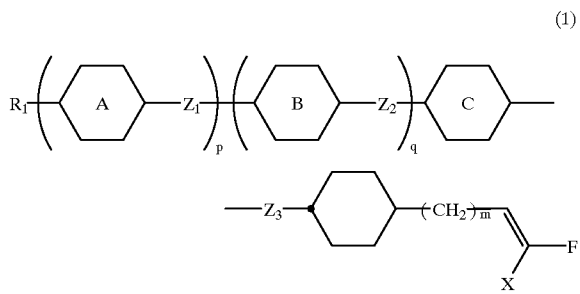

wherein $R_1$ is an alkyl group having 1 to 18 carbon atoms, and a methylene group in the alkyl group may be substituted by an oxygen atom, a sulfur atom, —CH=CH— or —C≡C— and a hydrogen atom in the alkyl group may be substituted by a halogen atom or a cyano group;

rings A, B and C are each independently 1,4-cyclohexylene, 1,4-cyclohexenylene, 1,4-phenylene, 1,3-dioxane-2,5-diyl, pyridine-2,5-diyl or pyrimidine-2,5-diyl in which a hydrogen atom in the ring may be substituted by a halogen atom;

$Z_1$, $Z_2$ and $Z_3$ are each independently a single bond, —CH$_2$CH$_2$—, —CH=CH—, —CH$_2$O—, —OCH$_2$—, —(CH$_2$)$_4$—, —(CH$_2$)$_3$—O—, —O—(CH$_2$)$_3$—, —(CH$_2$)$_2$—CH=CH—, —CH=CH—(CH$_2$)$_2$—, CF$_2$O—, —OCF$_2$—, —CR$_2$=CH—, —CH=CR$_2$— or —CF=CF—, and $R_2$ is an alkyl group having 1 to 5 carbon atoms;

X is a hydrogen atom or a fluorine atom; p and q are each independently 0 or 1; and m is an integer of 0 to 5;

except for (1) a compound in which p is 0, q is 0, $Z_3$ is the single bond, —CH$_2$CH$_2$—, —CH$_2$O— or —OCH$_2$—, and the ring C is 1,4-cyclohexylene or 1,4-phenylene, (2) a compound in which p is 0, q is 1, $Z_2$ and $Z_3$ are each the single bond, the ring B is 1,4-phenylene, and the ring C is 1,4-cyclohexylene or 1,4-phenylene, and (3) a compound in which p is 0, q is 1, $Z_2$ is a single bond, $Z_3$ is —CH$_2$CH$_2$—, the ring B is 1,4-phenylene, the ring C is 1,4-cyclohexylene, and X is a hydrogen atom; and at least one optically active compound.

\* \* \* \* \*

UNITED STATES PATENT AND TRADEMARK OFFICE
CERTIFICATE OF CORRECTION

PATENT NO. : 6,207,076 B1 Page 1 of 2
DATED : March 27, 2001
INVENTOR(S) : Kouji Koga et al.

It is certified that error appears in the above-identified patent and that said Letters Patent is hereby corrected as shown below:

Column 16,
Line 10, change "wherein $R_{11}$ m and $L_1$ to L5" to -- wherein $R_1$, m and $L_1$ to $L_8$ --;
Line 25, change "4-cyclohexylene" to -- 1,4-cyclohexylene --;

Column 25,
Line 44, change "wherein $R_{11}$ $R_{21}$ m and" to -- wherein $R_1$, $R_2$, m and --;

Column 88,
Line 25, change "at SoC or less" to -- at 5°C or less --;

Column 99,
Line 58, change "$C_2H_5$ 2 F" to -- $C_2H_5$ 2 H --;

Column 100,
Line 8, change "$C_2H_5$ 2 H" to -- $C_2H_5$ 2 F --;

Column 105,
Line 63, change "$OCF_2O$" to -- $OCF_2$ --;

Column 106,
Lines 8, 12, 17, 21, 25, 29, 34 and 40, change "$OCF_2O$" to -- $OCF_2$ --;

Column 107,
Line 20, change "$CH_3$ 0 F" to -- $CH_3$ 0 H --;

Column 108,
Line 20, change " 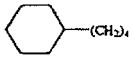 " to --  --
Line 55, change " 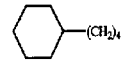 " to --  --

Column 109,
Line 5, change " 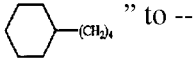 " to --  --

Column 132,
Line 66, change "$T_{NI}$ = 3.8(°C.)" to -- $T_{NI}$ = 73.8(°C.) --;

Column 134,
Line 60, change "p is 0, is 1, $Z_2$ is" to -- p is 0 q is 1, $Z_2$ is --;

Column 139,
Line 1, change "X, m, Z, and p" to -- X, m, $Z_1$ and p --;

UNITED STATES PATENT AND TRADEMARK OFFICE
CERTIFICATE OF CORRECTION

PATENT NO. : 6,207,076 B1
DATED : March 27, 2001
INVENTOR(S) : Kouji Koga et al.

It is certified that error appears in the above-identified patent and that said Letters Patent is hereby corrected as shown below:

Column 142,
Line 49, change "—$Z_6$—$Z_7$" to -- —$Z_8$—$R_7$ --;

Column 143,
Line 1, change "I, J and 1< are" to -- I, J and K are --;
Line 5, change "-$CH_2Cl$-$1_z$-" to -- -$CH_2CH_2$- --;
Line 50, change "—$Z_6$—$Z_7$" to -- —$Z_8$—$R_7$ --;

Column 144,
Line 2, change "rings, J and 1< are" to -- rings, J and K are --;
Line 6, change "-$CH_2Cl$-$1_2$-" to -- $CH_2CH_2$- --;

Column 145,
Line 36, change "—$Z_6$—$Z_7$" to -- —$Z_8$—$R_7$ --;
Line 57, change "rings, J and 1< are" to -- rings, J and K are --;
Line 61, change "-$CH_2Cl$-$1_z$-" to -- $CH_2CH_2$- --;
Line 64, change "represent by" to -- represented by --;

Column 146,
Line 27, change "-CH=CH-$(CH_2)_2$-" to -- -CH=CH-$(CH_2)_2$- --;
Line 28, change "$_{CF2}O$-" to -$OCF_2$- --;
Line 28, change "$OCF_2$-" to -- -$OCF_2$- --.
Line 46, change "repreby" to -- represented by --; and Column 147,
Line 10, change "$CF_2O$-" to -- -$CF_2O$- --.

Signed and Sealed this

Twenty-seventh Day of May, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,207,076 B1
DATED         : March 27, 2001
INVENTOR(S)   : Kouji Koga et al.

It is certified that error appears in the above-identified patent and that said Letters Patent is hereby corrected as shown below:

Column 16,
Line 10, change "wherein $R_{11}$ m and $L_1$ to L5" to -- wherein $R_1$, m and $L_1$ to $L_8$ --;
Line 25, change "4-cyclohexylene" to -- 1,4-cyclohexylene --;

Column 25,
Line 44, change "wherein $R_{11}$ $R_{21}$ m and" to -- wherein $R_1$, $R_2$, m and --;

Column 88,
Line 25, change "at SoC or less" to -- at 5°C or less --;

Column 99,
Line 58, change "$C_2H_5$ 2 F" to -- $C_2H_5$ 2 H --;

Column 100,
Line 8, change "$C_2H_5$ 2 H" to -- $C_2H_5$ 2 F --;

Column 105,
Line 63, change "$OCF_2O$" to -- $OCF_2$ --;

Column 106,
Lines 8, 12, 17, 21, 25, 29, 34 and 40, change "$OCF_2O$" to -- $OCF_2$ --;

Column 107,
Line 20, change "$CH_3$ 0 F" to -- $CH_3$ 0 H --;

Column 108,
Line 20, change " 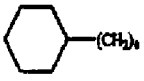 " to -- 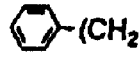 --;

Line 55, change " 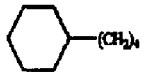 " to --  --;

Column 109,
Line 5, change " 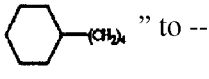 " to -- 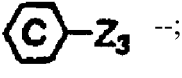 --;

UNITED STATES PATENT AND TRADEMARK OFFICE
CERTIFICATE OF CORRECTION

PATENT NO. : 6,207,076 B1
DATED : March 27, 2001
INVENTOR(S) : Kouji Koga et al.

It is certified that error appears in the above-identified patent and that said Letters Patent is hereby corrected as shown below:

Column 132,
Line 66, change "$T_{NI} = 3.8(^{\circ}C.)$" to -- $T_{NI} = 73.8(^{\circ}C.)$ --;

Column 134,
Line 60, change "p is 0, is 1, $Z_2$ is" to -- p is 0 q is 1, $Z_2$ is --;

Column 139,
Line 1, change "X, m, Z, and p" to -- X, m, $Z_1$ and p --;

Column 142,
Line 49, change "—$Z_6$—$Z_7$" to -- —$Z_8$—$Z_7$ --;

Column 143,
Line 1, change "I, J and 1< are" to -- I, J and K are --;
Line 5, change "-$CH_2C1$-$1_z$-" to -- -$CH_2CH_2$- --;
Line 50, change "—$Z_6$—$Z_7$" to -- —$Z_8$—$Z_7$ --;

Column 144,
Line 2, change "rings, J and 1< are" to -- rings, J and K are --;
Line 6, change "-$CH_2C1$-$1_2$-" to -- $CH_2CH_2$- --;

Column 145,
Line 36, change "—$Z_6$—$Z_7$" to -- —$Z_8$—$Z_7$ --;
Line 57, change "rings, J and 1< are" to -- rings, J and K are --;
Line 61, change "-$CH_2C1$-$l_z$-" to -- $CH_2CH_2$- --;
Line 64, change "represent by" to -- represented by --;

UNITED STATES PATENT AND TRADEMARK OFFICE
CERTIFICATE OF CORRECTION

PATENT NO. : 6,207,076 B1
DATED : March 27, 2001
INVENTOR(S) : Kouji Koga et al.

It is certified that error appears in the above-identified patent and that said Letters Patent is hereby corrected as shown below:

Column 146,
Line 27, change "-CH=CH-(CH$_2$)$_2$-" to -- -CH=CH-(CH$_2$)$_2$- --;
Line 28, change "$_{CF2}$O-" to -- -CF$_2$ O- --;
Line 28, change "OCF$_2$-" to -- -OCF$_2$- --;
Line 46, change "repreby" to -- represented by --; and Column 147,
Line 10, change "CF$_2$O-" to -- -CF$_2$O- --.

This certificate supersedes Certificate of Correction issued May 27, 2003.

Signed and Sealed this

First Day of November, 2005

JON W. DUDAS
*Director of the United States Patent and Trademark Office*